US012606812B2

(12) United States Patent
Alvarenga Da Silva et al.

(10) Patent No.: US 12,606,812 B2

(45) Date of Patent: Apr. 21, 2026

(54) BIOCATALYSTS FOR ORGANIC SYNTHESIS

(71) Applicants: ENGINZYME AB, Solna (SE); BUNGE SA, Geneva (CH)

(72) Inventors: Natalia Alvarenga Da Silva, Bandhagen (SE); Elin Stridfeldt, Bromma (SE); Alexey Volkov, Årsta (SE); Federica Ruggieri, Enskede (SE); Peter Hendil-Forssell, Segeltorp (SE); Carl Rämgård, Stockholm (SE); Thomas Baumgarten, Solna (SE); Ashley Mattey, Solna (SE); Vince Murphy, Sundbyberg (SE); Matthew P. Thompson, Gantofta (SE); Alden M. Clemments, Hägersten (SE); Sebastian Gergel, Solna (SE)

(73) Assignees: ENGINZYME AB, Solna (CH); BUNGE SA, Geneva (CH)

( * ) Notice: Subject to any disclaimer, the term of this patent is extended or adjusted under 35 U.S.C. 154(b) by 0 days.

(21) Appl. No.: 18/951,938

(22) Filed: Nov. 19, 2024

(65) Prior Publication Data

US 2025/0075200 A1 Mar. 6, 2025

Related U.S. Application Data

(63) Continuation of application No. PCT/EP2023/064326, filed on May 29, 2023.

(30) Foreign Application Priority Data

May 27, 2022 (SE) .................................... 2250635-6

(51) Int. Cl.
*C12N 11/14* (2006.01)
*C12N 9/20* (2006.01)

(52) U.S. Cl.
CPC ................ *C12N 11/14* (2013.01); *C12N 9/20* (2013.01); *C12Y 301/01003* (2013.01)

(58) Field of Classification Search
CPC .......... C12N 11/14; C12N 9/20; C12N 11/06; C12Y 301/01003
See application file for complete search history.

(56) References Cited

U.S. PATENT DOCUMENTS

2013/0109072 A1 5/2013 Tsunoda et al.

FOREIGN PATENT DOCUMENTS

| | | | |
|---|---|---|---|
| JP | H0930809 | A | 2/1997 |
| JP | 2002176974 | A | 6/2002 |
| JP | 2020001936 | A | 1/2020 |
| WO | 2013078551 | A1 | 6/2013 |
| WO | 2015115993 | A1 | 8/2015 |
| WO | 2016075219 | A1 | 5/2016 |

OTHER PUBLICATIONS

Agudelo et al. "Understanding of the formation of mesocellular-like silica foam particles of nano size and its chemical surface to immobilization of Thermomyces lanuginosus lipase" Microporous and Mesoporous Materials 294 (2020) 109948, 8 pages (Year: 2020).*

Machado et al "Preparation, functionalization and characterization of rice husk silica for lipase immobilization via adsorption" Enzyme and Microbial Technology 128 (2019) 9-21 (Year: 2019).*

Sypabekova et al. "Review: 3-Aminopropyltriethoxysilane (APTES) Deposition Methods on Oxide Surfaces in Solution and Vapor Phases for Biosensing Applications" Biosensors 2023, 13, 36., 25 pages (Year: 2023).*

Fathi et al. "Noncovalent Immobilization of Yarrowia lipolytica Lipase on Dendritic-Like Amino Acid-Functionalized Silica Nanoparticles" Biomolecules 2019, 9, 502;, 10 pages (Year: 2019).*

Yu et al. "Immobilization of lipase onto aminopropyl-functionalized MSU-H type mesoporous silica and esterification" Korean J. Chem. Eng., 32(8), 1694-1700 (2015) (Year: 2015).*

Bernal et al. "Raising the enzymatic performance of lipase and protease in the synthesis of sugar fatty acid esters, by combined ionic exchange-hydrophobic immobilization process on aminopropyl silica support" Chemical Engineering Journal 334 (2018) 760-767 (Year: 2018).*

Barão et al. "Characterization of Free and Immobilized Thermomyces lanuginosus Lipase for Use in Transesterification Reactions" Industrial Biotechnology vol. 10, No. 4, Aug. 2014, 5 pages (Year: 2014).*

Peng et al. "Production of structured phospholipids by lipase-catalyzed acidolysis: optimization using response surface methodology" Enzyme and Microbial Technology 31 (2002) 523-532 (Year: 2002).*

Trevisan et al., "Preparation of silica with controlled pore sizes for enzyme immobilization"; Brazilian Journal of Chemical Engineering, vol. 17, No. 1, pp. 71-77 (2000), HTML version provided, pp. 1-7.

Soares et al., "Covalent Coupling Method for Lipase Immobilization on Controlled Pore Silica in the Presence of Nonenzymatic Proteins"; Biotechnol. Prog., vol. 19, No. 3, pp. 803-807 (2008).

Dehghanifard et al., "Biodegradation of 2,4-dinitrophenol with laccase immobilized on nano-porous silica beads"; Iranian Journal of Environmental Health Science & Engineering, vol. 10:25, pp. 1-9 (2013).

Thermo Scientific; "Cross-Linking Technical Handbook"; pp. 1-56; available at http://tools.thermofisher.com/content/sfs/brochures/1602163-Crosslinking-Reagents-Handbook.pdf; last accessed Aug. 24, 2021 (2012).

(Continued)

*Primary Examiner* — Thane Underdahl

(74) *Attorney, Agent, or Firm* — EVENTIDE LAW LLC

(57) ABSTRACT

The invention relates to a biocatalyst for organic synthesis, comprising a controlled porosity silica (CPS) as support material, wherein the pore diameter is between about 20 and about 100 nm, said support material comprising an amino-functionalized surface; and one or more catalytically active enzyme(s) immobilized on the support material. The invention also relates to uses of such biocatalysts and methods of manufacture thereof.

3 Claims, 3 Drawing Sheets

(56) References Cited

OTHER PUBLICATIONS

Weetall, "Preparation of Immobilized Proteins Covalently Coupled Through Silane Coupling Agents to Inorganic Supports"; Applied Biochemistry and Biotechnology, vol. 41, pp. 157-188 (1993).
Nagy et al., "Cross-Linked Enzyme-Adhered Nanoparticles (CLEANs) for Continuous-Flow Bioproduction"; ChemSusChem, vol. 15, e202102284, pp. 1-9 (2022).
Nagy et al., "Smart Nanoparticles for Selective Immobilization of Acid Phosphatases"; ChemCatChem, vol. 10, pp. 3490-3499 (2018).
Boros et al., "Hydrophobic adsorption and covalent immobilization of Candida antarctica lipase B on mixed-function-grafted silica gel supports for continuous-flow biotransformations"; Process Biochemistry, vol. 48, pp. 1039-1047 (2013).
Barbosa et al., "Heterofunctional Supports in Enzyme Immobilization: From Traditional Immobilization Protocols to Opportunities in Tuning Enzyme Properties"; BioMacromolecules, vol. 14, pp. 2433-2462 (2013).
Search Report for International Application No. PCT/EP2023/064326 dated Oct. 9, 2023, pp. 1-8.
Yoshimi, T. et al., "Phase Transitions of N-(4-methoxybenzylidene)-4-butylaniline (MBBA) Confined within Mesoporous Silica," Crystals 2020, 10, 792, pp. 1-8; doi:10.3390/cryst10090792, Sep. 8, 2020.
Tanimu, G. et al., "Pore Structure Effect of Support in Ni—Bi—O/Mesoporous Silica Catalyst on Oxidative Dehydrogenation of n-Butane to Butadiene," Catalysis Today, vol. 324, pp. 97-105, Mar. 1, 2019, available at: https://doi.org/10.1016/j.cattod.2018.06.014, provided as Accepted Manuscript, pp. 1-34.
Nagy, F. et al., "Bisepoxide-activated Hollow Silica Microspheres for Covalent Immobilization of Lipase from Burkholderia cepacia," Periodica Polytechnica Chemical Engineering, 63(3), pp. 414-424, 2019.
FDA, "Unii record A370TYK9KO: Amyloglucosidase (Aspergillus niger)," Global Substance Registration System Ver 3.0.3, available at: https://precision.fda.gov/uniisearch/srs/unii/A370TYK9KO, last accessed Jun. 13, 2025, p. 1.
Cuetos, A et al., "Catalytic Promiscuity of Transaminases: Preparation of Enantioenriched β-Fluoroamines by Formal Tandem Hydrodefluorination/Deamination," Angew Chem Int Ed Engl.; vol. 55, pp. 3144-3147 (2016), Abstract Only.
Godat, B. et al., "Metal Affinity Tag for Protein Expression and Purification using the Flexi® Vectors," Promega Notes No. 91 p. 17-20 (2005), available at https://www.promega.com/resources/pubhub/promega-notes-2005/metal-affinity-tag-for-protein-expression-and-purification-using-the-flexi-vectors/, last accessed Jun. 13, 2025.
Beerens, K. et al., "Biocatalytic Synthesis of the Rare Sugar Kojibiose:Process Scale-Up and Application Testing," J Agric Food Chem., vol. 65, pp. 6030-6041 (2017), Abstract Only.
Fuji Silysia Chemical Ltd., "Technology: Silica-gel & Silica Types," pp. 1-2 (2013), available at https://www.fujisilysia.com/technology/, last accessed Jun. 16, 2025.
Schmidt-Winkel, et al., "Mesocellular Siliceous Foams with Uniformly Sized Cells and Windows," J. Am. Chem. Soc., 1999, vol. 121, pp. 254-255.
Holm, et al., "Upscaling of Enzymatic Processes," in "Lipid Modification by Enzymes and Engineered Microbes," pp. iii-vii and 343-373 (Uwe T. Bornscheuer, ed., 2018) AOCS Press, published by Elsevier Incorporated.
Yoshimi, "Phase Transitions of N-(4-methoxybenzylidene)-4-butylaniline (MBBA) Confined within Mesoporous Silica," Crystals, 2020, vol. 10, 792, doi:10.3390/cryst10090792, pp. 1-8.

* cited by examiner

BIOCATALYSTS FOR ORGANIC SYNTHESIS

CROSS-REFERENCE TO RELATED APPLICATIONS

This application is a continuation of International Application No. PCT/EP2023/064326, filed May 29, 2023, which claims priority from Swedish Application No. 2250635-6, filed May 27, 2022, each of which is incorporated herein by reference.

TECHNICAL FIELD

The present invention relates to biocatalysts for organic synthesis, where an enzyme is immobilized on a controlled porosity silica having an amino-modified surface. The present invention also relates to uses of such biocatalysts and methods of manufacture of such biocatalysts.

BACKGROUND TO THE INVENTION

Enzymes serve as biological catalysts in the metabolism of all living cells. As such, enzymes are able to transform organic molecules into different molecules. Because of the specific three-dimensional structure of each particular enzyme, only certain organic molecules will interact with the enzyme's active site in such a way that transformation can take place. Enzymes are therefore usually highly selective catalysts, and the use of enzymes as catalysts in synthetic organic chemistry is for that reason very appealing. However, since enzymes are biological molecules evolved for a cell environment, they are often unsuited for other environments. When used in organic solvents, enzymes tend to aggregate and often precipitate or unfold (i.e., denature). It is therefore attractive to immobilize enzymes on solid support and to use them as catalysts in this immobilized state, as this may improve the stability of the enzyme, allow for reaction conditions which the enzyme normally would not tolerate and furthermore facilitate the separation from the reaction mixture and recovery of the material. The immobilization also makes it possible to use immobilized enzymes in much higher concentrations than would have been possible with the free enzymes in solution.

A desirable industrial scale synthesis method using biocatalysts would require that the enzyme be immobilized on a suitable support and packed within a fixed-bed reactor suitable for operation in a continuous-flow mode. This presents additional challenges for the support material used in the immobilization, to tolerate the pressure and enable sufficient flow rates. Immobilization of enzymes on solid support has been previously accomplished using different techniques and different solid supports.

PCT/SE2015/050108 discloses biocatalysts with enzymes immobilized through metal chelation to controlled porosity glass beads or porous organic beads as support material. While controlled porosity glass works well in terms of activity, the support material is expensive and brittle.

Nagy et al. (ChemCatChem 2018, 10, 3490-3499) disclose covalent immobilization of acid phosphatases to silica nanoparticles for biocatalytic applications. Due to prohibitively high back pressure, the biocatalytic nanoparticles were mixed with larger particles of inert silica for continuous flow applications.

JP2002176974 discloses R-hydroxynitrile lyase immobilized by physical adsorption on a porous clay-based sintered carrier or a porous silica-based carrier. The carriers were not surface-modified. Notably, covalent cross-linking resulted in significant loss of activity.

Trevisan et al. (Braz. J. Chem. Eng. 17 (1) March 2000) disclose a method for the preparation of silica with controlled pore size, for use as a support for the immobilization of enzymes. The surface was aminopropyl-modified and aminoglucosidase was coupled to the surface using glutaraldehyde.

Nagy et al. (Periodica Polytechnical Chemical Engineering 2019, vol. 63(3), pages 414-424) disclose immobilization of *Burkholderia cepacia* lipase on hollow silica microspheres (M540) by bisepoxide activation.

Nagy et al (ChemSusChem 2021, pages 1-10 and supporting information pages 1-12) disclose covalent immobilization of Lipase B from *Candida antarctica* (CaLB) on various functionalized silica nanoparticles.

Thus, an object of the present invention is the provision of improved and/or alternative means and methods for conducting biocatalysis.

DEFINITIONS

Figure 1:
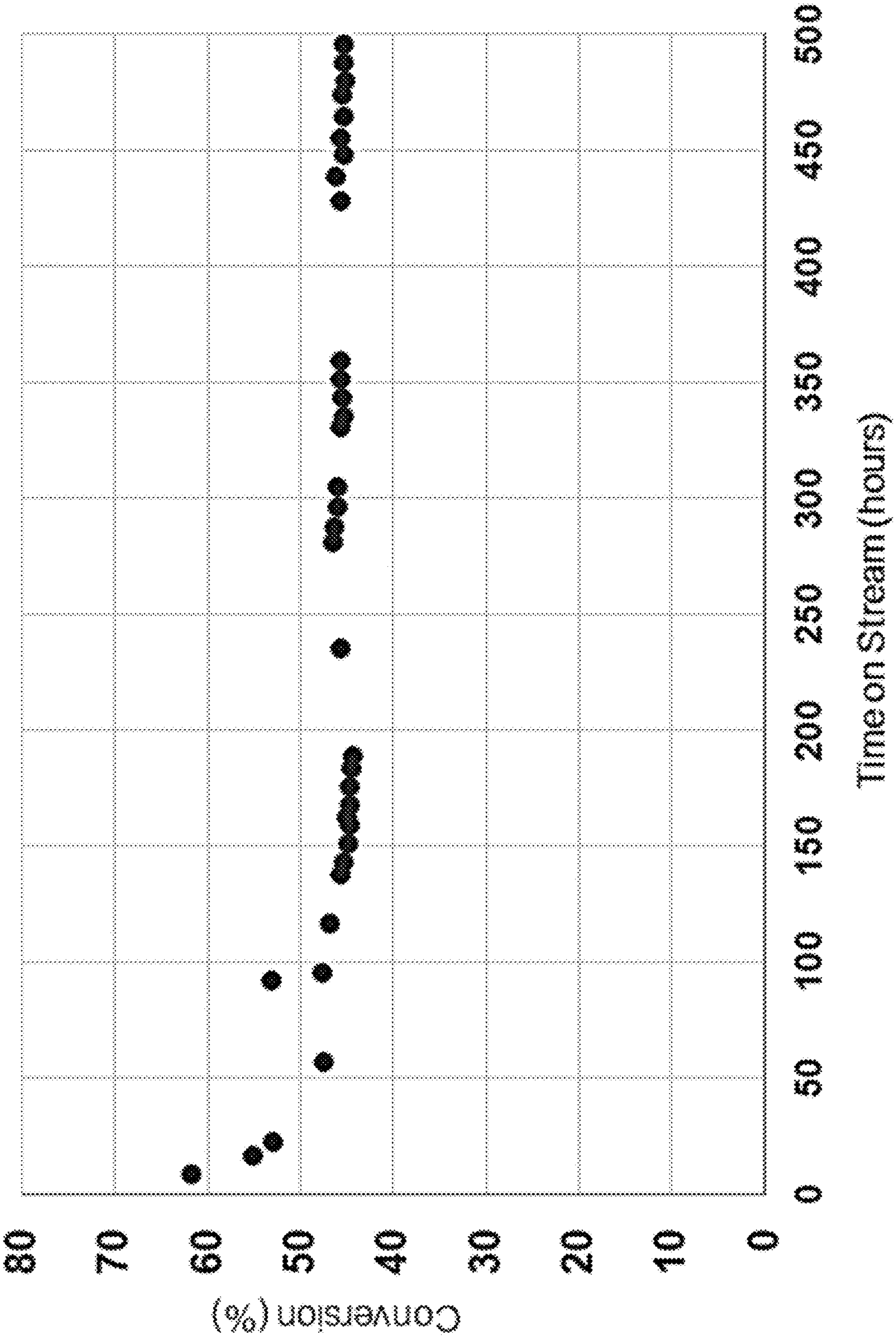
FIG. 1: Data from Table 20 plotted as conversion rate against time on stream, illustrating excellent stability of an immobilized sucrose phosphorylase biocatalyst over time in industrial conditions.

The term multi-step synthesis refers to a reaction wherein the starting material is converted to the product through at least one intermediate. As used in this context, the term "step" or "steps" refers to one or more of the individual steps that together form the total steps of the multi-step synthesis. Thus, a "step" of the multi-step synthesis may refer to the conversion of a starting material to a first intermediate, the conversion of one intermediate to the next intermediate, or the conversion of the last intermediate to the product. The multi-step synthesis may be a linear synthesis, wherein a single starting material is converted to the final product in a linear series of consecutive steps, or a convergent synthesis, wherein two or more starting materials are converted to a single final product in a converging series of steps. Each individual enzyme-catalyzed step of the synthesis is catalyzed by at least one of the enzymes that are immobilized on the support material. Any simultaneously occurring reactions that are catalyzed by immobilized enzymes but that do not directly involve the conversion of the starting material or any of the intermediates to the product (e.g., reactions involving the regeneration of cofactor or co-enzyme) are herein not considered as "steps" in the multi-step synthesis.

The term surface as used herein in the context of the biocatalyst of the invention refers to the entire surface of the controlled porosity silica (CPS) support material and includes both the outer surface and the surface of the pores. Due to the nature of the CPS, the greater part of the surface area is present in the pores.

The term sequence identity expressed in percentage is defined as the value determined by comparing two optimally aligned sequences over a comparison window, wherein a portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Unless indicated otherwise, the comparison window is the entire length of the sequence being referred to. In this context, optimal alignment is the alignment produced by the BLASTP algorithm as implemented online by the US National Center for Biotechnology Information (see The NCBI Handbook, $2^{nd}$ edition, website: ncbi.nlm.nih.gov/books/NBK143764/), with the following input parameters: Word length=3, Matrix=BLOSUM62, Gap cost=11, Gap extension cost=1.

As used herein, the term "about" refers to a value or parameter herein that includes (and describes) embodiments that are directed to that value or parameter per se. For example, description referring to "about 20" includes description of "20." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater.

The term continuous flow reactor refers to a reactor designed to be operated such that a reactant or reactants are substantially continuously fed into the reactor in a feed stream, whereby a substantially continuous product stream emerges from the reactor containing at least one reaction product. In operation, at least a portion of the product stream (preferably all of the product stream) is collected and may optionally be subjected to further processing steps such as a purification step or a second reactor. Any part of the product stream that is not collected can be fed back to the reactor as part of the feed stream.

SUMMARY OF THE INVENTION

The present invention relates to the following items. The subject matter disclosed in the items below should be regarded disclosed in the same manner as if the subject matter were disclosed in patent claims.

1. A biocatalyst for organic synthesis, comprising:
 a. a controlled porosity silica (CPS) as support material, having a pore diameter from about 20 to about 100 nm;
 wherein the support material comprises an amino-functionalized surface; and
 b. one or more catalytically active enzyme(s) immobilized to the amino-functionalized surface by a covalent linker comprising a bond selected from amino, amide and imidoamide.

2. A biocatalyst for organic synthesis, comprising:
 a. a controlled porosity silica (CPS) as support material, having a pore diameter from about 20 to about 100 nm;
 wherein the support material comprises an amino-functionalized surface; and
 b. one or more catalytically active enzyme(s) immobilized to the surface via non-covalent interactions.

3. A biocatalyst for organic synthesis, comprising:
 a. a controlled porosity silica (CPS) as support material, having a pore diameter from about 20 to about 100 nm;
 wherein the support material surface comprises at least two different coatings, of which at least one provides an amino functionalized surface; and
 b. one or more catalytically active enzyme(s) immobilized on the surface, optionally by a covalent linker comprising a bond selected from amino, amide and imidoamide.

4. A biocatalyst for organic synthesis, comprising:
 a. a controlled porosity silica (CPS) as support material, having a pore diameter from about 20 to about 100 nm;
 wherein the support material comprises an amino-functionalized surface; and
 b. one or more catalytically active enzyme(s) immobilized to the amino-functionalized surface, optionally by a covalent linker comprising a bond selected from amino, amide and imidoamide, wherein the enzyme(s) is/are selected from list (A), preferably from list (B).

5. The biocatalyst according to item 1, 3 or 4, wherein the covalent linker, when present, comprises a bond selected from the group consisting of amino and amide.

6. The biocatalyst according to any of the preceding items, wherein the support material has a pore diameter from about 20 to about 60 nm.

7. The biocatalyst according to any of the preceding items, wherein the support material has a surface area from about 50 $m^2/g$ to about 200 $m^2/g$.

8. The biocatalyst according to any of the preceding items, wherein the support material has a pore volume from about 0.5 mL/g to about 2.0 mL/g.

9. The biocatalyst according to any of the preceding items, wherein the support material has a pore diameter from about 20 to about 60 nm and a surface area from about 50 $m^2/g$ to about 200 $m^2/g$.

10. The biocatalyst according to any of the preceding items, wherein the support material has a pore diameter from about 20 to about 60 nm, a surface area from about 50 $m^2/g$ to about 200 $m^2/g$ and a pore volume from about 0.5 mL/g to about 2.0 mL/g.

11. The biocatalyst according to item 1, 2, 3 or any item dependent thereon, wherein the enzyme(s) are selected from list (A), preferably from list (B).

12. The biocatalyst according to any of items 1-9, wherein the support material has a pore diameter from about 20 to about 60 nm, a surface area from about 50 $m^2/g$ to about 200 $m^2/g$ and a pore volume of from about 0.5 mL/g to about 2.0 mL/g, and wherein the enzyme(s) are selected from list (A), preferably from list (B).

13. The biocatalyst according to any of the preceding items, wherein the support material surface comprises at least two different coatings, of which at least one provides the amino functionalization.

14. The biocatalyst according to item 13, wherein the relative amount of the two coatings is in the range of 9:1 to 1:9 on weight basis, preferably 5:1 to 1:5, more preferably 2:1 to 1:2, most preferably 1:1.

15. The biocatalyst according to any of items 13-14, wherein one of the coatings, which does not provide amino functionalization, provides a hydrophobic coating.

16. The biocatalyst according to item 15, wherein the hydrophobic coating comprises alkyl moieties and/or aromatic moieties.

17. The biocatalyst according to item 16, wherein the hydrophobic coating comprises $C_{1-12}$ alkyl groups, preferably $C_{1-6}$ alkyl groups.

18. The biocatalyst according to any of the preceding items, wherein the immobilized enzyme(s) are intermolecularly covalently linked by a linker comprising a bond selected from amino, amide, ester, ether, thioester, imidoamide, imidothioamide, thioether and thioamide.

19. The biocatalyst according to item 3, 4 or any item dependent thereon, wherein the enzyme(s) is/are immobilized to the surface by a covalent linker comprising a bond selected from amino, amide and imidoamide.

20. The biocatalyst according to item 1, 3, 4 or any item dependent thereon, wherein the enzyme(s) is/are immobilized to the surface by a covalent linker comprising a bond selected from amino, amide and imidoamide, and wherein prior to formation of the bond, the enzyme(s) had been immobilized to the surface via non-covalent interactions.

21. The biocatalyst according to item 20, wherein prior to formation of the bond, the enzyme(s) had been immobilized to the surface via an interaction mediated by a chelated metal ion.

22. The biocatalyst according to item 2, 3, 4 or any item dependent thereon, wherein the enzyme(s) is/are immobilized to the surface via an interaction mediated by a chelated metal ion.

23. The biocatalyst according to item 21 or 22, wherein the chelated metal ion is selected from $Ni^{2+}$, $Cu^{2+}$, $Mg^{2+}$, $Fe^{3+}$ and $Zn^{2+}$.

24. The biocatalyst according to item 23, wherein the metal ion is a $Zn^{2+}$ ion.

25. The biocatalyst according to any of the preceding items, wherein the covalent linker between the surface and the enzyme(s), when present, does not comprise imine bonds.

26. The biocatalyst according to any of the preceding items, wherein the intermolecular covalent linker, when present, does not comprise imine bonds.

27. The biocatalyst according to any of the preceding items, wherein the covalent linker, when present, comprises a bridge containing between 3 and 20 atoms comprising any combination of C, H, N and O.

28. The biocatalyst according any of the preceding items, wherein the covalent linker, when present, was formed using a bifunctional reagent, preferably containing at least two reactive groups independently selected from epoxides, esters, anhydrides, N-hydroxysuccinimide esters, imidoesters, carbonates, acylisoureas, carbodiimides, maleimides, haloacetyls, thiosulfonates, isocyanates and vinylsulfones.

29. The biocatalyst according to any of the preceding items, wherein the amino-functionalized surface comprises a structure of formula (I), (II) or (III):

(I)

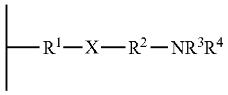

(II)

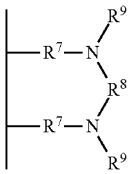

-continued (III)

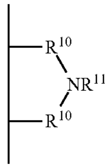

wherein $R^1$ is $C_{1-6}$ alkanediyl; and wherein $R^1$ provides a covalent attachment to the silica surface (the vertical line on the left);

X is a bond (i.e., X is absent) or is a phenyl ring;

$R^2$ is $C_{1-6}$ alkanediyl;

$R^3$ is W;

$R^4$ is W or is selected from the group consisting of $C_{1-10}$ alkyl, $C_{5-7}$ cycloalkyl, phenyl, phenyl-$C_{1-6}$-alkyl, amino-$C_{2-8}$ alkyl, N-(phenyl)amino-$C_{2-8}$ alkyl and N-(phenyl-$C_{1-6}$-alkyl)amino-$C_{2-8}$ alkyl, and aminocarbonyl, wherein each amino is substituted with W; and wherein phenyl, at each instance, is optionally substituted with one or more substituents $C_{1-4}$ alkyl;

or $R^3$ and $R^4$, together with the nitrogen atom to which they are attached, combine to form a 5- to 7-membered heterocyclic ring which may contain one or more unsaturated bonds and which may contain one more additional heteroatoms, on which a covalent linker comprising a bond selected from amino, amide and imidoamide is optionally attached, wherein a catalytically active enzyme also is attached to the linker;

or $R^3$ and $R^4$ together form $=CR^5R^6$, wherein $R^5$ and $R^6$ are each independently $C_{1-4}$ alkyl;

Each $R^7$ is independently $C_{1-6}$ alkanediyl; and wherein $R^7$ provides a covalent attachment to the silica surface (the vertical line on the left);

$R^8$ is $C_{1-3}$ alkanediyl;

Each $R^9$ is independently W or is selected from the group consisting of $C_{1-4}$ alkyl and hydroxy-$C_{1-4}$ alkyl;

Each $R^{10}$ is independently $C_{1-6}$ alkanediyl; and wherein $R^{10}$ provides a covalent attachment to the silica surface (the vertical line on the left);

$R^{11}$ is W or is selected from the group consisting of $C_{1-10}$ alkyl, $C_{5-7}$ cycloalkyl, phenyl, phenyl-$C_{1-6}$-alkyl, amino-$C_{2-8}$ alkyl, N-(phenyl)amino-$C_{2-8}$ alkyl and N-(phenyl-$C_{1-6}$-alkyl)amino-$C_{2-8}$ alkyl, and aminocarbonyl, wherein each amino is substituted with W; and wherein phenyl, at each instance, is optionally substituted with one or more substituents $C_{1-4}$ alkyl; and each W is independently hydrogen or a covalent linker comprising a bond selected from amino, amide and imidoamide, wherein a catalytically active enzyme is also attached to the linker.

30. The biocatalyst according to any of the preceding items, wherein the amino-functionalized surface comprises a structure of formula (I), as defined above, in combination with a structure of formula (IV):

(IV)

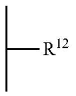

wherein $R^{12}$ is selected from $C_{1-12}$ alkyl and amino-$C_{1-6}$ alkyl.

31. The biocatalyst according to any of the preceding items, wherein the amino functional groups in the surface are not part of a heterocyclic ring.

32. The biocatalyst according to any of the preceding items, wherein the surface does not contain any functional groups that may chelate a metal ion apart from the amino groups.

33. The biocatalyst according to any of the preceding items, wherein the surface comprises amino-functionalized aliphatic moieties.

34. The biocatalyst according to any of the preceding items, wherein the amino-functionalized surface comprises any of the following structures, wherein each W is hydrogen or a covalent linker comprising a bond selected from amino, amide and imidoamide, wherein a catalytically active enzyme is also attached to the linker:

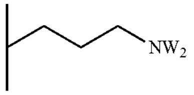

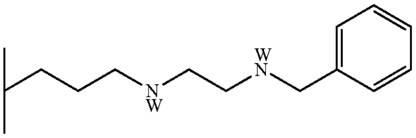

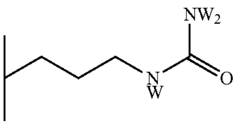

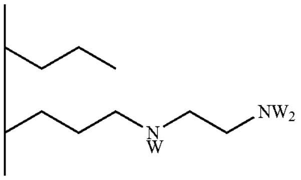

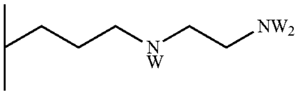

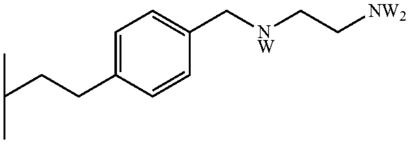

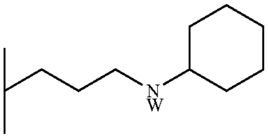

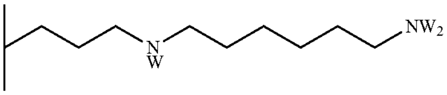

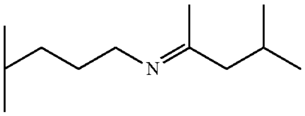

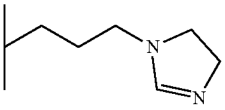

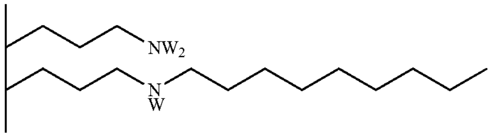

-continued

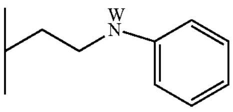

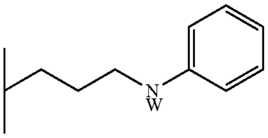

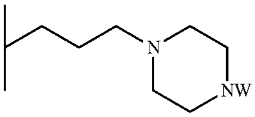

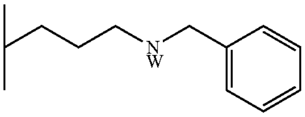

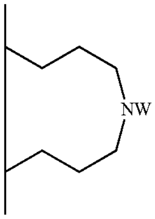

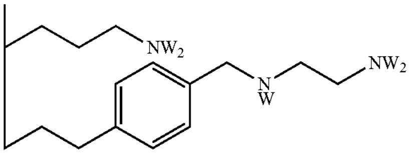

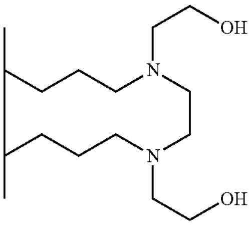

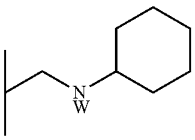

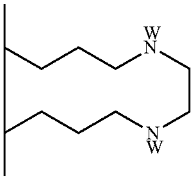

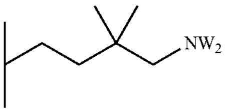

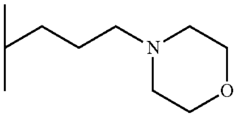

35. The biocatalyst according to any of the preceding items, wherein the amino-functionalized surface comprises structure (I'):

(I')

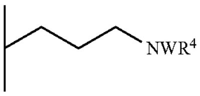

wherein $R^4$ is W or is selected from the group consisting of phenyl, phenyl-$C_{1-6}$-alkyl, amino-$C_{2-8}$ alkyl, N-(phenyl)amino-$C_{2-8}$ alkyl and N-(phenyl-$C_{1-6}$-alkyl)amino-$C_{2-8}$ alkyl, and wherein phenyl, at each instance, is optionally substituted with one or more substituents $C_{1-4}$ alkyl; and W is hydrogen or a covalent linker comprising a bond selected from amino, amide and imidoamide, wherein a catalytically active enzyme is also attached to the linker;

or wherein the amino-functionalized surface comprises structure (I"):

(I'')

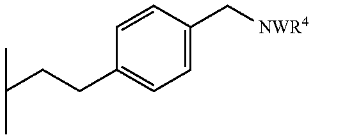

wherein $R^4$ is W or is selected from the group consisting of amino-$C_{2-8}$ alkyl, N-(phenyl)amino-$C_{2-8}$ alkyl and N-(phenyl-$C_{1-6}$-alkyl)amino-$C_{2-8}$ alkyl, and wherein phenyl, at each instance, is optionally substituted with one or more substituents $C_{1-4}$ alkyl; and W is hydrogen or a covalent linker comprising a bond selected from amino, amide and imidoamide, wherein a catalytically active enzyme is also attached to the linker.

36. The biocatalyst according to item 34, wherein the amino-functionalized surface comprises structure I' wherein $R^4$ is W or is selected from the group consisting of phenyl, benzyl, amino-$C_{2-6}$ alkyl, N-(phenyl)amino-$C_{2-6}$ alkyl and N-(benzyl)amino-$C_{2-6}$ alkyl; or the amino-functionalized surface comprises structure I'' wherein $R^4$ is W.

37. The biocatalyst according to any of the preceding items, wherein the amino-functionalized surface comprises any of the following structures, wherein each W is hydrogen or a covalent linker comprising a bond selected from amino, amide and imidoamide, wherein a catalytically active enzyme is also attached to the linker:

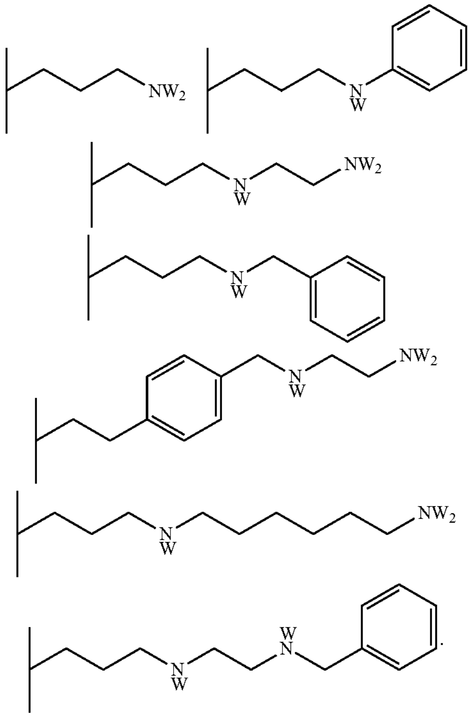

38. The biocatalyst according to any of the preceding items, wherein the amino-functionalized surface comprises any of the following structures, wherein each W is hydrogen or a covalent linker comprising a bond selected from amino, amide and imidoamide, wherein a catalytically active enzyme is also attached to the linker:

(1)

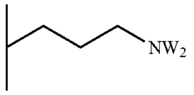

(2)

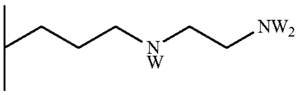

(3)

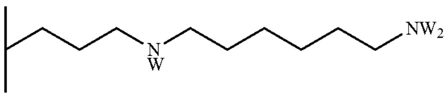

(4)

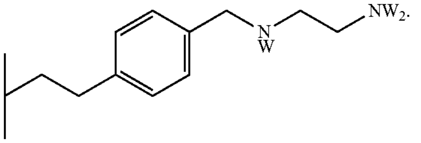

39. The biocatalyst according to any of the preceding items, wherein the immobilized enzyme(s) is/are selected from: *Bifidobacterium adolescentis* sucrose phosphorylase (SucP), *Candida antarctica* lipase (CalB), *Thermoanaerobacter brockii* secondary alcohol dehydrogenase (TbSADH), amine transaminase (ATA), *Leuconostoc mesenteroides* glycosyl transferase (GT), *Thermomyces lanuginosus* lipase (TLL), and *Aspergillus niger* amyloglucosidase.

40. The biocatalyst according to any of the preceding items, wherein at least one immobilized enzyme retains at least 20% of its activity after immobilization compared to the state prior to immobilization.

41. The biocatalyst according to any of the preceding items, wherein at least one immobilized enzyme retains at least 50% of its activity after 20 h under continuous flow conditions compared to the state prior to immobilization.

42. The biocatalyst according to any of the preceding items, wherein at least two different enzymes are immobilized on the support material.

43. The biocatalyst according to item 42, wherein the at least two immobilized enzymes are each capable of catalyzing a different step of a multi-step organic synthesis.

44. The biocatalyst according to item 43, wherein the multi-step synthesis comprises at least 3 intermediates.

45. The biocatalyst according to any of the preceding items, wherein at least one of the immobilized enzymes catalyzes the regeneration of a cofactor.

46. The biocatalyst according to any of items 1-45, wherein a lipase (preferably CalB) comprising a metal chelating tag such as a His-tag is immobilized to a surface comprising amino-functionalized aliphatic moieties via an interaction mediated by a chelated $Zn^{2+}$ ion.

47. The biocatalyst according to any of items 1-45, wherein TbSADH comprising a metal chelating tag such as a His-tag is immobilized to the surface via an interaction mediated by a chelated $Zn^{2+}$ ion.

48. The biocatalyst according to any of items 1-45, wherein ATA comprising a metal chelating tag such as a His-tag is immobilized to a surface comprising structure (1), (2), (3) or (4) via an interaction mediated by a chelated metal ion.

49. The biocatalyst according to any of items 1-45, wherein SucP comprising a metal chelating tag such as a His-tag is immobilized to a surface comprising structure (2).

50. The biocatalyst according to any of items 1-45, wherein TLL not comprising a metal chelating tag such as a His-tag is immobilized to the surface.

51. The biocatalyst according to any of items 1-45, wherein a glucosyl transferase comprising a metal chelating tag such as a His-tag is immobilized to a surface comprising structure (1).

52. The biocatalyst according to any of items 1-45, wherein the lipase CalB is immobilized to a surface comprising structure (1) or (4), preferably non-covalently, wherein the CalB most preferably does not comprise a metal chelating tag such as a His-tag.

53. The biocatalyst according to any of items 1-45, wherein an amyloglucosidase preferably not comprising a metal chelating tag such as a His-tag is immobilized on a surface functionalized with structure (1), (2), (3) or (4), and optionally with a different second functionalization which may be structure (1) or an alkyl such as propyl or octyl.

54. Use of a biocatalyst according to any of the preceding items in a reactor for synthesis of an organic compound.

55. The use according to item 54, wherein the reactor is a batch reactor or a continuous flow reactor.

56. The use according to item 54, wherein the reactor is a continuous stirred tank reactor (CSTR), a slurry bubble column or a fixed bed reactor.

57. The use according to item 55, wherein the reactor is a continuous flow fixed bed reactor.

58. The use according to any of items 54-57, wherein the synthesis takes place in aqueous conditions.

59. The use according to any of items 54-57, wherein the synthesis takes place in an organic solvent.

60. The use according to any of items 54-57, wherein the synthesis takes place in neat substrate.

61. The use according to any of items 54-60, wherein the synthesis is a multi-step synthesis.

62. The use according to item 61, wherein the multi-step synthesis comprises at least 3 intermediates.

63. The use according to item 61 or 62, wherein the multi-step synthesis is a linear synthesis.

64. A method for synthesis of an organic compound, comprising:

a. providing a biocatalyst according to any of the items 1-53, placed in a reactor;

b. feeding a precursor to the organic compound to the flow reactor, whereby the immobilized enzyme(s) catalyze(s) a reaction/reactions resulting in the synthesis of the organic compound; and c. recovering the organic compound.

65. The method according to item 54, wherein the reactor is a batch reactor or a continuous flow reactor.

66. The method according to item 65, wherein the reactor is a continuous stirred tank reactor (CSTR), a slurry bubble column or a fixed bed reactor.

67. The method according to item 65, wherein the reactor is a continuous flow fixed bed reactor.

68. The method according to any of items 64-67, wherein the reaction/reactions take(s) place in aqueous conditions.

69. The method according to any of items 64-67, wherein the reaction/reactions take(s) place in an organic solvent.

70. The method according to any of items 64-67, wherein the reaction/reactions take(s) place in neat substrate.

71. The method according to any of items 64-70, wherein the synthesis is a multi-step synthesis comprising at least two reaction steps.

72. The method according to item 71, wherein the multi-step synthesis comprises at least 3 intermediates.

73. The method according to item 71 or 72, wherein the multi-step synthesis is a linear synthesis.

74. A method of manufacturing a biocatalyst according to any of items 1-53, comprising:

a. providing one or more catalytically active enzyme(s);

b. providing a controlled porosity silica (CPS) as support material, wherein the pore diameter is between about 20 and about 100 nm, said support material comprising an amino-functionalized surface; and c. immobilizing the one or more enzyme(s) on the support material.

75. The method according to item 74, further comprising: selecting a bifunctional cross-linking reagent capable of producing amino, amide or imidoamide bonds when reacted with the enzyme(s) and/or the surface, and covalently cross-linking the enzyme(s) using the bifunctional reagent.

76. The method according to item 75, wherein the bifunctional cross-linking reagent comprises at least two reactive groups independently selected from epoxides, esters, anhydrides, N-hydroxysuccinimide esters, imidoesters, carbonates, acylisoureas, carbodiimides, maleimides, haloacetyls, thiosulfonates, isocyanates and vinylsulfones.

77. The method according to item 75, wherein the bifunctional cross-linking reagent is defined by the following formula:

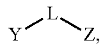

where Y and Z are independently a reactive group selected from an epoxide, ester, anhydride, imidoester, N-hydroxysuccinimide ester, carbonate, acylisourea, a carbodiimide, a maleimide, a haloacetyl, a thiosulfonate, a vinylsulfone and an isocyanate, and L represents a linker between the reactive groups containing between 3 and 20 atoms comprising any combination of C, H, N and O.

78. The method according to item 77, where Y and Z are each independently epoxide, N-hydroxysuccinimide ester or imidoester, wherein preferably Y=Z.

79. The method according to item 77, wherein the bifunctional reagent is a bis-epoxide reagent, a bifunctional sulfonated N-hydroxysuccinimide ester or a bifunctional imidoester.

80. The method according to item 77, wherein the reagent is a bis-epoxide defined by the following formula:

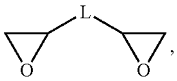, where L represents a linker containing between 3 and 20 atoms comprising any combination of C, H, N and O.

81. The method according to item 77, wherein the reagent is GDE, NPE, PDE, BS3 or DMS.

82. The method according to item 77, wherein the bifunctional reagent is a bifunctional sulfonated N-hydroxysuccimide ester reagent or a bifunctional imidoester.

83. The method according to item 82, wherein the reagent is bis(sulfosuccinimidyl)suberate (BS3) or dimethyl suberimidate (DMS).

84. The method according to any of items 75-83, wherein the bifunctional reagent is contacted with the support material prior to immobilizing the enzyme(s).

85. The method according to any of items 75-84, wherein the bifunctional reagent is contacted with the support material after immobilizing the enzyme(s).

86. The method according to item 75 or any item dependent thereon, wherein the enzyme is immobilized to the surface via an interaction mediated by a chelated metal ion, preferably $Ni^{2+}$, $Cu^{2+}$, $Mg^{2+}$, $Fe^{3+}$ or $Zn^{2+}$, most preferably $Zn^{2+}$.

87. The method according to item 75 or any item dependent thereon, wherein at least one of the enzyme(s) comprise(s) a polyhistidine tag.

88. The method according to item 75 or any item dependent thereon, wherein enzyme(s) is/are selected from list (A), more preferably from list (B).

89. The method according to item 75 or any item dependent thereon, wherein at least one of the enzyme(s) is/are provided in a cell lysate.

90. The method according to item 75 or any item dependent thereon, wherein at least one of the enzyme(s) is/are provided as a preparation comprising at least 70% or the enzyme by weight of total protein in the preparation.

DETAILED DESCRIPTION

The present invention is based on the unexpected discovery that amino-functionalized controlled porosity silica (CPS) is broadly useful as support material for immobilizing enzymes for synthesis and in comparison, provides better results than commercially available support materials (Examples 1-4, 6). The amino functionalization of the CPS support allows immobilization of many different types of enzymes with high enzyme loadings, high retention of activity, high stability and is applicable to both His-tagged and non His-tagged enzymes. The industrial applicability of amino-functionalized CPS supports was further demonstrated in a continuous flow setting (Example 5, FIG. 1).

In Example 7, a variety of cross-linking reagents were tested on using SucP2 immobilised on amino-functionalised CPS as a model, demonstrating superiority of cross-linkers resulting in a bond selected from amino, amide and imidoamide in comparison to glutaraldehyde resulting in imine bonds.

Utility of using two different coatings on CPS for enzyme immobilization was explored in Example 8 which provides an ability tailor the functional groups on the surface.

The results in Example 9 compare different sizes of CPS Q30 particles (75-150 μm, 280-500 μm and 1.18-2.36 mm), and shows that the larger categories are also workable, which allows working in certain applications requiring higher flow rates or three-phase reactions.

Example 10 compare two different CPS silicas (Cariact Q30 and Ecovyst) functionalized with propylamine using three different application methods, showing that immobilization with similar performance could be achieved with several different methods and CPS sources.

An added benefit is that the cost of CPS is much lower than other supports such as controlled porosity glass (CPG). Compared to silica nanoparticles, CPS provides beneficial flow characteristics in packed-bed reactors, such as low back pressures at high flow rates. Compared to non-porous silica particles of larger size, the CPS surface area is much higher allowing significantly higher enzyme immobilization yields by weight of support material. In addition, the CPS support materials utilized in the invention have been specifically designed for use as catalyst supports, where mechanical properties such as crush strength, attrition and abrasion resistance are a feature of the material, meaning that the catalyst can be utilized in other reactor types, such as batch or continuous stirred tank reactors or bubble column reactors. However, in spite of these attractive features for supports for catalysts, silica surfaces are not commonly utilized for enzyme catalysts, as the silica surfaces are known to cause enzyme deactivation, and silica supports have thus far not enabled high enzyme loadings with high levels of activity retained on the support surface.

The amino-functionalized CPS support materials are chemically stable, meaning that they can be utilized in a broad range of reaction conditions such as reactions in aqueous solutions, in organic solvents and reactions in which no solvent is present, e.g., a neat reaction substrate or liquid molten solids.

In general, the particular balance of properties such as surface area, pore volume, pore diameter, amino-functionalization, chemical stability and mechanical strength, in combination with low cost provide a superior material for biocatalytic applications.

A further feature of the amino-functionalised CPS material is the ability to facilitate the forming of a covalent linkage between the immobilized enzyme and the amino-functionalised coating on the CPS support material. The presence of a covalent linkage can be particularly beneficial in reaction media that contain components that would otherwise leach the enzyme from the amino-functionalised support material. Furthermore, the covalent linkage may be installed without any loss of enzyme activity. This is an important advantage when compared with support materials that do not contain an amino-functionalized surface coating.

Biocatalysts for Organic Synthesis

In a first aspect, the present invention relates to a biocatalyst for organic synthesis, comprising:

a. a controlled porosity silica (CPS) as support material, having a pore diameter from about 20 to about 100 nm;
wherein the support material comprises an amino-functionalized surface; and
b. one or more catalytically active enzyme(s) immobilized to the amino-functionalized surface by a covalent linker comprising a bond selected from amino, amide, ester, ether, imidoamide, imidothioamide, thioether, thioester and thioamide.

In a second aspect, the present invention relates to a biocatalyst for organic synthesis, comprising:

a. a controlled porosity silica (CPS) as support material, having a pore diameter from about 20 to about 100 nm;
wherein the support material comprises an amino-functionalized surface; and
b. one or more catalytically active enzyme(s) immobilized to the surface via non-covalent interactions.

In a third aspect, the present invention relates to a biocatalyst for organic synthesis, comprising:

a. a controlled porosity silica (CPS) as support material, having a pore diameter from about 20 to about 100 nm;
wherein the support material surface comprises at least two different coatings, of which at least one provides an amino functionalized surface; and
b. one or more catalytically active enzyme(s) immobilized on the surface, optionally by a covalent linker comprising a bond selected from amino, amide, ester, ether, thioether, imidoamide, imidothioamide, thioester and thioamide.

In a fourth aspect, the present invention relates to a biocatalyst for organic synthesis, comprising a. a controlled porosity silica (CPS) as support material, having a pore diameter from about 20 to about 100 nm;

wherein the support material comprises an amino-functionalized surface; and b. one or more catalytically active enzyme(s) immobilized to the amino-functionalized surface, optionally by a covalent linker comprising a bond selected from amino, amide, ester, ether, thioether, imidoamide, imidothioamide, thioester and thioamide, wherein the enzyme(s) is/are selected from list (A), preferably from list (B) disclosed below.

Preferably, the covalent linker in the first, third and fourth aspects, when present, comprises a bond selected from the group consisting of amino, amide, ester, ether, thioether, thioester and thioamide.

More preferably, the covalent linker in the first, third and fourth aspects, when present, comprises a bond selected from the group consisting of amino, amide, thioether, thioester and thioamide. Even more preferably, the covalent linker in the first, third and fourth aspects, when present, comprises a bond selected from the group of amino, amide, or thioamide. Yet more preferably, the covalent linker, in the first, third and fourth aspects, when present, comprises a bond selected from the group consisting of amino, amide and imidoamide.

Most preferably, the covalent linker in the first, third and fourth aspects immobilizing the enzymes(s) to the surface comprises a bond selected from amino and amide bonds, when present.

Without being bound by theory, the covalent linker between the amino-functionalized surface and the enzyme contains (i) a bond formed in the reaction between the amino-functionalized surface and a functional group on the cross-linking reagent used to form the covalent linker, (ii) a bond formed in the reaction between reactive functional groups in the enzyme and functional groups on the cross-linking reagent, and (iii) optionally, any spacer moiety that was present between the functional groups of the cross-linking agent, which contains preferably 3-20 atoms comprising any combination of C, N, H and O. The bond referred to as (i) preferably comprises a bond selected from the group consisting of amino, amide and imidoamide. The bond referred to as (ii) may comprise a bond selected from the group consisting of amino, amide, ester, ether, thioether, imidoamide, imidothioamide, thioester and thioamide.

Optionally, the immobilized enzymes may be intermolecularly covalently linked by a linker comprising a bond selected from amino, amide, ester, ether, thioester, imidoamide, imidothioamide, thioether and thioamide. These bonds are formed in the reaction between reactive functional groups in the enzyme and functional groups on the cross-linking reagent. The intermolecular linkers may optionally comprise a spacer moiety that was present between the functional groups of the cross-linking agent, which contains preferably 3-20 atoms comprising any combination of C, N, H and O.

The amino-functionalized surface comprises primary, secondary or tertiary amines.

The particulars and preferred features of the biocatalyst are set out below.

Support Material

The support material according to the first aspect of the invention is controlled porosity silica (CPS), which is available at several ranges of pore diameters. Untreated silica ($SiO_2$) surface is covered by hydroxyl groups (—OH), whereas the support material of the present invention is amino functionalized as explained in more detail below.

The controlled pore silica materials ideal for the invention have been specifically designed for use as catalyst supports where mechanical properties such as crush strength, attrition and abrasion resistance are a necessary feature of the material for performance as catalyst supports. The controlled pore silica materials, which are chemically and thermally stable, also provide precisely controlled pore diameters and pore diameter distributions. Particle sizes and particle size ranges can be tailored and optimized for different industrial reactor types. For example, they may be deployed in batch or continuous stirred tank reactors (CSTR) as slurry catalysts or slurry bubble columns or fixed bed reactors or known variations thereof. This is an advantage when compared to controlled pore glass materials which are known to be brittle and prone to abrasion or attrition when stirred in a batch reactor or a CSTR.

A suitable pore diameter is a crucial feature of the support. Suitably sized pores provide a favorable microenvironment without complications due to steric hindrance. The pore structure results in low solution flow resistance and facilitates the mass transfer of reactants and products throughout the material. The rigid non-caged structure of CPS provides a rugged, noncompressible medium suitable for high throughput reactor designs and linear scale up at high flow rates. The material displays limited swelling in solvents and is chemically and dimensionally stable in most organic media and aqueous environments at pH below 10.

The physical properties of the controlled porosity silica make it suitable for the immobilization of enzymes onto the surface of the carrier with high enzyme loadings. In general, controlled pore silica materials that are suitable for the invention have pore diameters from about 20 nm to about 100 nm, preferably from about 20 to about 60 nm more preferably from about 30 to about 50 nm. Preferably, the surface area is from about 50 $m^2/g$ to about 200 $m^2/g$ (preferably greater than about 60 $m^2/g$, such as greater than about 70 $m^2/g$). Also preferably, the pore volume is from about 0.5 mL/g to about 2.0 mL/g (more preferably at least about 0.6 mL/g, even more preferably at least about 0.7 mL/g, and most preferably from about 0.8 mL/g to about 1.5 mL/g). These properties allow the immobilization of enzymes with high loadings onto the surface of the carrier. Preferably, the pore diameter of the support material is from about 20 to about 60 nm and the surface area is from about 50 $m^2/g$ to about 200 $m^2/g$. Even more preferably, the support material has a pore diameter from about 20 to about 60 nm, a surface area from about 50 $m^2/g$ to about 200 $m^2/g$ and a pore volume of from about 0.5 mL/g to about 2.0 mL/g. Most preferably, the support material has a pore diameter from 20 to 60 nm, a surface area from 50 $m^2/g$ to 200 $m^2/g$ and a pore volume from 0.5 mL/g to 2.0 mL/g. The ranges disclosed herein include the endpoints.

A CPS support exhibits an enzyme loading capacity that is inversely related to its pore diameter. Thus, a CPS support of a large pore diameter cannot be loaded with as much protein as a CPS support of a smaller pore diameter, which is largely due to the inverse relationship between pore diameter and surface area (i.e., a lower available surface area for enzyme immobilization).

The preferred particle size is dependent on the type of reactor deployed for the use of the immobilized biocatalyst. For example, smaller particles sizes, e.g., 75-150 μm are well suited for the deployment of a batch or a continuous stirred tank reactor where the immobilized biocatalyst operates as a catalyst slurry in the reactor. For deployment in a fixed bed reactor, the preferred particle size is dependent on the chemical reaction and the conditions within the reactor. Smaller particles e.g., 75-150 μm are preferred for liquid phase fixed bed reactions whereas larger particle sizes can be deployed for certain other liquid phase reactions and reactions where a gas and a liquid are deployed together within the fixed bed reactor, e.g., particle sizes greater than 200 μm, and preferably greater than 500 μm.

Certain types of the preferred porous silica materials are available commercially. For example, the CARiACT™ class of controlled pore silicas is available from Fuji Silysia Chemical Ltd (website: fujisilysia.com/products/cariact/). These inorganic porous silicas can be produced with different surface areas and pore diameters. It has surprisingly been found that these materials are advantageous for the immobilization of enzymes with high enzyme loadings onto the surface of the carrier. The properties of Fuji CAMiACT Q-30 and Q-50 make these materials particularly advantageous. The materials Fuji CARiACT Q-20C, Q30C and Q40C are also suitable. According to the manufacturer, the particles have the following characteristics:

| Product | surface area $m^2/g$ | particle sizes available | pore volume $cm^3/g$ | pore diameter nm |
|---|---|---|---|---|
| Q-30 | 100 | 75-150 μm | 1.00 | 30 |
| | | 75-500 μm | | |
| | | 1.18-2.36 mm | | |
| | | 1.70-4.00 mm | | |
| Q-50 | 80 | 75-150 μm | 1.00 | 50 |
| | | 75-500 μm | | |
| | | 1.18-2.36 mm | | |
| | | 1.70-4.00 mm | | |
| Q-20C | 140 | 1.18-2.36 mm | 0.80 | 20 |
| | | 1.70-4.00 mm | | |
| Q-30C | 95 | 1.18-2.36 mm | 0.80 | 30 |
| | | 1.70-4.00 mm | | |
| Q-40C | 70 | 1.18-2.36 mm | 0.80 | 40 |
| | | 1.70-4.00 mm | | |

Another suitable commercially available material is Ecovyst E30. The particles have the following characteristics:

| Material | surface area $m^2/g$ | particle diameter μm | pore volume $cm^3/g$ | pore diameter nm |
|---|---|---|---|---|
| E30 | 114 | 70-220 | 0.93 | 32.6 |

Controlled porosity silicas of the invention can be prepared in accordance with the methods described in JPH0930809A and JP2020001936. Both methods describe the details of the production methods that provide sufficient control to modify the properties of the silica to produce controlled porosity silicas with the necessary balance of properties such as the previously specified surface areas, pore volumes, pore diameters and particle sizes. In addition, these production methods produce controlled porosity silicas with the necessary mechanical strength to enable the features of this invention. In general, two raw materials, sodium silicate and a mineral acid such as sulphuric acid, are used together in a solution process to generate monomeric silicic acid. Monomeric silicic acid polymerizes to generate primary silica particles, referred to as silica sol. These primary particles then aggregate together to form a three-dimensional porous structure. The reaction conditions that enable the growth of the primary particles and conditions to dry the product are used to control and to modify physical properties such as surface area, pore diameter and pore volume.

Finally, it should be understood that CPS in the present context is distinct from siliceous mesocellular foams (MCFs) known in the literature. MCFs possess ordered 3D cage-like structures with spherical cavities having diameters of 20-40 nm, interconnected by pores of around 10 nm in size, which are lower than desired for the immobilisation of enzymes. In contrast, CPS is not a caged structure. In the context of MCF materials, literature often uses the terms pore size to define the diameter of the cage and pore window to define the cage entrance diameter (or pore diameter) where the window size is typically smaller than the pore size. Due to the cage-like structure and lower window sizes, the surface areas ($m^2/g$) of MCF materials are typically significantly higher than that of CPS (over 200 $m^2/g$). MCF is currently not commercially available at industrial scale and is prohibitively expensive for industrial applications, so it is not a practically viable alternative to CPS.

Controlled pore silicas are also distinct from hollow microsphere silicas described in the literature. WO 2013/078551 describes hollow microsphere silicas as microcapsules comprising a silica shell having a thickness of from about 50 nm to about 500 μm, said shell surrounding a hollow capsule having a diameter from about 0.1 μm to about 1500 μm, and having a density of about 0.001 $g/cm^3$ to about 1.0 $g/cm^3$. The hollow feature of these materials is shown clearly in FIGS. 2-5 of WO 2013/078551. These materials are core/shell/functional surface type reservoirs or microcapsules, comprising a core (gaseous or hollow) surrounded by a shell (generally solid) composed essentially of one or more silica-based materials and capped with a functional surface with affinity or adhesion to the matrix of plastics or composites or rubbers or textiles. The microcapsules are designed to be introduced into plastics, composites, rubbers and textiles products in their processing stage. Gaseous or hollow microcapsules are dispersed throughout or partially in plastics, composites, rubbers and textiles products as a density-reducing additive to reduce the density of the final products. Whereas the hollow sphere microcapsules of WO 2013/078551 are designed as a density reducing additive that can provide a material benefit to a formulated product, the controlled pore silica materials of the invention have been specifically designed for use as catalyst supports where mechanical properties such as crush strength, attrition and abrasion resistance are a necessary feature of the material for performance as catalyst. Such properties would not be provided by such low-density, hollow sphere supports with an inherently low crush strength. The controlled pore silicas of the invention are not hollow and comprise a three-dimensional silica structure comprising precisely controlled pore diameters and pore diameter distributions throughout the entire solid well suited to the synthesis of efficient and robust biocatalysts.

Immobilized Enzyme(s)

In principle, any enzyme of interest may be immobilized. Preferably, the enzyme is an esterase, a transferase, an oxidoreductase, a hydrolase, a ligase, an isomerase or a lyase.

The immobilized enzyme(s) may be selected from enzymes on list (A) consisting of items 1-62 in the following Table A and their enzymatically active sequence variants, preferably variants having similar enzymatic activity, and most preferably substantially the same enzymatic activity.

It is well known that the amino-acid sequence of an enzyme can be varied considerably without significantly affecting the enzymatic activity. For instance, artificial sequences such as His-tags can be added to enable metal chelation. In other instances, residues that are not critical to enzymatic activity can be modified to improve properties (such as stability or efficiency of production) or simply to provide an alternative sequence to circumvent patent protection. In some cases, the enzyme sequence can be truncated to produce a more compact enzyme by dispensing with parts of the enzyme not critical to enzyme activity. Thus, enzymatically active sequence variants of the enzymes identified in Table A can also be used and are therefore encompassed by list (A).

TABLE A preferred immobilized enzymes

| # | Enzyme name (organism) | Uniprot id/other ref. | EC Number |
|---|---|---|---|
| 1 | Lipase (*Thermomyces lanuginosus*) | O59952 | 3.1.1.3 |
| 2 | Lipase CALB (*Pseudozyma antarctica*) | P41365 | 3.1.1.3 |
| 3 | Sucrose phosphorylase (*Bifidobacterium adolescentis*) | A0ZZH6 | 2.4.1.7 |
| 4 | Isopropanol dehydrogenase (*Thermoanaerobacter brockii*) | P14941 | 1.1.1.80 |
| 5 | Fructose-6-phosphate aldolase (*Escherichia coli*) | P78055 | 4.1.2.- |
| 6 | Phenylalanine ammonia-lyase (*Petroselinum crispum*) | P24481 | 4.3.1.24 |
| 7 | Xylose isomerase (*Thermotoga neapolitana*) | P45687 | 5.3.1.5 |
| 8 | Triosephosphate isomerase (*Escherichia coli*) | P0A858 | 5.3.1.1 |
| 9 | Glucose oxidase (*Aspergillus niger*) | P13006 | 1.1.3.4 |
| 10 | Cholesterol oxidase (*Streptomyces* sp) | P12676 | 1.1.3.6 |
| 11 | Galactose Oxidase (*Gibberella zeae*) | P0CS93 | 1.1.3.9 |
| 12 | Choline oxidase (*Arthrobacter globiformis*) | Q7X2H8 | 1.1.3.17 |
| 13 | Alcohol oxidase (*Candida boidinii*) | Q00922 | 1.1.3.13 |
| 14 | L-alanine dehydrogemase (*Bacillus subtilis*) | Q08352 | 1.4.1.1 |
| 15 | Alcohol dehydrogenase (*Saccharomyces cerevisia*) | P00330 | 1.1.1.1 |
| 16 | Glucose-6-phosphate Dehydrogenase (*Leuconostoc mesenteroides*) | P11411 | 1.1.1.363 |
| 17 | Glycerol dehydrogenase (*Citrobacter freundii*) | P45511 | 1.1.1.6 |
| 18 | Sucrose phosphorylase (*Leuconostoc mesenteroides*) | Q59495 | 2.4.1.7 |
| 19 | Formate dehydrogenase (*Candida boidinii*) | O13437 | 1.17.1.9 |
| 20 | Phosphonate dehydrogenase (*Pseudomonas stutzeri*) | O69054 | 1.20.1.1 |
| 21 | Glucose dehydrogenase (*Bacillus megaterium*) | P39484 | 1.1.1.47 |
| 22 | Glucose dehydrogenase (*Thermoplasma acidophilum*) | P13203 | 1.1.1.47 |
| 23 | Laccase (*Bacillus subtilis*) | P07788 | 1.10.3.2 |
| 24 | Alpha-galactosidase (*Thermotoga maritima*) | G4FEF4 | 3.2.1.22 |
| 25 | Beta-galactosidase (*Bifidobacterium adolecentis*) | A1A399 | 3.2.1.23 |
| 26 | Beta-galactosidase (*Aspergillus oryzae*) | Q2UCU3 | 3.2.1.24 |
| 27 | Endo-1,4-beta-xylanase (*Aspergillus oryzae*) | Q9HFA4 | 3.2.1.8 |
| 28 | Alpha-amylase (*Bacillus licheniformis*) | P06278 | 3.2.1.1 |
| 29 | Xylose isomerase (*Streptomyces rubiginosus*) | P24300 | 5.3.1.5 |
| 30 | Phosphoglucomutase (*Thermococcus kodakarensis*) | Q68BJ6 | 5.4.2.2 |
| 31 | Glucose-6-phosphate isomerase (*Thermotoga maritima*) | Q9X1A5 | 5.3.1.9 |
| 32 | Cellulase (*Acetivibrio thermocellus*) | P10477 | 3.2.1.4 |
| 33 | Cellulase (*Thermoanaerobacterium*) | A0A0U4EBH5 | 3.2.1.4 |
| 34 | Acid phosphatase (*Salmonella typhimurium*) | P26976 | 3.1.3.2 |
| 35 | Polyphosphate-nucleotide phosphotransferase (*Erysipelotrichaceae bacterium*) | A0A3D5XRJ5 | 2.7.4.1 |
| 36 | Amylosucrase (*Neisseria polysaccharea*) | Q9ZEU2 | 2.4.1.4 |
| 37 | Glutamate-cysteine ligase (*Escherichia coli*) | P0A6W9 | 6.3.2.2 |
| 38 | Glycerol kinase (*Escherichia coli*) | P0A6F3 | 2.7.1.30 |
| 39 | Aminotransferase (*Chromobacterium violaceum*) | Q7NWG4 | 2.6.1.62 |
| 40 | P450 (*Bacillus megaterium*) | P14779 | 1.6.2.4 |
| 41 | Acid sugar phosphatase (*Bacillus subtilis*) | O32125 | 3.1.3.5 |
| 42 | D-xylonate dehydratase (*Caulobacter vibrioides*) | Q9A9Z2 | 4.2.1.82 |
| 43 | UDP-glucose 4-epimerase (*Chloroflexi bacterium*) | A0A7C4N917 | 5.1.3.2 |
| 44 | Alkylhalidase (*Aspergillus niger*) | A2QL40 | 3.8.1.1 |
| 45 | D-amino acid oxidase (*Sus scrofa*) | P00371 | 1.4.3.3 |
| 46 | Adenylate kinase (*Homo sapiens*) | P13569 | 2.7.4.3 |
| 47 | Alanine racemase (*Mycobacterium tuberculosis*) | P9WQA9 | 5.1.1.1 |
| 48 | Haloalkane dehalogenase (*Xanthobacter autrophicus*) | P22643 | 3.8.1.5 |
| 49 | Aromatic peroxygenase (*Agrocybe aegerita*) | B9W4V6 | 1.11.2.1 |
| 50 | Acetase kinase (*Bacillus subtilis*) | P37877 | 2.7.2.1 |
| 51 | Fatty acid peroxygenase (*Bacillus subtilis*) | O31440 | 1.11.2.4 |
| 52 | Glycerol dehydratase (*Citrobacter freundii*) | P45514 | 4.2.1.30 |
| 53 | Carbonic anhydrase (*Gallus gallus*) | P07630 | 4.2.1.1 |
| 54 | Catalase (*Bacillus subtilis*) | P94377 | 1.11.1.6 |
| 55 | Fructokinase (*Bacillus subtilis*) | O05510 | 2.7.1.4 |
| 56 | NAD(P)H oxidase (*Sus scrofa*) | Q8HZK2 | 1.6.3.1 |
| 57 | NAD(P)H oxidase (*Thermococcus kodakarensis*) | Q5JGP4 | 1.6.3.2 |
| 58 | Hexokinase (*Saccharomyces cerevisiae*) | P04806 | 2.7.1.1 |
| 59 | Amidase (*Arabidopsis thaliana*) | Q9FR37 | 3.5.1.4 |
| 60 | Aminotransferase (*Arthrobacter* species) | F7J696 | 2.6.1.18 |
| 61 | Amyloglucosidase 300L (*Aspergillus niger*) | Ref 1 | 3.2.1.3 |
| 62 | Aminotransferase ATA_633 (*Arthrobacter* species) | Ref 2 | 2.6.1.26 |

Ref 1: Global Substance Registration System Ver 3.0.3 UNII record A370TYK9KO.

Ref 2: Cuetos A et al. (2016) Angew Chem Int Ed 2016, 55: 3144-3147.

The immobilized enzyme(s) is/are preferably selected from list (B) consisting of: *Thermomyces lanuginosus* lipase (TLL, #1 in Table A), *Candida antarctica* lipase (CalB, #2 in Table A), *Bifidobacterium adolescentis* sucrose phosphorylase (SucP, #3 in Table A), *Thermoanaerobacter brockii* secondary alcohol dehydrogenase (TbSADH, #4 in Table A), *Arthrobacter* species amine transaminase (ATA, #60 in Table A), *Leuconostoc mesenteroides* glycosyl transferase (GT, #18 in Table A), amyloglucosidase from *Aspergillus niger* (#61 in Table A), and aminotransferase (*Arthrobacter* species) (#62 in Table A); and their enzymatically active sequence variants, preferably variants having similar enzymatic activity, and most preferably substantially same enzymatic activity.

The enzyme activity relevant in the context of lists (A) and (B) is indicated in Table A by the "EC Number" column, which refers to the numerical classification scheme of the Enzyme Commission, which categorizes enzymes by their catalyzed reactions.

The Uniprot id-column in table (A) refers to entries on the public Uniprot database (website: uniprot.org), as of 1 Dec. 2021. Preferably, each selected enzyme of list (A) or list (B) has at least 70% sequence identity to the sequence according to the database entry identified by the "Uniprot id" indicated in Table A, more preferably at least 80%, even more preferably at least 90%, still more preferably at least 95% and most preferably complete sequence identity.

In some embodiments, the enzyme comprises a metal affinity tag such as a polyhistidine tag (His-tag of 2-8 consecutive histidines, preferably 6), HQ-tag (Godat et al. Promega Notes Number 91 p. 17-20), MAT Tag (Watson et al. BioTechniques Vol 42 No 6, 2007, p. 768) or any other suitable tags known in the art, to facilitate immobilization via metal chelation.

Amino-Functionalized Surface

The amino-functionalized surface may comprise a structure of formula (I), (II) or (III):

(I)

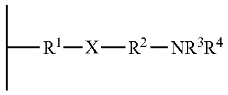

(II)

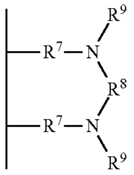

(III)

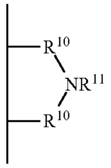

wherein $R^1$ is $C_{1-6}$ alkanediyl; and wherein $R^1$ provides a covalent attachment to the silica surface (the vertical line on the left);

X is a bond (i.e., X is absent) or is a phenyl ring;

$R^2$ is $C_{1-6}$ alkanediyl;

$R^3$ is W;

$R^4$ is W or is selected from the group consisting of $C_{1-10}$ alkyl, $C_{5-7}$ cycloalkyl, phenyl, phenyl-$C_{1-6}$-alkyl, amino-$C_{2-8}$ alkyl, N-(phenyl)amino-$C_{2-8}$ alkyl and N-(phenyl-$C_{1-6}$-alkyl)amino-$C_{2-8}$ alkyl, and aminocarbonyl; and wherein phenyl, at each instance, is optionally substituted with one or more substituents $C_{1-4}$ alkyl;

or $R^3$ and $R^4$, together with the nitrogen atom to which they are attached, combine to form a 5- to 7-membered heterocyclic ring which may contain one or more unsaturated bonds and which may contain one more additional heteroatoms, on which a covalent linker comprising a bond selected from amino, amide, and imidoamide is optionally attached, wherein a catalytically active enzyme also is attached to the linker;

or $R^3$ and $R^4$ together form $=CR^5R^6$, wherein $R^5$ and $R^6$ are each independently $C_{1-4}$ alkyl;

Each $R^7$ is independently $C_{1-6}$ alkanediyl; and wherein $R^7$ provides a covalent attachment to the silica surface (the vertical line on the left);

$R^8$ is $C_{1-3}$ alkanediyl;

Each $R^9$ is independently W or is selected from the group consisting of $C_{1-4}$ alkyl and hydroxy-$C_{1-4}$ alkyl;

Each $R^{10}$ is independently $C_{1-6}$ alkanediyl; and wherein $R^{10}$ provides a covalent attachment to the silica surface (the vertical line on the left);

$R^{11}$ is W or is selected from the group consisting of $C_{1-10}$ alkyl, $C_{5-7}$ cycloalkyl, phenyl, phenyl-$C_{1-6}$-alkyl, amino-$C_{2-8}$ alkyl, N-(phenyl)amino-$C_{2-8}$ alkyl and N-(phenyl-$C_{1-6}$-alkyl)amino-$C_{2-8}$ alkyl, and aminocarbonyl; and wherein phenyl, at each instance, is optionally substituted with one or more substituents $C_{1-4}$ alkyl; and each W is independently hydrogen or a covalent linker comprising a bond selected from amino, amide, and imidoamide, wherein a catalytically active enzyme is also attached to the linker.

In some embodiments, the amino-functionalized surface comprises a structure of formula (I), as defined above, in combination with a structure of formula (IV):

(IV)

wherein $R^{12}$ is selected from $C_{1-12}$ alkyl and amino-$C_{1-6}$ alkyl.

Preferably, the amino functional groups in the surface are not part of an aromatic heterocyclic ring, more preferably not any heterocyclic ring.

Preferably, the surface does not contain any functional groups that may chelate a metal ion apart from the amino groups.

More preferably, the surface comprises amino-functionalized aliphatic moieties.

In some instances, it is beneficial to have at least two different coating on the CPS material (of which at least one providing the amino-functionalization). The presence of two different coatings can provide, for certain enzymes, a better balance of properties suited to the said certain enzyme, leading to a more efficient biocatalyst. For example, a certain enzyme may prefer a coating which is more hydrophobic in nature and may also benefit from the presence of an amino group, and additionally a metal ion. Such a situation can be accommodated by the presence of at least two coatings, one providing the amino-functionalization and the other providing a hydrophobic coating. The hydrophobic coating may comprise alkyl moieties and/or aromatic moieties. Preferably, the hydrophobic coating comprises $C_{1-12}$ alkyl groups, preferably $C_{1-6}$alkyl groups and/or a phenyl group.

For instance, one coating may contain an aliphatic chain, or a phenyl group, providing a hydrophobic environment, and the second may contain an amino-functionalized group, which may further accommodate a metal ion. The relative proportions of the two coatings on the surface can be controlled and optimized to maximize the efficiency of the biocatalyst. The relative amount of the two coatings may be in the range of 9:1 to 1:9 on weight basis, preferably 5:1 to 1:5, more preferably 2:1 to 1:2, most preferably 1:1.

Furthermore, the presence of two coatings can benefit the situation where a covalent linkage is preferred between the enzyme and the surface of the CPS material. The presence of two coatings can tailor the surface with two coatings that can a) provide a chemical group that is preferred by the enzyme, for example a hydrophobic group such as an aliphatic chain or a phenyl group, and b) provide an amino-functionalized group to enable a covalent linkage between the enzyme and the CPS surface.

As used herein, the term "$C_{1-6}$ alkanediyl" refers to a straight or branched divalent group having from 1 to 6 carbon atoms. Examples of $C_{1-6}$ alkanediyl include methanediyl, ethanediyl, 1,3-propanediyl and 2,2-dimethyl-1,4-butanediyl.

As used herein, the term "$C_{1-10}$ alkyl" refers to a straight or branched alkyl group having from 1 to 10 carbon atoms, and the term "$C_{1-4}$ alkyl" refers to a straight or branched alkyl group having from 1 to 4 carbon atoms. Examples of $C_{1-4}$ alkyl include methyl, ethyl, n-propyl, isopropyl, n-butyl, isobutyl, sec-butyl and tert-butyl.

As used herein, the term "$C_{5-7}$ cycloalkyl" refers to a monocyclic saturated hydrocarbon ring having from 5 to 7 carbon atoms. Examples of $C_{5-7}$ cycloalkyl include cyclopentyl, cyclohexyl and cycloheptyl.

As used herein, the term "hydroxy-$C_{1-4}$ alkyl" refers to a $C_{1-4}$ alkyl group wherein one of the hydrogen atoms is replaced with a hydroxy group.

As used herein, the term "phenyl-$C_{1-6}$ alkyl" refers to a $C_{1-4}$ alkyl group wherein one of the hydrogen atoms is replaced with a phenyl group.

As used herein, the term "amino-$C_{2-8}$ alkyl" refers to a $C_{2-8}$ alkyl group wherein one of the hydrogen atoms is replaced with amino.

The term "amino" refers to primary, secondary and tertiary amines.

The term "aminocarbonyl" refers to a group —C(═O)$NH_2$.

As used herein, the terms "N-(phenyl)amino-$C_{2-8}$ alkyl" and "N-(phenyl-$C_{1-6}$-alkyl)amino-$C_{2-8}$ alkyl" refer to an amino-$C_{2-8}$ alkyl group wherein one of the hydrogen atoms on the amino group is replaced with a phenyl or a phenyl-$C_{1-6}$ alkyl group, respectively.

Preferably, the amino-functionalized surface comprises any of the following structures, wherein each W is hydrogen or a covalent linker comprising a bond selected from amino, amide and imidoamide, wherein a catalytically active enzyme is also attached to the linker:

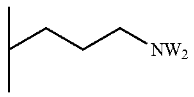

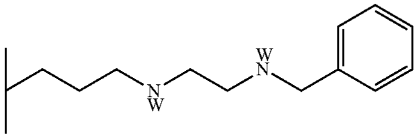

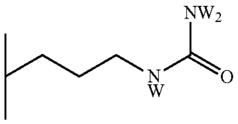

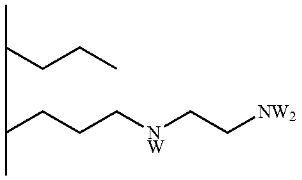

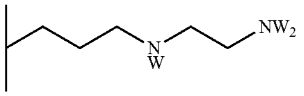

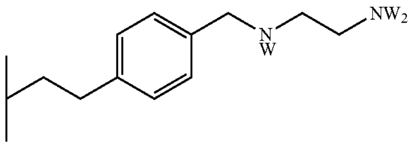

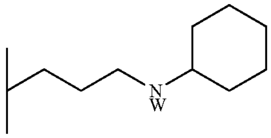

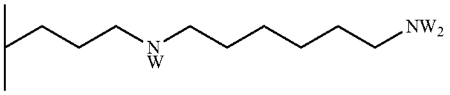

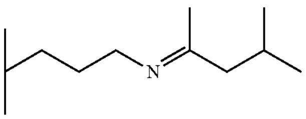

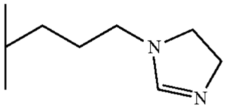

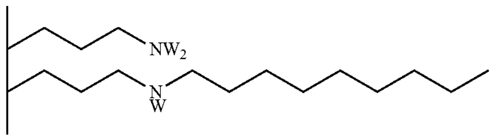

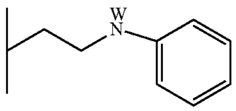

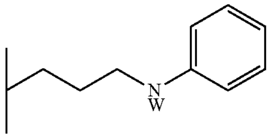

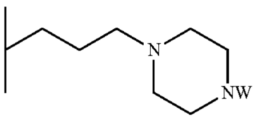

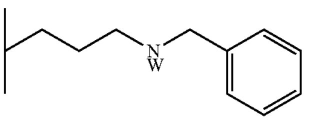

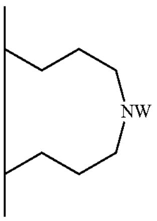

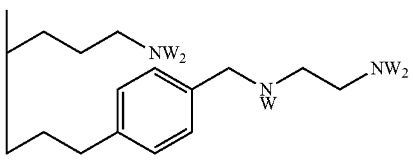

-continued

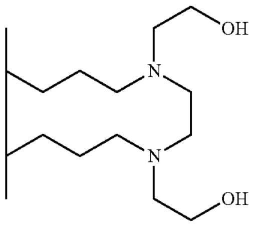

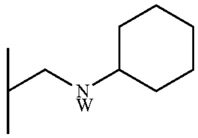

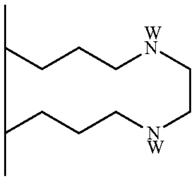

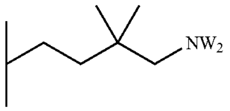

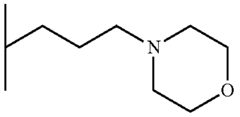

In some embodiments, the amino-functionalized surface comprises structure (I'):

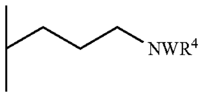

(I')

wherein $R^4$ is W or is selected from the group consisting of phenyl, phenyl-$C_{1-6}$-alkyl, amino-$C_{2-8}$ alkyl, N-(phenyl)amino-$C_{2-8}$ alkyl and N-(phenyl-$C_{1-6}$-alkyl)amino-$C_{2-8}$ alkyl, and wherein phenyl, at each instance, is optionally substituted with one or more substituents $C_{1-4}$ alkyl; and W is hydrogen or a covalent linker comprising a bond selected from amino, amide and imidoamide, wherein a catalytically active enzyme is also attached to the linker;

or wherein the amino-functionalized surface comprises structure (I"):

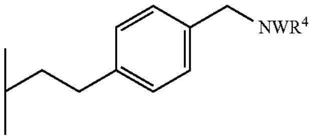

(I")

wherein $R^4$ is W or is selected from the group consisting of amino-$C_{2-8}$ alkyl, N-(phenyl)amino-$C_{2-8}$ alkyl and N-(phenyl-$C_{1-6}$-alkyl)amino-$C_{2-8}$ alkyl, and wherein phenyl, at each instance, is optionally substituted with one or more substituents $C_{1-4}$ alkyl; and W is hydrogen or a covalent linker comprising a bond selected from amino, amide and imidoamide, wherein a catalytically active enzyme is also attached to the linker.

In certain preferred embodiments, the amino-functionalized surface comprises structure I' wherein $R^4$ is W or is selected from the group consisting of phenyl, benzyl, amino-$C_{2-6}$ alkyl, N-(phenyl)amino-$C_{2-6}$ alkyl and N-(benzyl)amino-$C_{2-6}$ alkyl; or the amino-functionalized surface comprises structure I" wherein $R^4$ is W.

More preferably, the amino-functionalized surface comprises any of the following structures, wherein each W is hydrogen or a covalent linker comprising a bond selected from amino, amide and imidoamide, wherein a catalytically active enzyme is also attached to the linker:

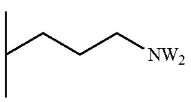

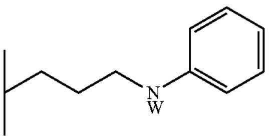

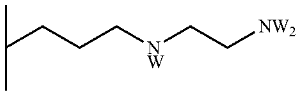

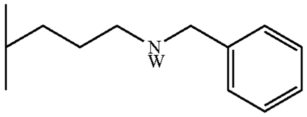

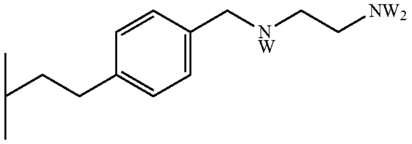

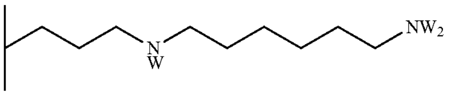

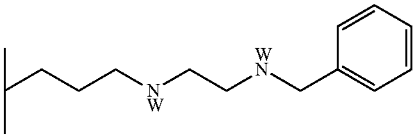.

Most preferably, the amino-functionalized surface comprises any of the following structures, wherein each W is hydrogen or a covalent linker comprising a bond selected from amino, amide and imidoamide, wherein a catalytically active enzyme is also attached to the linker:

(1)

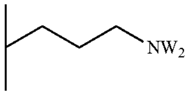

propylamine (2)

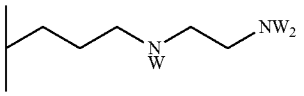

propylNH-N-aminoethyl (3)

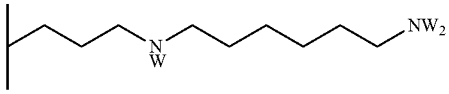

propyl-NH-N-aminohexyl (LCAA)

-continued (4)

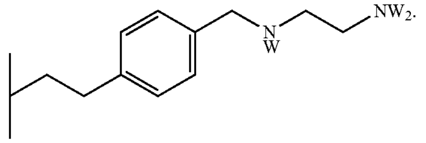

phenethyl-methyl-NH-N-aminoethyl

For avoidance of any doubt, it should be understood that the above names for structures (1)-(4) are derived from the situation where W=H, but the structures nonetheless also encompass the situation where W is a covalent linker comprising a bond selected from amino, amide and imidoamide, wherein a catalytically active enzyme is also attached to the linker Enzyme Immobilization In preferred embodiments of the third and fourth aspects, the enzyme(s) is/are immobilized to the surface by a covalent linker comprising a bond selected from amino, amide and imidoamide, although non-covalent immobilization is also an option.

In preferred embodiments of the first, third and fourth aspects, the enzyme(s) is/are immobilized to the surface by a covalent linker comprising a bond selected from amino, amide and imidoamide, and prior to formation of the bond, the enzyme(s) had been immobilized to the surface via non-covalent interactions, preferably via an interaction mediated by a chelated metal ion. Without being bound by theory, immobilization after non-covalent binding may allow for more uniform cross-link formation between the CPS support surface and the enzyme, resulting in improved retention of activity. In other embodiments, the initial immobilization is through covalent linkers, optionally additionally followed by intermolecular cross-linking.

In preferred embodiments of the second, third and fourth aspects, the enzyme(s) is/are immobilized to the surface non-covalently via an interaction mediated by a chelated metal ion.

The chelated metal ion referred to above may be selected from $Ni^{2+}$, $Cu^{2+}$, $Mg^{2+}$, $Fe^{3+}$ or $Zn^{2+}$. Preferably, the metal ion is a $Zn^{2+}$ ion. Such $Zn^{2+}$ ion mediated interaction provides superior results for certain enzymes such as CalB and TbSADH (see Example 2).

In certain embodiments of the first, second, third or fourth aspects, the immobilized enzyme(s) are intermolecularly covalently linked by a linker comprising a bond selected from amino, amide, ester, ether, thioether, imidoamide, imidothioamide, thioester and thioamide.

Preferably, the covalent linker between the surface and the enzyme(s), when present, does not comprise imine bonds, which can be susceptible to cleavage by hydrolysis. Preferably, the intermolecular covalent linker, when present, does not comprise imine bonds. Preferably, the covalent linker, when present, comprises a bridge containing between 3 and 20 atoms comprising any combination of C, H, N and O.

In some embodiments, the enzyme comprises a metal affinity tag such as a polyhistidine tag (His-tag of 2-8 consecutive histidines, preferably 6), HQ-tag (HQHQHQ), MAT Tag (HNHRHKH) or any other suitable tags known in the art, to facilitate immobilization via metal chelation. It should be noted that many enzymes of industrial relevance can be immobilized via metal chelation even without an affinity tag, due to innate metal-chelating properties of the enzyme. An advantage of immobilization via metal chelation using an affinity tag, however, is selective enzyme binding when compared to physical adsorption, and in addition the steric orientation of the immobilized enzyme may be more uniform compared to the situation where the immobilization occurs for example via non-specific physical adsorption. An affinity tag may also improve activity after immobilization by driving the immobilization in a controlled position allowing better and/or more consistent access to the active site. On the other hand, initial immobilization through covalent linkers can also apply as it can afford a simplified manufacturing process since the step of non-covalent immobilization can be omitted.

Covalent cross-linking (between different enzyme molecules and/or between enzyme molecules and the amino groups of the amino-functionalized surface) has certain advantages. The cross-linking allows better retention of enzyme activity in industrial flow conditions, and the possibility to recycle and reuse the catalyst in batch operations.

Suitable cross-linking reagents for formation of the covalent cross-links are disclosed below.

Cross-Linking Reagents

Various covalent cross-linking strategies as applied to amino functional groups and enzymes are known in the field of protein chemistry. See for example, the Crosslinking Technical Handbook published by Thermo Scientific incorporated herein by reference (website: tools.thermofisher-.com/content/sfs/brochures/1602163-Crosslinking-Reagents-Handbook.pdf).

An effective cross-linking reagent that links an enzyme to the amino-functionalized support surface will require at least two (preferably no more than two) reactive groups separated by a linker. An effective cross-linking reagent needs to contain at least a first reactive group that can react with the amino functional group attached to the CPS surface to form a stable covalent bond. Additionally, the cross-linking reagent needs to contain at least a second reactive group that can react with a functional group that is present on the enzyme structure to form a stable covalent bond, thus creating a covalent link between the enzyme and the support surface. Alternatively, the reagent can contain at least two reactive groups that each can react with a functional group that is present on the enzyme structure to form a stable covalent bond, thus creating an intermolecular covalent link between enzyme molecules.

Functional groups on enzymes that are amenable to cross-linking include amine groups, carboxylate groups, thiol (sulfhydryl) and hydroxy groups. With an appropriate selection of a cross-linking reagent, these functional groups can readily form covalent bonds such as amino, amide, ester, ether, thioether, imidoamide, imidothioamide, thioester and thioamide. As a specific example, in the case of an epoxide cross-linking reagent, the functional groups on the enzymes can react with an epoxide group to produce covalent bonds such as amino, ester, ether and thioether bonds. For example, in case of bis-epoxide cross-linking reagents, one of the epoxide groups can react with the amino functional group situated on the surface of the amino-functionalized controlled pore silica carrier to form an amino covalent bond. The second epoxide group can react with a functional group situated on an amino acid residue located on the enzyme. For example, an amino functional group from a lysine amino acid residue can react with the epoxide group to form an amino covalent bond. Alternatively, a thiol functional group from a cysteine amino acid residue can react with the epoxide group to form a thioether covalent bond. In yet further embodiments, a carboxylate functional group from a glutamate amino acid residue can react with the epoxide group to form an ester covalent bond or a hydroxyl group from a serine amino acid residue can form an ether covalent bond.

The cross-linking reagents may similarly be used for forming intermolecular linkers between immobilized enzymes, when desired.

The cross-linking reagent can be homobifunctional or heterobifunctional, meaning that the first and second reactive groups can either be the same or different. Preferably, the first and second reactive groups are separated by a linker containing between 3 and 20 atoms comprising any combination of C, H, N and O.

An effective cross-linker should create a covalent link between the enzyme and the support surface and retain the enzyme activity upon cross-linking. Retention of the enzyme activity upon cross-linking is an important desirable feature of a cross-linking reagent which can be tuned with a suitable choice of the reactive groups, the linker group, and the linker length.

The preferred reactive groups selected are chosen for their capability for reacting with amines, hydroxyls, carboxylates or sulfhydryls to create stable covalent linkages via amino, amide, ether, ester, imidoamide, imidothioamide, thioether, thioester or thioamide linkages. A cross-linking reagent capable of cross-linking with the functional groups of the enzyme may contain at least two reactive groups independently selected from epoxides, esters, anhydrides, N-hydroxysuccinimide esters, imidoesters, carbonates, acylisoureas, carbodiimides, maleimides, haloacetyls, thiosulfonates, isocyanates and vinylsulfones. Reactive groups such as carbodiimides can assist in the formation of a covalent linkage by reacting with, for example, a carboxylate group and then itself being subject to a displacement by a second reactive group to form a covalent bond such as an amide bond.

Preferred cross-linking reagents are defined by the formula below:

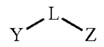

where Y and Z are independently a reactive group selected from an epoxide, ester, anhydride, imidoester, N-hydroxysuccinimide ester, carbonate, acylisourea, a carbodiimide, a maleimide, a haloacetyl, a thiosulfonate, a vinylsulfone and an isocyanate. Preferably, Y and Z are each independently epoxide, N-hydroxysuccinimide ester or imidoester.

L represents a linker between the reactive groups containing between 3 and 20 atoms comprising any combination of C, H, N and O.

More preferred cross-linking reagents are homobifunctional where Y=Z and contain reactive groups selected from an epoxide, ester, anhydride, N-hydroxysuccinimide ester, imidoester, carbonate, acylisourea, maleimide, haloacetyl and vinylsulfone, most preferably epoxide, N-hydroxysuccinimide ester or imidoester.

Even more preferably the cross-linking reagent is a bis-epoxide reagent, still more preferably a bis-epoxide defined by the following formula:

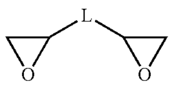

where L represents a linker between the epoxide groups containing between 3 and 20 atoms comprising any combination of C, H, N and O.

Most preferably the bis-epoxide reagent is glycerol diglycidyl ether (GDE, which can be a 1,3- or 1,2-substituted glycerol diglycidyl ether, or a mixture of both isomers), neopentyl glycol diglycidyl ether (NPE), poly(tetra ethylene oxide) diglycidyl ether (PDE), 1,6-hexanediol diglycidyl ether (HDDE) or glycerol triglycidyl ether (GTGE).

Alternative preferred cross-linking reagents include bifunctional sulfonated N-hydroxysuccinimide esters and bifunctional imidoesters such as bis(sulfosuccinimidyl)suberate (BS3) or dimethyl suberimidate (DMS).

A known alternative cross-linker is glutaraldehyde, but it results in the formation of imine bonds so it is not encompassed by the present invention. Glutaraldehyde is a particularly reactive cross-linking reagent that leads to a significant degree of enzyme inactivation. The imine bond formation is also reversible so the links are not very stable.

Preferred Properties of the Biocatalyst

In a preferred embodiment of the first aspect, the support material has a pore diameter from about 20 to about 60 nm, a surface area from about 50 $m^2/g$ to about 200 $m^2/g$ and a pore volume of from about 0.5 mL/g to about 1.5 mL/g, and the enzyme(s) is/are selected from list (A), or even more preferably from list (B).

In a preferred embodiment of the second aspect, the support material has a pore diameter from about 20 to about 60 nm, a surface area from about 50 $m^2/g$ to about 200 $m^2/g$ and a pore volume of from about 0.5 mL/g to about 1.5 mL/g, and the enzyme(s) is/are selected from list (A), or even more preferably from list (B).

In a preferred embodiment of the third aspect, the support material has a pore diameter from about 20 to about 60 nm, a surface area from about 50 $m^2/g$ to about 200 $m^2/g$ and a pore volume of from about 0.5 mL/g to about 1.5 mL/g, and the enzyme(s) is/are selected from list (A), or even more preferably from list (B).

In some embodiments, the immobilized enzyme retains at least 20%, preferably at least 30%; more preferably at least 40%, even more preferably at least 50%, still more preferably at least 60%, yet more preferably at least 70%, yet even more preferably at least 80%, and most preferably at least 90% of its activity after immobilization compared to the state prior to immobilization. In rare cases, immobilization may even enhance activity resulting in more than 100% apparent retention. In some embodiments, the immobilized enzyme retains 20%-100%, preferably 30%-100%; more preferably 40%-100%, even more preferably 50%-100%, still more preferably 60%-100%, yet more preferably 70%-100%, yet even more preferably 80%-100%, and most preferably 90%-100% of its activity after immobilization compared to the state prior to immobilization.

In some embodiments the immobilized enzyme retains at least 20%, preferably at least 30%; more preferably at least 40%, even more preferably at least 50%, still more preferably at least 60%, yet more preferably at least 70%, yet even more preferably at least 80%, and most preferably at least 90% of its activity after 20 h under continuous flow conditions compared to the state prior to immobilization. In some embodiments the immobilized enzyme retains 20%-100%, preferably 30%-100%; more preferably 40%-100%, even more preferably 50%-100%, still more preferably 60%-100%, yet more preferably 70%-100%, yet even more preferably 80%-100%, and most preferably 90%-100% of its activity after 20 h under continuous flow conditions compared to the state prior to immobilization. In some embodiments the immobilized enzyme retains at least 20%, preferably at least 30%; more preferably at least 40%, even more preferably at least 50%, still more preferably at least 60%, yet more preferably at least 70%, yet even more preferably at least 80%, and most preferably at least 90% of its activity after 70 h under continuous flow conditions compared to the state prior to immobilization. In some embodiments the immobilized enzyme retains 20%-100%, preferably 30%-100%; more preferably 40%-100%, even more preferably 50%-100%, still more preferably 60%-100%, yet more preferably 70%-100%, yet even more preferably 80%-100%, and most preferably 90%-100% of its activity after 70 h under continuous flow conditions compared to the state prior to immobilization.

In some embodiments the immobilized enzyme retains at least 20%, preferably at least 30%; more preferably at least 40%, even more preferably at least 50%, still more preferably at least 60%, yet more preferably at least 70%, yet even more preferably at least 80%, and most preferably at least 90% of its activity after 200 h under continuous flow conditions compared to the state prior to immobilization. In some embodiments the immobilized enzyme retains 20%-100%, preferably 30%-100%; more preferably 40%-100%, even more preferably 50%-100%, still more preferably 60%-100%, yet more preferably 70%-100%, yet even more preferably 80%-100%, and most preferably 90%-100% of its activity after 200 h under continuous flow conditions compared to the state prior to immobilization.

In some embodiments the immobilized enzyme retains at least 20%, preferably at least 30%; more preferably at least 40%, even more preferably at least 50%, still more preferably at least 60%, yet more preferably at least 70%, yet even more preferably at least 80%, and most preferably at least 90% of its activity after 500 h under continuous flow conditions compared to the state prior to immobilization. In some embodiments the immobilized enzyme retains 20%-100%, preferably 30%-100%; more preferably 40%-100%, even more preferably 50%-100%, still more preferably 60%-100%, yet more preferably 70%-100%, further more preferably 80%-100%, and most preferably 90%-100% of its activity after 500 h under continuous flow conditions compared to the state prior to immobilization.

In the above preferred embodiments, the continuous flow conditions can be conducted in aqueous solutions, organic solvents or with neat substrates.

In the above preferred embodiments the continuous flow is conducted in aqueous solution taking place at a pH between 4.0 and 9.0, or more preferably between 6.0 and 7.5.

In the above preferred embodiments, the continuous flow conditions may comprise a temperature ranging from 4° C. and 100° C. or more preferably between 30° C. and 70° C.

It should be noted that certain processes can also accommodate reaction steps that proceed with lower conversions, e.g., at least 20%, or preferably at least 40%, particularly where the product of interest is of high value.

In some embodiments, at least two different enzymes are immobilized on the support material. More preferably, the at least two immobilized enzymes are each capable of catalyzing a different step of a multi-step organic synthesis. The multi-step synthesis may comprise at least 3 intermediates, such as 3, 4, 5, 6, 7, 8, 9 or 10 intermediates. In some embodiments, the multi-step synthesis comprises 3 to 10 steps, such as 3 to 5 steps, such as 4 to 6 steps, such as 5 to 7 steps, such as 6 to 8 steps; or such as 4 to 10 steps, such as 5 to 10 steps, such as 6 to 10 steps, such as 7 to 10 steps, such as 8 to 10 steps, such as 9 to 10 steps.

In certain embodiments, at least one of the immobilized enzymes catalyzes the regeneration of a cofactor.

Most Preferred Embodiments of the Biocatalyst

In a preferred embodiment of the second, third or fourth aspect of the present invention, the enzyme is a lipase (preferably CalB) comprising metal chelating tag such as a His-tag, wherein the enzyme is immobilized to a surface comprising amino-functionalized aliphatic moieties via an interaction mediated by a chelated $Zn^{2+}$ ion.

In another preferred embodiment of the second, third or fourth aspect, the enzyme is TbSADH comprising metal chelating tag such as a His-tag, wherein the enzyme is immobilized to the surface via an interaction mediated by a chelated $Zn^{2+}$ ion.

In a further preferred embodiment of the second, third or fourth aspect, the enzyme is ATA comprising a metal chelating tag such as a His-tag, wherein the enzyme is immobilized to a surface comprising structure (1), (2), (3) or (4) via an interaction mediated by a chelated metal ion.

In a yet another preferred embodiment of the second, third or fourth aspect, the enzyme is SucP comprising metal chelating tag such as a His-tag, wherein the enzyme is immobilized to a surface comprising structure (1).

In another preferred embodiment of the second, third or fourth aspect, the enzyme is TLL preferably not comprising a metal chelating tag such as a His-tag, wherein the enzyme is immobilized to a surface comprising structure (1) or (4).

In another preferred embodiment of the second, third or fourth aspect, the enzyme is glucosyl transferase comprising a metal chelating tag such as a His-tag, wherein the enzyme is immobilized to a surface comprising structure (1).

In another preferred embodiment of the first, second, third or fourth aspect, the lipase CalB is immobilized to a surface comprising structure (1) or (4), preferably non-covalently, wherein the CalB most preferably does not comprise a metal chelating tag such as a His-tag.

In yet another preferred embodiment of the second, third or fourth aspect, the enzyme is CalB (preferably not comprising a metal chelating tag such as a His-tag), wherein the enzyme is immobilized to the surface comprising structure (4).

In still another preferred embodiment of the third aspect, the enzyme is amyloglucosidase (preferably not comprising a metal chelating tag such as a His-tag). It is preferably immobilized on a surface functionalized with structure (1), (2), (3) or (4), optionally together with a different second functionalization. The second functionalization may be structure (1) or an alkyl such as propyl or octyl.

Uses of a Biocatalyst

In a fifth aspect, the present invention provides a use of a biocatalyst according to the first, second, third or fourth aspect, in a reactor for synthesis of an organic compound.

The reactor may be any industrial reactor type. The reactor may be a batch reactor or a continuous flow reactor. The reactor includes continuous stirred tank reactors (CSTR), slurry bubble columns or fixed bed reactors and known variations thereof. Continuous flow fixed bed reactors are preferred.

The synthesis may take place in aqueous conditions. Alternatively, the synthesis may take place in an organic solvent. The synthesis may also take place in neat substrate. The latter is particularly preferred for lipases. The biocatalysts may be also used in 3-phase reactions, such as those that require the presence of liquid solutions and gaseous reagents, such as oxidations utilising oxygen or air as a reactant. In such instances the particle sizes are preferably tailored for operation in a fixed bed reactor such as a trickle bed, or a CSTR, or a bubble column another reactor format suited for the particular 3-phase conditions.

The synthesis in the fifth aspect may be a multi-step synthesis, preferably comprising at least 3 intermediates, such as 3, 4, 5, 6, 7, 8, 9 or 10 intermediates. The multi-step synthesis is preferably a linear synthesis.

Methods for Synthesis Using a Biocatalyst

In a sixth aspect, the present invention provides a method for synthesis of an organic compound, comprising:

a. providing a biocatalyst according to the first, second, third or fourth aspect, placed in a reactor;
b. feeding a precursor to the organic compound to the reactor, whereby the immobilized enzyme(s) catalyze(s) reaction/reactions resulting in the synthesis of the organic compound; and
c. recovering the organic compound.

The reactor may be any industrial reactor type. The reactor may be a batch reactor or a continuous flow reactor. The reactor includes continuous stirred tank reactors (CSTR), slurry bubble columns or fixed bed reactors and known variations thereof. Continuous flow fixed bed reactors are preferred.

The reaction/reactions may take place in aqueous conditions, in an organic solvent, or in neat substrate. The latter is particularly preferred for lipases. The method may involve 3-phase reactions, such as those that require the presence of liquid solutions and gaseous reagents, such as oxidations utilising oxygen or air as a reactant. In such instances the particle sizes are preferably tailored for operation in a fixed bed reactor such as a trickle bed, or a CSTR, or a bubble column another reactor format suited for the particular 3-phase conditions.

The synthesis in the third aspect may be a multi-step synthesis, preferably comprising at least 3 intermediates, such as 3, 4, 5, 6, 7, 8, 9 or 10 intermediates. The multi-step synthesis is preferably a linear synthesis.

Methods for Manufacturing a Biocatalyst

In a seventh aspect, the present invention provides a method of manufacturing a biocatalyst according to the first, second, third or fourth aspect, comprising:

a. providing one or more catalytically active enzyme(s);
b. providing a controlled porosity silica (CPS) as support material, as defined for the first, second, third or fourth aspect, wherein the pore diameter is between about 20 and about 100 nm, said support material comprising an amino-functionalized surface; and
c. immobilizing the one or more enzyme(s) on the support material.

In certain embodiments, the method of the seventh aspect further comprises selecting a bifunctional cross-linking reagent capable of producing amino, amide, ester, ether, thioether, imidoamide, imidothioamide, thioester or thioamide bonds (preferably amino, amide or thioamide, more preferably amino, amido or imidoamido, most preferably amino or amide) when reacted with the enzyme(s) and the amino-functionalized surface, and covalently cross-linking the enzyme(s) using the bifunctional reagent.

Suitable bifunctional cross-linking reagents for the method of the seventh aspect have been discussed above in the context of the first to fourth aspects.

The bifunctional reagent may be contacted with the amino-functionalized CPS before the enzyme (s) is/are immobilized, after the enzyme(s) is/are immobilized, or both before and after immobilization. Whether the bifunctional cross-linking reagent is added before and/or after the enzyme immobilization step depends on the aspect and the embodiment of the invention. For example, a bifunctional cross-linking reagent can be added to the amino-functionalised support prior to enzyme immobilization, whereby one of the reactive groups of the cross-linking reagent will react with the amino-functionalized surface of the support material. For example, in the case where the cross-linking reagent is a bis-epoxide, it is anticipated that one of the epoxide groups will react with the amino-functionalized CPS surface, while the second epoxide group is then available to react with the amino acids present in the enzyme, thus immobilizing the enzyme directly in a covalent manner.

When added prior to enzyme immobilization, the bifunctional cross-linking reagent can be added in a molar excess, molar equivalent, or in a sub-molar equivalent relative to the number of moles of the amino groups on the surface of the CPS. Furthermore, in certain embodiments the bifunctional cross-linking reagent can be added after initial non-covalent immobilization where is it anticipated that the first reactive group will react with the amino-functionalized CPS surface, while the second reactive group is then available to react with the amino acids present in the enzyme.

Furthermore, in certain embodiments the cross-linking reagent can be added both before and after the immobilization (double cross-linking). The cross-linking reagent may also react in such a way as to provide a covalent linkage between two enzyme structures. The inventors have surprisingly found that using the bifunctional (preferably a bis-epoxide, a bifunctional sulfonated N-hydroxysuccimide ester or a bifunctional imidoester) cross-linking reagents as described it is possible to fully retain the activity of enzyme upon cross-linking. The retention of activity upon cross-linking applies across many enzyme classes and thus provide a general protocol for the preparation of stable immobilized biocatalysts. This contrasts with reports in the literature where activity loss is a general feature of cross-linking.

The inventors have also found that significant activity loss is evident when attempting to immobilize and crosslink on a CPS surface without amino-functionalization. The immobilization of enzymes onto the CPS surface without amino-functionalization is possible, but the resultant immobilized biocatalyst only possesses limited stability and therefore CPS without the amino-functionalized surface does not represent a broadly useful support material for immobilizing enzymes for synthesis. See example 4.3 which illustrates that the biocatalysts produced using a CPS surface without amino-functionalisation cannot tolerate the presence of the crosslinking reagents without a significant loss of activity. The invention described herein therefore provides significant advantages compared to the situation where the immobilization occurs for example via non-specific physical adsorption on a surface without a tailored coating.

Examples 4.1-4.4 illustrate full retention of activity in the presence of a covalent linkage. In such embodiments the immobilized biocatalyst can possess additional stability in the presence of the components of a reaction. The additional stability can manifest in a longer period of stability when operating under continuous flow conditions, such as the continuous flow conditions operating in a fixed bed reactor. Examples 5.2-5.3 illustrate such a longer period of stability in a fixed bed reactor when compared with the immobilized enzyme without the presence of a covalent linkage.

The enzyme(s) may be immobilized to the surface via an interaction mediated by a chelated metal ion, preferably $Ni^{2+}$, $Cu^{2+}$, $Mg^{2+}$, $Fe^{3+}$ or $Zn^{2+}$, most preferably $Zn^{2+}$.

The enzyme(s) may be selected from list (A), more preferably from list (B). The enzyme(s) may optionally comprise a polyhistidine tag.

At least one of the enzyme(s) may be provided in a cell lysate for the immobilization step. Alternatively, the enzyme(s) may be provided in a purified or isolated form.

At least one of the enzyme(s) may be provided as a preparation comprising at least 70%, more preferably at least 80%, even more preferably at least 90%, most preferably at least 95% of the enzyme by weight of total protein in the preparation, such as 70%-100%, 80%-100%, 90%-100% or 95%-100%.

Figure 3:
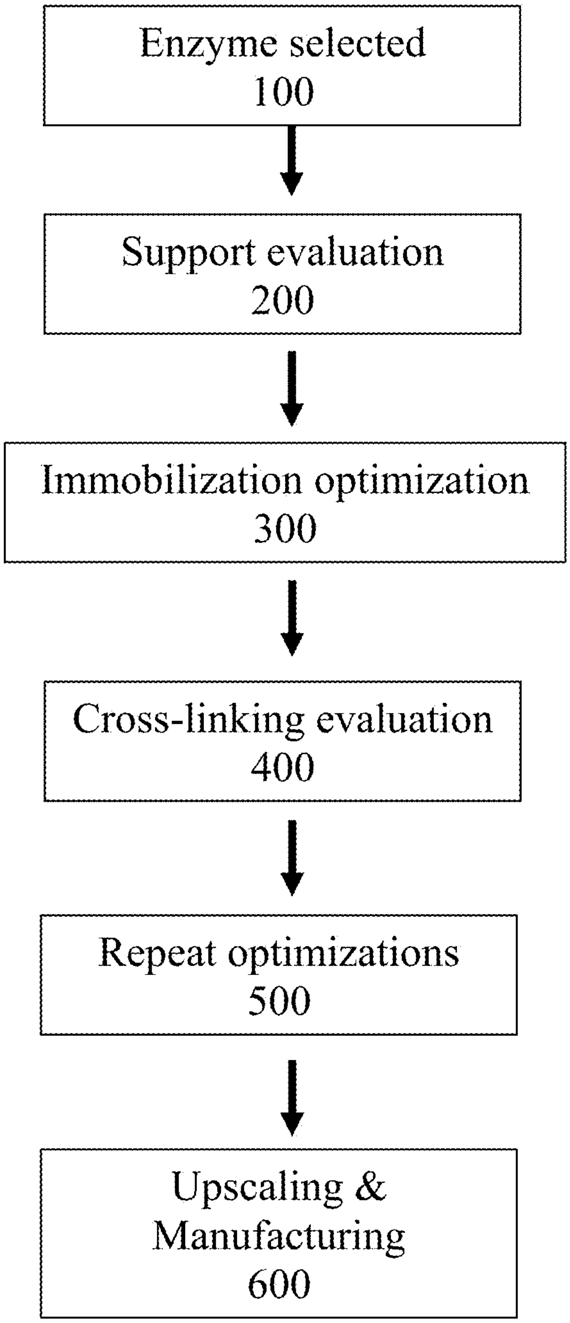
FIG. 3: Flowchart of optimising a biocatalyst for manufacturing.

The present disclosure also provides a process for optimizing a biocatalyst comprising a catalytically active enzyme immobilized on an amino-functionalized CPS support (refer to FIG. 3). Initially, the one or more catalytically active enzyme(s) to be immobilized are chosen and provided (100).

Secondly two, three, four, five or more different controlled porosity silica (CPS) support materials are provided, fulfilling the criteria provided under above section titled Support material. Briefly, the pore diameter is between about 20 and about 100 nm, and the support material comprises an amino-functionalized surface. Preferably, the support material is as defined above for the first, second, third or fourth aspect of the present invention. The support material may for instance be amino-functionalized with propylamine, propylNH—N-aminoethyl, phenethyl-methyl-NH—N-aminoethyl or propyl-NH—N-aminohexyl. The support material may comprise an immobilized metal chelating group. To identify a suitable support material, immobilization of the one or more enzyme(s) on the support materials is performed, and the immobilized enzyme activity between the support materials is compared (200). Various immobilization conditions may be tested. The initial conditions may include the absence as well as presence of a chelated metal ion such as $Ni^{2+}$, $Cu^{2+}$, $Mg^{2+}$, $Fe^{3+}$ and $Zn^{2+}$. The immobilization conditions may include for instance a buffer with pH of 6-8, salt concentration of 0-300 mM, temperature of 20-30° C. and/or incubation time of 2-24 h.

Optionally, further immobilization conditions may be screened to maximize immobilized enzyme activity, by performing immobilization in at least two different values of at least one parameter of the best initial conditions: initial enzyme concentration, metal ion concentration, buffer type, pH, salt concentration, additives, time and temperature, followed by comparing immobilized enzyme activity between the immobilization conditions, and selecting the best optimized immobilization conditions (300).

As discussed above, covalent cross-linking may be useful in certain applications. Optionally, cross-linking conditions may be screened to maximize immobilized enzyme activity and/or stability, by testing at least two values of at least one parameter of: cross linker type, cross linker amount, cross linker concentration, cross linking solution composition, cross-linking time and cross-linking temperature. The cross-linker fulfils the criteria provided under above section titled Cross-linking reagents. The cross-linker type may include at least one bisepoxide, at least one bifunctional sulfonated N-hydroxysuccinimide ester and/or at least one bifunctional imidoester. The activity is typically compared to non-cross linked immobilized enzyme. The cross-linker concentration may be 0.1-3% (v/v), cross-linking temperature is 0-25° C., cross-linking time is 2-24 h and/or cross-linking solution may have a pH of 6-8. The immobilized enzyme activity between the cross-linking conditions may be compared, followed by selecting the best cross-linking conditions (400).

Optionally, one or more of the above steps (200)-(400) may be repeated with additional variations to further optimize results (500). The process may result in at least one immobilized enzyme retaining at least 20% (such as 20%-100%, preferably 50%, or 50%-100%) of its activity after immobilization compared to the state prior to immobilization, preferably after 20 h under continuous flow conditions compared to the state prior to immobilization. The optimized biocatalyst is then scaled up and manufactured according to demand (600).

General Statements Relating to the Present Disclosure

The term "comprising" is to be interpreted as including, but not being limited to. All references are hereby incorporated by reference. The arrangement of the present disclosure into sections with headings and subheadings is merely to improve legibility and is not to be interpreted limiting in any way, in particular, the division does not in any way preclude or limit combining features under different headings and subheadings with each other.

EXAMPLES

The following examples are not to be regarded as limiting. For further information on the experimental details, the skilled reader is directed to a separate section titled Materials and Methods.

Example 1 Support Preparation 1.1 Supports

All the controlled pore glass (CPG) and controlled pore silica (CPS) amino-functionalised supports used for the immobilisations were synthesised in-house. CPG core (70-125 μm particle size, 50 nm pore size, 60 $m^2$ surface area) was purchased from Schott AG. CPS cores (Cariact Q30: 70-150 μm particle size, 30 nm pore size, 99 $m^2$ surface area, and Cariact Q50: 70-150 μm particle size, 50 nm pore size, 80 $m^2$ surface area) were purchased from Fuji Silysia Chemical. Polymer beads used for comparison with CPG and CPS were purchased from commercial sources. ReliZyme EA403/S (ethylamine functionalisation on cross-linked copolymer of methacrylate) and ReliZyme HA403/S (hexylamine functionalisation on crosslinked copolymer of methacrylate) were purchased from Biokal. Dowex® 66 free base (polyamine groups on styrene-divinylbenzene matrix) was purchased from Sigma-Aldrich.

1.2 Synthesis of Amino-Functionalised Supports

The controlled pore core (CPG or CPS) (5 g) was transferred to a jacketed glass reactor with overhead stirrer and toluene was added (100 mL). Cores were amino-functionalised with four different silanes (Table 1). Each silane (15 mL) was added to the reactor and incubated for 22 h (250-290 rpm, 80° C.). The solid was filtered under vacuum, washed with toluene (2×200 mL) and then washed with EtOH 99.7% (2×200 mL). After the washing steps, the solid was filtered using a glass filter funnel under vacuum for 60 min. The amino-functionalised support was transferred to a crystallising dish and dried under vacuum overnight at 120° C.

TABLE 1

Silanes for amino-functionalisation of controlled pore glass and silica (CPG and CPS).

| Silane | Amino-functionalisation | CAS number |
|---|---|---|
| (3-Aminopropyl)trimethoxysilane | propylamine | 919-30-2 |
| N-(2-Aminoethyl)-3-aminopropyltrimethoxysilane | propylNH—N-aminoethyl | 1760-24-3 |
| (Aminoethylaminomethyl)phenethyltrimethoxy silane | phenethyl-methyl-NH—N-aminoethyl | 74113-77-2 |
| N-(6-aminohexyl)aminopropyltrimethoxysilane | propyl-NH—N-aminohexyl | 51895-58-0 |

1.3 Chelator Attachment

2',4'-Dihydroxyacetophenone (500 mg, 3.3 mmol) was added to a 250 mL Erlenmeyer flask containing methanol (16 mL). The amino-functionalised support (2 g) was added to the mixture and incubated for 2 h (150 rpm, 25° C.). Sodium borohydride (600 mg, 15.9 mmol) was slowly added to the flask and incubated for further 2 h (150 rpm, 25° C.). The slurry containing the support was washed stepwise as followed: support slurry was transferred to a glass filter and washed with deionised water (40 mL) under vacuum. Deionised water (10 mL) was added and allowed to drip without vacuum. Deionised water (40 mL) was added and vacuum applied. Deionised water (10 mL) was added and allowed to drip without vacuum. After that, the pH of each support was evaluated, and if pH was above 7, further deionised water (45 mL) was added and vacuum applied. After reaching a desired pH of 7 with the deionised water washes, the support was washed with ethanol (50 mL) under vacuum, followed by wash with acetone (25 mL) under vacuum. The support with attached chelator was dried under vacuum in a desiccator overnight.

1.4 Metal Stripping from EziG Supports

The CPG carriers LCAA CPG ($Fe^{3+}$), HybCPG VBC ($Fe^{3+}$) and HybCPG copo ($Fe^{3+}$) (see WO2015/115993) were also used as comparative examples for the immobilisation technique described in the present invention. For evaluating the effect of different metals on CPG carrier, the chelated $Fe^{3+}$ was stripped from the support. The CPG material (5 g) was transferred to a 100 mL Duran bottle and 2 M HCl (50 m) was added. The flask was left on a tilt/roller mixer for 35 min (70 rpm, 21° C.). The procedure was repeated for another 3 cycles and, between each cycle, the HCl was removed, fresh 2 M HCl (50 mL) added and incubated for 35 min (70 rpm, 21° C.). The solid was filtered on a glass filter funnel under vacuum and washed with deionised water (500 mL), followed by wash with 25 mM sodium phosphate (NaP), pH 7.3 (300 mL), further deionised water (300 mL) and acetone (50 mL). The stripped support was dried under vacuum in a desiccator overnight.

1.5 Metal Deposition

Each immobilisation support (100 mg) was weighed into 15 mL Falcon tubes and deionised water (2 mL) was added. The mixture was used as a support slurry to fill 6 wells maximum on the plate and it was prepared according to the supports required for each assay. The slurry containing the support (200 μL) was transferred to each well in a 96-well deep well plate to reach approximately 10 mg of support per well. Two stock solutions of each metal salt ($FeCl_3$, $ZnCl_2$, $NiCl_2$, $MgCO_2$, $CuCl_2$, at 1.55 and 0.26 mM) were prepared for metal ion deposition on amino-functionalised support. For CalB immobilisations, a metal stock solution of 1.55 mM (300 μL) was added to the support to reach a final concentration of 0.93 mM in the well (Table 2). For TbSADH immobilisation, metal stock solutions of 0.26 mM (300 μL) were added to the support to reach a final concentration of 0.15 mM in the well (Table 2). The plate containing support and metal solution was incubated for 30 min (1300 rpm, 21° C.). The metal solution was then removed, and the supports were washed with deionised water (4×1 mL), followed by a wash with buffer solution or deionised water (1×1 mL) (Table 2). For comparison purposes, formulations without the presence of metal were also included in reaction screening for each enzyme.

TABLE 2

Conditions for metal deposition on amino-functionalised support for different enzymes.

| Enzyme | Final metal concentration (mM) | Washing after metal deposition |
|---|---|---|
| CalB | 0.93 | 20 mM MOPS buffer, pH 7.5 |
| TbSADH | 0.15 | 50 mM MOPS, 150 mM NaCl, pH 7 |
| Lipase from *Candida* sp. | 0.15 | 20 mM MOPS pH 7.5 |
| Lipase from *Aspergillus oryzae* | 0.15 | deionised water |

1.6 Zinc Deposition at Gram Scale

The immobilisation support (1 g) was weighed into a 100 mL Duran bottle and deionised water (10.4 mL) was added. $ZnCl_2$ stock solutions were prepared for metal ion deposition and added to the support according to the final metal concentration required. The bottle was left on a tilt/roller mixer for 1 h (20 rpm, 21° C.). The slurry containing the support was transferred to a glass filter column and washed with deionised water (60 mL) followed by acetone wash (30 mL) under vacuum. The support was transferred to 15 mL Falcon tubes and dried under vacuum in a desiccator overnight. This material was used in examples 4.1 to 4.5 and 5.1 to 5.3.

1.7 Enzymes

Lipase from *Candida Antarctica* B with a N-terminal His-tag (CalB), alcohol dehydrogenase from *Thermoan-*

*aerobacter brockii* with N-terminal His-tag (TbSADH), wild-type sucrose phosphorylase from *Bifidobacterium adolescentis* with N-terminal His-tag (SucP1), variant of sucrose phosphorylase from *Bifidobacterium adolescentis* with N-terminal His-tag (SucP2, see WO 2016/075219 and J. Agric. Food Chem. 2017, 65, 6030-6041) and Glycosyl transferase from *Leuconostoc mesenteroides* with N-terminal His-Tag were produced in-house using known cultivation procedures. Lipase from *Candida* sp. And lipase from *Aspergillus oryzae* were purchase from Sigma-Aldrich. Lipozyme® TL 100 L and Lipozyme® TL IM were purchased from Novozymes.

1.8 Analytical Methods

Gas chromatography chiral analyses were carried out on an Agilent 6890N GC system equipped with a flame-ionization detector (FID) and an Agilent J&W CP-Chirasil Dex CB capillary column (dimensions: 25 m×0.25 mm×0.25 µm; stationary phase: cyclodextrin bonded to dimethylpolysiloxane) using $H_2$ (2 mL/min flow rate) as carrier gas.

GC-FID Method for reactions using lipases: injector temperature: 220° C.; detector temperature: 250° C.; injection volume: 1 µL and split ratio: 20:1. Oven temperature program: start at 115° C. hold time 9 min; total run time: 9 min. Retention times: dodecane 4.3 min; (R)-1-phenylethyl acetate 5.4 min; (R)-1-phenylethanol 7.5 min; (S)-1-phenylethanol 8.2 min.

GC-FID Method for reactions using TbSADH: injector temperature: 200° C.; detector temperature: 275° C.; injection volume: 1 IL; split ratio: 20:1. Oven temperature program: start at 100° C. hold time 2 min; rate 15° C./min to 195° C. hold time 2 min; total run time: 11 min. Retention times: phenoxy-2-propanone 5.7 min; (S)-1-phenoxy-2-propanol 6.3 min; (R)-1-phenoxy-2-propanol 6.4 min.

HPLC-RID Method for reactions using SucP1: oven temperature: 30° C.; detector temperature: 30° C.; injection volume: 10 µL; flow rate: 0.8 mL/min; total run time: 12 min. Retention times: phosphorylated sugars 3.8 min; sucrose 4.5 min; glucose 5.4 min; fructose 5.9 min.

High-performance liquid chromatography for reactions using SucP2 was carried out using an Agilent Infinity II HPLC system equipped with a ESA Corona charged aerosol detector (CAD) and a Shodex HILICpak VG-50 4E column (dimensions: 4.6 mm×250 mm; stationary phase: polymer-based containing chemically bonded amino groups and hydrophilic groups) using acetonitrile:methanol:water (75:10:15) as mobile phase on isocratic mode.

HPLC-CAD Method for reactions using SucP2: oven temperature: 50° C.; injection volume: 10 µL; flow rate: 0.8 mL/min; total run time: 14 min. Retention times: fructose 6.1 min; glucose 7.2 min; sucrose 9.4 min; kojibiose 11.6 min.

High-performance liquid chromatography for reactions using glycosyl transferase analyses was carried out using a Rigol L3400 HPLC system equipped with Rigol L3500 UV-Vis detector and a Merck SeQuant® ZIC®-HILIC 3.5 µm, 150 Å (dimensions: 4.6 mm×150 mm; stationary phase: polyether ether ketone) using acetonitrile and 50 mM ammonium acetate, pH 4.5 (pH adjusted with formic acid) (75:25) as mobile phase on isocratic mode.

HPLC-UV-Vis Method for reactions using glycosyl transferase: oven temperature: 40° C.; injection volume: 2 µL; flow rate: 0.75 mL/min; total run time: 6 min. Retention times: hydroquinone 1.4 min; α-arbutin 2.0 min.

Example 2 Reaction Screening with Amino-Functionalised Supports 2.1 Immobilisation of CalB 2.1.1 Immobilisation Cell-free extract containing CalB-N-His in 20 mM MOPS, pH 7.5 (50 mL) was clarified by centrifugation for 60 min (11 000 rpm, 4° C.) followed by filtration using a 0.45 µm PVDF filter. The pH of the clarified cell-free extract was adjusted to 7.5 using 0.1 M NaOH. The cell-free extract (500 µL) was transferred to a 96-well deep well plate containing the supports with freshly deposited metals and incubated for 2 h (1200 rpm, 25° C.). The supernatants were removed, and the immobilised supports were washed with 250 mM MOPS, pH 7.5 (2×1 mL). The catalysts were dried under vacuum in a desiccator overnight.

2.1.2 Determination of Immobilised Yield

The cell-free extract and supernatant from the immobilisations were diluted 400 times with 20 mM MOPS, pH 7.5. An aliquot of the diluted enzyme solution and supernatant (30 µL) was mixed with a reaction mixture (170 µL) containing 20 mM MOPS, pH 7.5 and 3 mM 4-nitrophenyl acetate in acetonitrile. The formation of 4-nitrophenol was measured by the absorbance ($A_{410}$) at 410 nm every 10 s for 3 minutes using a plate reader). Rates of the reaction with each supernatant from immobilisations and fresh enzyme solution were extracted from linear regression of the data points ($A_{410}$/min). The immobilised yield was calculated by determining the percentage of enzymatic activity left in the supernatant after immobilisation compared to the enzymatic activity in the cell-free extract (Table 3). All the measurements were performed in duplicates and the result is presented as the means of the individual samples.

Scheme 1.
Hydrolysis of 4-nitrophenylacetate (3 mM) by lipases for immobilised yield determination.

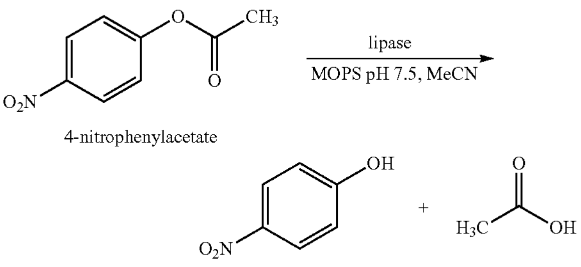

4-nitrophenylacetate 4-nitrophenol 2.1.3 Activity of Immobilised Catalyst in Organic Solvent The activity of the heterogeneous catalysts was determined by their ability to convert (±)-1-phenylethanol and vinyl acetate to (R)-phenylethyl acetate (Scheme 2). A reaction mixture (1 mL) containing 2 M (±)-1-phenylethanol, 1.2 M vinyl acetate and 1% (v/v) dodecane (internal standard) in MTBE was added to the immobilised catalyst and the mixture was incubated for 30 min (1200 rpm, 25° C.). After stopping the mixing and allowing the catalyst to settle, an aliquot of the supernatant (10 µL) was added to EtOAc (990 µL) and analysed by GC-FID to determine the conversion of (±)-1-phenylethanol (Table 3). All the measurements were performed in duplicate and the result is presented as the average of the individual samples.

Scheme 2.
Transesterification of (±)-1-phenylethanol (2M) with vinyl acetate (1.2M) catalysed by immobilised CalB.

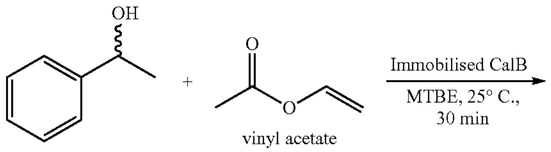

(±) -1-phenylethanol vinyl acetate

-continued

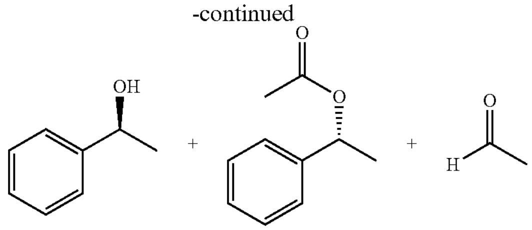

(S)-1-phenylethanol (R)-1-phenylethyl acetate

TABLE 3

Performance of immobilised CalB on amino-functionalised supports chelated with various metals. Immobilised yield is based on the activity of supernatants after immobilization for the hydrolysis of 4-nitrophenyl acetate and conversion is based on the activity of the immobilised catalyst for the transesterification of (±)-1-phenylethanol with vinyl acetate. The CPS used in Table 3 is CPS Q30.

| Core | Functionalisation | Metal | Immobilised yield [%] | Conversion [%] |
|---|---|---|---|---|
| CPG | propylamine | $Fe^{3+}$ | 40.8 | 5.2 |
| CPG | propylamine | $Zn^{2+}$ | 81.2 | 24.3 |
| CPG | propylamine | $Ni^{2+}$ | 4.3 | 3.9 |
| CPG | propylamine | $Mg^{2+}$ | 3.9 | 3.8 |
| CPG | propylamine | $Cu^{2+}$ | 12.5 | 3.7 |
| CPG | propylamine | — | 11.5 | 3.4 |
| CPG | propylamine + chelator | $Fe^{3+}$ | 3.7 | 5.1 |
| CPG | propylamine + chelator | $Zn^{2+}$ | 73.7 | 23.3 |
| CPG | propylamine + chelator | $Ni^{2+}$ | 2.0 | 4.4 |
| CPG | propylamine + chelator | $Mg^{2+}$ | 18.8 | 4.0 |
| CPG | propylamine + chelator | $Cu^{2+}$ | 22.7 | 4.2 |
| CPG | propylamine + chelator | — | 4.4 | 3.7 |
| CPS | propylamine | $Fe^{3+}$ | 46.3 | 9.7 |
| CPS | propylamine | $Zn^{2+}$ | 88.5 | 20.8 |
| CPS | propylamine | $Ni^{2+}$ | 24.9 | 8.4 |
| CPS | propylamine | $Mg^{2+}$ | 29.1 | 9.0 |
| CPS | propylamine | $Cu^{2+}$ | 32.4 | 7.2 |
| CPS | propylamine | — | 19.3 | 8.3 |
| CPS | propylamine + chelator | $Fe^{3+}$ | 33.1 | 11.3 |
| CPS | propylamine + chelator | $Zn^{2+}$ | 88.2 | 20.5 |
| CPS | propylamine + chelator | $Ni^{2+}$ | 35.1 | 10.0 |
| CPS | propylamine + chelator | $Mg^{2+}$ | 23.4 | 9.4 |
| CPS | propylamine + chelator | $Cu^{2+}$ | 32.7 | 10.1 |
| CPS | propylamine + chelator | — | 20.2 | 9.2 |
| CPG | propylNH—N-aminoethyl | $Fe^{3+}$ | 32.6 | 3.1 |
| CPG | propylNH—N-aminoethyl | $Zn^{2+}$ | 58.5 | 19.4 |
| CPG | propylNH—N-aminoethyl | $Ni^{2+}$ | 10.6 | 4.8 |
| CPG | propylNH—N-aminoethyl | $Mg^{2+}$ | 0.0 | 3.1 |
| CPG | propylNH—N-aminoethyl | $Cu^{2+}$ | 5.7 | 5.0 |
| CPG | propylNH—N-aminoethyl | — | 16.8 | 2.9 |
| CPG | propylNH—N-aminoethyl + chelator | $Fe^{3+}$ | 20.3 | 4.2 |
| CPG | propylNH—N-aminoethyl + chelator | $Zn^{2+}$ | 57.3 | 19.0 |
| CPG | propylNH—N-aminoethyl + chelator | $Ni^{2+}$ | 27.5 | 6.9 |
| CPG | propylNH—N-aminoethyl + chelator | $Mg^{2+}$ | 15.2 | 3.7 |
| CPG | propylNH—N-aminoethyl + chelator | $Cu^{2+}$ | 10.5 | 6.9 |
| CPG | propylNH—N-aminoethyl + chelator | — | 5.1 | 4.4 |
| CPS | propylNH—N-aminoethyl | $Fe^{3+}$ | 28.0 | 4.6 |
| CPS | propylNH—N-aminoethyl | $Zn^{2+}$ | 73.1 | 20.9 |
| CPS | propylNH—N-aminoethyl | $Ni^{2+}$ | 16.9 | 7.3 |
| CPS | propylNH—N-aminoethyl | $Mg^{2+}$ | 8.5 | 4.7 |
| CPS | propylNH—N-aminoethyl | $Cu^{2+}$ | 12.9 | 7.5 |
| CPS | propylNH—N-aminoethyl | — | 0.0 | 4.3 |
| CPS | propylNH—N-aminoethyl + chelator | $Fe^{3+}$ | 49.6 | 9.8 |
| CPS | propylNH—N-aminoethyl + chelator | $Zn^{2+}$ | 70.0 | 19.8 |
| CPS | propylNH—N-aminoethyl + chelator | $Ni^{2+}$ | 38.8 | 13.6 |
| CPS | propylNH—N-aminoethyl + chelator | $Mg^{2+}$ | 20.1 | 7.8 |
| CPS | propylNH—N-aminoethyl + chelator | $Cu^{2+}$ | 32.5 | 11.9 |
| CPS | propylNH—N-aminoethyl + chelator | — | 17.1 | 8.4 |
| CPG | phenethyl-methyl-NH—N-aminoethyl | $Fe^{3+}$ | 32.1 | 6.4 |
| CPG | phenethyl-methyl-NH—N-aminoethyl | $Zn^{2+}$ | 57.5 | 12.5 |
| CPG | phenethyl-methyl-NH—N-aminoethyl | $Ni^{2+}$ | 35.2 | 8.9 |
| CPG | phenethyl-methyl-NH—N-aminoethyl | $Mg^{2+}$ | 10.9 | 5.4 |
| CPG | phenethyl-methyl-NH—N-aminoethyl | $Cu^{2+}$ | 16.0 | 7.0 |
| CPG | phenethyl-methyl-NH—N-aminoethyl | — | 35.0 | 5.1 |

TABLE 3-continued

Performance of immobilised CalB on amino-functionalised supports chelated with various metals. Immobilised yield is based on the activity of supernatants after immobilization for the hydrolysis of 4-nitrophenyl acetate and conversion is based on the activity of the immobilised catalyst for the transesterification of (±)-1-phenylethanol with vinyl acetate. The CPS used in Table 3 is CPS Q30.

| Core | Functionalisation | Metal | Immobilised yield [%] | Conversion [%] |
|---|---|---|---|---|
| CPG | phenethyl-methyl-NH—N-aminoethyl + chelator | $Fe^{3+}$ | 19.9 | 5.5 |
| CPG | phenethyl-methyl-NH—N-aminoethyl + chelator | $Zn^{2+}$ | 47.8 | 10.1 |
| CPG | phenethyl-methyl-NH—N-aminoethyl + chelator | $Ni^{2+}$ | 21.7 | 7.8 |
| CPG | phenethyl-methyl-NH—N-aminoethyl + chelator | $Mg^{2+}$ | 20.3 | 5.5 |
| CPG | phenethyl-methyl-NH—N-aminoethyl + chelator | $Cu^{2+}$ | 32.0 | 7.7 |
| CPG | phenethyl-methyl-NH—N-aminoethyl + chelator | — | 25.7 | 7.3 |
| CPS | phenethyl-methyl-NH—N-aminoethyl | $Fe^{3+}$ | 51.3 | 12.0 |
| CPS | phenethyl-methyl-NH—N-aminoethyl | $Zn^{2+}$ | 65.0 | 14.5 |
| CPS | phenethyl-methyl-NH—N-aminoethyl | $Ni^{2+}$ | 56.4 | 13.0 |
| CPS | phenethyl-methyl-NH—N-aminoethyl | $Mg^{2+}$ | 30.4 | 11.4 |
| CPS | phenethyl-methyl-NH—N-aminoethyl | $Cu^{2+}$ | 22.6 | 11.8 |
| CPS | phenethyl-methyl-NH—N-aminoethyl | — | 6.0 | 7.4 |
| CPS | phenethyl-methyl-NH—N-aminoethyl + chelator | $Fe^{3+}$ | 53.8 | 10.5 |
| CPS | phenethyl-methyl-NH—N-aminoethyl + chelator | $Zn^{2+}$ | 51.0 | 12.2 |
| CPS | phenethyl-methyl-NH—N-aminoethyl + chelator | $Ni^{2+}$ | 52.6 | 11.6 |
| CPS | phenethyl-methyl-NH—N-aminoethyl + chelator | $Mg^{2+}$ | 19.6 | 8.7 |
| CPS | phenethyl-methyl-NH—N-aminoethyl + chelator | $Cu^{2+}$ | 47.2 | 11.2 |
| CPS | phenethyl-methyl-NH—N-aminoethyl + chelator | — | 23.2 | 8.4 |
| CPG | propyl-NH—N-aminohexyl | $Fe^{3+}$ | 17.8 | 5.9 |
| CPG | propyl-NH—N-aminohexyl | $Zn^{2+}$ | 63.5 | 18.6 |
| CPG | propyl-NH—N-aminohexyl | $Ni^{2+}$ | 17.8 | 5.3 |
| CPG | propyl-NH—N-aminohexyl | $Mg^{2+}$ | 14.1 | 6.2 |
| CPG | propyl-NH—N-aminohexyl | $Cu^{2+}$ | 16.7 | 5.3 |
| CPG | propyl-NH—N-aminohexyl | — | 12.2 | 5.6 |
| CPG | propyl-NH—N-aminohexyl + chelator | $Fe^{3+}$ | 20.4 | 6.9 |
| CPG | propyl-NH—N-aminohexyl + chelator | $Zn^{2+}$ | 54.9 | 16.1 |
| CPG | propyl-NH—N-aminohexyl + chelator | $Ni^{2+}$ | 9.3 | 7.0 |
| CPG | propyl-NH—N-aminohexyl + chelator | $Mg^{2+}$ | 13.8 | 6.2 |
| CPG | propyl-NH—N-aminohexyl + chelator | $Cu^{2+}$ | 14.2 | 8.3 |
| CPG | propyl-NH—N-aminohexyl + chelator | — | 2.2 | 5.8 |
| CPS | propyl-NH—N-aminohexyl | $Fe^{3+}$ | 35.1 | 11.2 |
| CPS | propyl-NH—N-aminohexyl | $Zn^{2+}$ | 83.8 | 19.8 |
| CPS | propyl-NH—N-aminohexyl | $Ni^{2+}$ | 6.1 | 9.4 |
| CPS | propyl-NH——N-aminohexyl | $Mg^{2+}$ | 17.7 | 9.5 |
| CPS | propyl-NH—N-aminohexyl | $Cu^{2+}$ | 6.2 | 8.4 |
| CPS | propyl-NH—N-aminohexyl | — | 0.0 | 6.5 |
| CPS | propyl-NH—N-aminohexyl + chelator | $Fe^{3+}$ | 51.0 | 11.9 |
| CPS | propyl-NH—N-aminohexyl + chelator | $Zn^{2+}$ | 67.4 | 16.4 |
| CPS | propyl-NH—N-aminohexyl + chelator | $Ni^{2+}$ | 38.5 | 11.8 |
| CPS | propyl-NH—N-aminohexyl + chelator | $Mg^{2+}$ | 34.1 | 10.5 |
| CPS | propyl-NH—N-aminohexyl + chelator | $Cu^{2+}$ | 34.5 | 11.9 |
| CPS | propyl-NH—N-aminohexyl + chelator | — | 40.1 | 11.0 |
| CPG | LCAA | $Fe^{3+}$ | 43.6 | 5.7 |
| CPG | LCAA | $Zn^{2+}$ | 56.6 | 10.0 |
| CPG | LCAA | $Ni^{2+}$ | 28.3 | 3.5 |
| CPG | LCAA | $Mg^{2+}$ | 31.7 | 4.1 |
| CPG | LCAA | $Cu^{2+}$ | 25.2 | 3.6 |
| CPG | LCAA | — | 20.3 | 3.5 |
| CPG | HybCPG VBC | $Fe^{3+}$ | 55.7 | 9.3 |
| CPG | HybCPG VBC | $Zn^{2+}$ | 60.3 | 11.2 |
| CPG | HybCPG VBC | $Ni^{2+}$ | 50.4 | 8.8 |
| CPG | HybCPG VBC | $Mg^{2+}$ | 31.1 | 9.6 |
| CPG | HybCPG VBC | $Cu^{2+}$ | 45.9 | 8.1 |
| CPG | HybCPG VBC | — | 39.1 | 8.2 |
| CPG | HybCPG copo | $Fe^{3+}$ | 63.8 | 9.6 |
| CPG | HybCPG copo | $Zn^{2+}$ | 45.5 | 8.9 |
| CPG | HybCPG copo | $Ni^{2+}$ | 50.5 | 8.3 |
| CPG | HybCPG copo | $Mg^{2+}$ | 50.6 | 8.0 |
| CPG | HybCPG copo | $Cu^{2+}$ | 31.2 | 8.1 |

TABLE 3-continued

Performance of immobilised CalB on amino-functionalised supports chelated with various metals. Immobilised yield is based on the activity of supernatants after immobilization for the hydrolysis of 4-nitrophenyl acetate and conversion is based on the activity of the immobilised catalyst for the transesterification of (±)-1-phenylethanol with vinyl acetate. The CPS used in Table 3 is CPS Q30.

| Core | Functionalisation | Metal | Immobilised yield [%] | Conversion [%] |
|---|---|---|---|---|
| CPG | HybCPG copo | — | 43.4 | 8.4 |
| ReliZyme | ethylamine | $Fe^{3+}$ | 23.9 | 0.8 |
| ReliZyme | ethylamine | $Zn^{2+}$ | 23.5 | 0.8 |
| ReliZyme | ethylamine | $Ni^{2+}$ | 4.1 | 0.8 |
| ReliZyme | ethylamine | $Mg^{2+}$ | 10.9 | 0.6 |
| ReliZyme | ethylamine | $Cu^{2+}$ | 0.0 | 1.1 |
| ReliZyme | ethylamine | — | 0.0 | 0.7 |
| ReliZyme | ethylamine + chelator | $Fe^{3+}$ | 0.0 | 2.2 |
| ReliZyme | ethylamine + chelator | $Zn^{2+}$ | 19.4 | 2.6 |
| ReliZyme | ethylamine + chelator | $Ni^{2+}$ | 2.4 | 2.8 |
| ReliZyme | ethylamine + chelator | $Mg^{2+}$ | 0.0 | 1.7 |
| ReliZyme | ethylamine + chelator | $Cu^{2+}$ | 5.3 | 4.0 |
| ReliZyme | ethylamine + chelator | — | 0.0 | 1.8 |
| ReliZyme | hexylamine | $Fe^{3+}$ | 20.9 | 1.1 |
| ReliZyme | hexylamine | $Zn^{2+}$ | 23.8 | 0.9 |
| ReliZyme | hexylamine | $Ni^{2+}$ | 10.4 | 0.9 |
| ReliZyme | hexylamine | $Mg^{2+}$ | 0.0 | 0.7 |
| ReliZyme | hexylamine | $Cu^{2+}$ | 2.5 | 0.9 |
| ReliZyme | hexylamine | — | 0.0 | 0.6 |
| ReliZyme | hexylamine + chelator | $Fe^{3+}$ | 9.4 | 3.0 |
| ReliZyme | hexylamine + chelator | $Zn^{2+}$ | 24.2 | 3.4 |
| ReliZyme | hexylamine + chelator | $Ni^{2+}$ | 5.1 | 2.8 |
| ReliZyme | hexylamine + chelator | $Mg^{2+}$ | 4.8 | 2.6 |
| ReliZyme | hexylamine + chelator | $Cu^{2+}$ | 0.0 | 2.4 |
| ReliZyme | hexylamine + chelator | — | 4.6 | 2.1 |
| Dowex | polyamine groups | $Fe^{3+}$ | 12.3 | 1.5 |
| Dowex | polyamine groups | $Zn^{2+}$ | 7.9 | 0.9 |
| Dowex | polyamine groups | $Ni^{2+}$ | 4.0 | 1.6 |
| Dowex | polyamine groups | $Mg^{2+}$ | 0.0 | 1.6 |
| Dowex | polyamine groups | $Cu^{2+}$ | 0.0 | 0.1 |
| Dowex | polyamine groups | — | 0.0 | 1.4 |
| Dowex | polyamine groups + chelator | $Fe^{3+}$ | 6.4 | 2.2 |
| Dowex | polyamine groups + chelator | $Zn^{2+}$ | 12.0 | 2.5 |
| Dowex | polyamine groups + chelator | $Ni^{2+}$ | 5.2 | 2.3 |
| Dowex | polyamine groups + chelator | $Mg^{2+}$ | 0.0 | 2.2 |
| Dowex | polyamine groups + chelator | $Cu^{2+}$ | 0.0 | 0.0 |
| Dowex | polyamine groups + chelator | — | 0.0 | 2.5 |

2.2 Immobilisation of TbSADH—N-His 2.2.1 Immobilisation

A freeze-dried powder of TbSADH—N-His (300 mg) was rehydrated in deionised water (8.61 mL) and diluted with 50 mM MOPS, 150 mM NaCl, pH 7 (21.39 mL) to obtain a cell-free extract containing 10 mg/mL (freeze-dried powder/total volume solution). The cell-free extract (500 μL) was transferred to a 96-well deep well plate containing the supports with freshly deposited metals and incubated for 2 h (1200 rpm, 25° C.). The supernatants were removed, and the immobilised supports were washed with 20 mM MOPS, pH 7.5 (2×1 mL) and used directly after removal of remaining buffer in the wells.

2.2.2 Determination of Immobilised Yield

The cell-free extract and supernatant from the immobilisations were diluted 8 times with 50 mM MOPS, 150 mM NaCl, pH 7. An aliquot of the diluted enzyme solution and supernatant (20 μL) was mixed with a reaction mixture (180 μL) containing 50 mM MOPS, pH 8, 1 mM $NADP^+$ and 100 mM 2-propanol. The formation of NADPH was measured by the absorbance ($A_{340}$) at 340 nm every 10 s for 3 minutes using a plate reader (Scheme 3). Rates of the reaction with each supernatant from immobilisations and fresh enzyme solution were extracted from linear regression of the data points ($A_{340}$/min). The immobilised yield was calculated by determining the percentage of enzymatic activity left in the supernatant after immobilisation compared to the enzymatic activity in the cell-free extract (Table 4). All the measurements were performed in duplicate and the result is presented as the average of the individual samples.

Scheme 3.

Oxidation of 2-propanol (100 mM) and NADPH formation by TbSADH for immobilised yield determination.

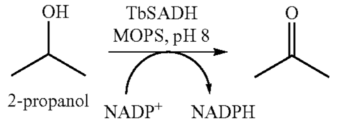

2-propanol

2.2.3 Activity of Immobilised Catalyst in Aqueous Medium

The activity of the heterogenous catalysts was determined by their ability to convert phenoxy-2-propanone to 1-phenoxy-2-propanol in the presence NADPH as hydride donor. 2-Propanol was added to regenerate $NADP^+$ to NADPH (Scheme 4). A reaction mixture (1 mL) containing 20 mM phenoxy-2-propanone, 1 mM $NADP^+$ and 10% (v/v) 2-propanol in 20 mM MOPS, pH 7.5 was added to the immobilised catalysts and the mixture was incubated for 1 h (1500 rpm, 30° C.). After stopping the mixing and allowing the catalyst to settle, an aliquot of the supernatant (500 μL) was added to EtOAc (500 μL) and the reaction was extracted for 5 min (1500 rpm, 25° C.). The 96-well deep well plate was left standing for 5 min to promote phase separation. The organic layer (200 μL) was transferred to another plate and dried over $Na_2SO_4$. An aliquot of the dried organic layer (100 μL) was added to EtOAc (900 μL) and analysed by GC-FID to determine the conversion of phenoxy-2-propanone (Table 4). All the measurements were performed in duplicate and the result is presented as the average of the individual samples.

Scheme 4.
Reduction of phenoxy-2-propane (20 mM) catalysed by immobilised TbSADH using 2-propanol (10% v/v) for cofactor regeneration.

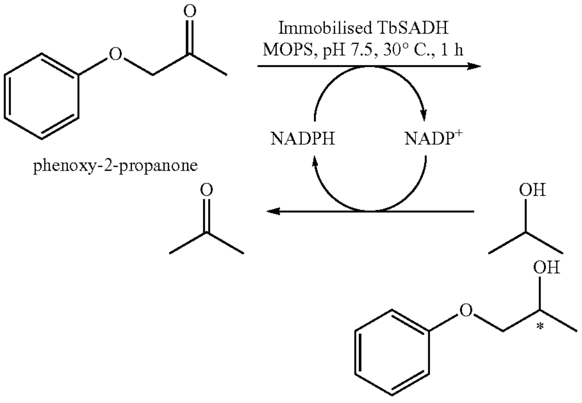

phenoxy-2-propanone phenoxy-2-propanol

TABLE 4

Performance of immobilised TbSADH-N-His on amino-functionalised supports chelated with various metals. Immobilised yield is based on the activity of supernatants after immobilization for the oxidation of 2-propanol and conversion is based on the activity of the immobilised catalyst for the reduction of phenoxy-2-propanone. The CPS used in Table 4 is CPS Q30.

| Core | Functionalisation | Metal | Immobilised yield [%] | Conversion [%] |
|---|---|---|---|---|
| CPG | propylamine | $Fe^{3+}$ | 61.5 | 33.5 |
| CPG | propylamine | $Zn^{2+}$ | 60.6 | 40.7 |
| CPG | propylamine | $Ni^{2+}$ | 35.2 | 24.6 |
| CPG | propylamine | $Mg^{2+}$ | 32.3 | 24.5 |
| CPG | propylamine | $Cu^{2+}$ | 99.6 | 5.7 |
| CPG | propylamine | — | 27.9 | 21.6 |
| CPS | propylamine | $Fe^{3+}$ | 83.0 | 37.3 |
| CPS | propylamine | $Zn^{2+}$ | 89.1 | 56.0 |
| CPS | propylamine | $Ni^{2+}$ | 71.9 | 36.2 |
| CPS | propylamine | $Mg^{2+}$ | 66.1 | 33.5 |
| CPS | propylamine | $Cu^{2+}$ | 100.0 | 5.1 |
| CPS | propylamine | — | 60.5 | 30.1 |
| CPG | propylNH—N-aminoethyl | $Fe^{3+}$ | 55.1 | 33.2 |
| CPG | propylNH—N-aminoethyl | $Zn^{2+}$ | 57.5 | 48.8 |
| CPG | propylNH—N-aminoethyl | $Ni^{2+}$ | 64.3 | 35.3 |
| CPG | propylNH—N-aminoethyl | $Mg^{2+}$ | 54.2 | 32.8 |
| CPG | propylNH—N-aminoethyl | $Cu^{2+}$ | 92.7 | 23.2 |
| CPG | propylNH—N-aminoethyl | — | 37.8 | 23.8 |
| CPS | propylNH—N-aminoethyl | $Fe^{3+}$ | 62.7 | 33.6 |
| CPS | propylNH—N-aminoethyl | $Zn^{2+}$ | 51.4 | 53.9 |
| CPS | propylNH—N-aminoethyl | $Ni^{2+}$ | 56.3 | 29.0 |
| CPS | propylNH—N-aminoethyl | $Mg^{2+}$ | 67.8 | 34.9 |
| CPS | propylNH—N-aminoethyl | $Cu^{2+}$ | 77.9 | 25.3 |
| CPS | propylNH—N-aminoethyl | — | 50.3 | 24.9 |
| CPG | phenethyl-methyl-NH—N-aminoethyl | $Fe^{3+}$ | 59.0 | 44.3 |

TABLE 4-continued

Performance of immobilised TbSADH-N-His on amino-functionalised supports chelated with various metals. Immobilised yield is based on the activity of supernatants after immobilization for the oxidation of 2-propanol and conversion is based on the activity of the immobilised catalyst for the reduction of phenoxy-2-propanone. The CPS used in Table 4 is CPS Q30.

| Core | Functionalisation | Metal | Immobilised yield [%] | Conversion [%] |
|---|---|---|---|---|
| CPG | phenethyl-methyl-NH—N-aminoethyl | $Zn^{2+}$ | 70.9 | 56.2 |
| CPG | phenethyl-methyl-NH—N-aminoethyl | $Ni^{2+}$ | 62.1 | 44.1 |
| CPG | phenethyl-methyl-NH—N-aminoethyl | $Mg^{2+}$ | 46.9 | 42.6 |
| CPG | phenethyl-methyl-NH—N-aminoethyl | $Cu^{2+}$ | 71.1 | 37.3 |
| CPG | phenethyl-methyl-NH—N-aminoethyl | — | 47.6 | 39.5 |
| CPS | phenethyl-methyl-NH—N-aminoethyl | $Fe^{3+}$ | 52.5 | 33.1 |
| CPS | phenethyl-methyl-NH—N-aminoethyl | $Zn^{2+}$ | 36.0 | 43.3 |
| CPS | phenethyl-methyl-NH—N-aminoethyl | $Ni^{2+}$ | 43.3 | 30.9 |
| CPS | phenethyl-methyl-NH—N-aminoethyl | $Mg^{2+}$ | 43.6 | 29.1 |
| CPS | phenethyl-methyl-NH—N-aminoethyl | $Cu^{2+}$ | 58.5 | 27.9 |
| CPS | phenethyl-methyl-NH—N-aminoethyl | — | 42.7 | 29.4 |
| CPG | propyl-NH—N-aminohexyl | $Fe^{3+}$ | 43.2 | 36.6 |
| CPG | propyl-NH—N-aminohexyl | $Zn^{2+}$ | 61.4 | 50.2 |
| CPG | propyl-NH—N-aminohexyl | $Ni^{2+}$ | 42.5 | 37.4 |
| CPG | propyl-NH—N-aminohexyl | $Mg^{2+}$ | 40.8 | 38.6 |
| CPG | propyl-NH—N-aminohexyl | $Cu^{2+}$ | 99.2 | 11.0 |
| CPG | propyl-NH—N-aminohexyl | — | 32.5 | 36.3 |
| CPS | propyl-NH—N-aminohexyl | $Fe^{3+}$ | 64.0 | 40.8 |
| CPS | propyl-NH—N-aminohexyl | $Zn^{2+}$ | 68.7 | 55.8 |
| CPS | propyl-NH—N-aminohexyl | $Ni^{2+}$ | 62.2 | 42.8 |
| CPS | propyl-NH—N-aminohexyl | $Mg^{2+}$ | 60.0 | 43.0 |
| CPS | propyl-NH—N-aminohexyl | $Cu^{2+}$ | 99.6 | 6.3 |
| CPS | propyl-NH—N-aminohexyl | — | 51.6 | 41.1 |
| CPG | LCAA | $Fe^{3+}$ | 41.4 | 32.9 |
| CPG | LCAA | $Zn^{2+}$ | 18.0 | 50.3 |
| CPG | LCAA | $Ni^{2+}$ | 32.8 | 30.7 |
| CPG | LCAA | $Mg^{2+}$ | 33.6 | 32.2 |
| CPG | LCAA | $Cu^{2+}$ | 49.0 | 26.2 |
| CPG | LCAA | — | 36.3 | 29.4 |
| CPG | HybCPG VBC | $Fe^{3+}$ | 95.1 | 44.7 |
| CPG | HybCPG VBC | $Zn^{2+}$ | 92.3 | 60.7 |
| CPG | HybCPG VBC | $Ni^{2+}$ | 93.8 | 44.3 |
| CPG | HybCPG VBC | $Mg^{2+}$ | 94.4 | 44.5 |
| CPG | HybCPG VBC | $Cu^{2+}$ | 99.6 | 22.1 |
| CPG | HybCPG VBC | — | 94.8 | 44.8 |
| CPG | HybCPG copo | $Fe^{3+}$ | 88.9 | 43.6 |
| CPG | HybCPG copo | $Zn^{2+}$ | 84.3 | 61.4 |
| CPG | HybCPG copo | $Ni^{2+}$ | 90.0 | 44.4 |
| CPG | HybCPG copo | $Mg^{2+}$ | 85.4 | 43.3 |
| CPG | HybCPG copo | $Cu^{2+}$ | 94.1 | 31.7 |
| CPG | HybCPG copo | — | 85.7 | 42.5 |
| ReliZyme | ethylamine | $Fe^{3+}$ | 35.1 | 10.5 |
| ReliZyme | ethylamine | $Zn^{2+}$ | 0.0 | 14.2 |
| ReliZyme | ethylamine | $Ni^{2+}$ | 21.8 | 9.8 |
| ReliZyme | ethylamine | $Mg^{2+}$ | 26.3 | 9.3 |
| ReliZyme | ethylamine | $Cu^{2+}$ | 53.6 | 6.0 |
| ReliZyme | ethylamine | — | 29.4 | 7.0 |
| ReliZyme | hexylamine | $Fe^{3+}$ | 40.0 | 12.8 |
| ReliZyme | hexylamine | $Zn^{2+}$ | 33.0 | 12.1 |
| ReliZyme | hexylamine | $Ni^{2+}$ | 31.8 | 11.9 |
| ReliZyme | hexylamine | $Mg^{2+}$ | 27.4 | 11.7 |
| ReliZyme | hexylamine | $Cu^{2+}$ | 47.5 | 7.2 |
| ReliZyme | hexylamine | — | 33.6 | 10.7 |
| Dowex | polyamine groups | $Fe^{3+}$ | 34.6 | 1.5 |
| Dowex | polyamine groups | $Zn^{2+}$ | 30.5 | 1.6 |
| Dowex | polyamine groups | $Ni^{2+}$ | 31.3 | 1.7 |
| Dowex | polyamine groups | $Mg^{2+}$ | 28.0 | 1.4 |
| Dowex | polyamine groups | $Cu^{2+}$ | 25.6 | 1.5 |
| Dowex | polyamine groups | — | 31.0 | 1.4 |

2.4 Immobilisation of Non His-Tagged Enzymes—Lipase from *Candida* sp.

2.4.1 Immobilisation

Commercial Lipase solution from *Candida* sp. was diluted four times in 20 mM MOPS pH 7.5. The enzyme solution (500 μL) was transferred to a 96-well deep well plate containing the supports with freshly deposited metals and incubated for 2 h (1200 rpm, 25° C.). The supernatants were removed, and the immobilised supports were washed with 20 mM MOPS, pH 7.5 (2×1 mL). The catalysts were dried under vacuum in a desiccator overnight.

2.4.2 Determination of Immobilised Yield

The enzyme solution and supernatant from the immobilisations were diluted 400 times in 20 mM MOPS, pH 7.5. An aliquot of the diluted enzyme solution and supernatant (30 μL) was mixed with a reaction mixture (170 μL) containing 20 mM MOPS, pH 7.5 and 3 mM 4-nitrophenyl acetate in acetonitrile. The formation of 4-nitrophenol was measured by the absorbance ($A_{410}$) at 410 nm every 10 s for 3 minutes using a plate reader (Scheme 1). Rates of the reaction with each supernatant from immobilisations and fresh enzyme solution were extracted from linear regression of the data points ($A_{410}$/min). The immobilised yield was calculated by determining the percentage of enzymatic activity left in the supernatant after immobilisation compared to the enzymatic activity in the cell-free extract (Table 5). All the measurements were performed in duplicate and the result is presented as the average of the individual samples.

2.4.3 Activity of Immobilised Catalyst in Organic Solvent

The activity of the heterogeneous catalysts was determined by their ability to convert (±)-1-phenylethanol and vinyl acetate to (R)-phenylethyl acetate (Scheme 5). A reaction mixture (1 mL) containing 2 M (±)-1-phenylethanol, 1.2 M vinyl acetate and 1% (v/v) dodecane (internal standard) in MTBE was added to the immobilised catalyst and the mixture was incubated for 3 h (1200 rpm, 25° C.). After stopping the mixing and allowing the catalyst to settle, an aliquot of the supernatant (10 μL) was added to EtOAc (990 μL) and analysed by GC-FID to determine the conversion of (±)-1-phenylethanol (Table 5). All the measurements were performed in duplicate and the result is presented as the average of the individual samples. For comparison purposes, supports without amino-functionalisation were also included in reaction screening for this enzyme.

Scheme 5.

Transesterification of (±)-1-phenylethanol (2M) with vinyl acetate (1.2M) catalysed by immobilised lipase from *Candida* sp.

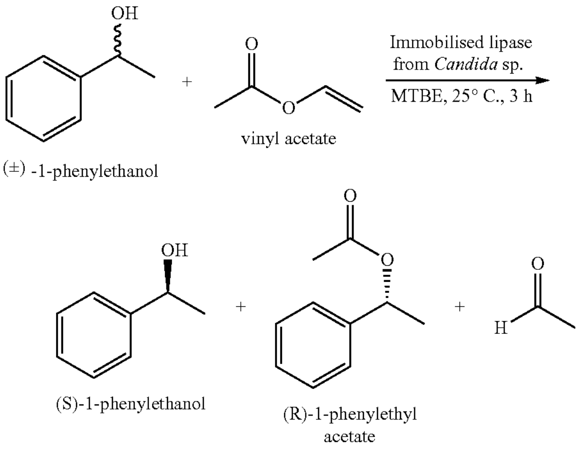

TABLE 5

Performance of immobilised Lipase from *Candida* sp. on amino-functionalised supports chelated with various metals. Immobilised yield is based on the activity of supernatants after immobilization for the hydrolysis of 4-nitrophenyl acetate and conversion is based on the activity of the immobilised catalyst for the transesterification of (±)-1-phenylethanol with vinyl acetate. The CPS used in Table 6 is CPS Q30.

| Core | Functionalisation | Metal | Immobilised yield [%] | Conversion [%] |
|---|---|---|---|---|
| CPG | propylamine | $Fe^{3+}$ | 42.4 | 6.9 |
| CPG | propylamine | $Zn^{2+}$ | 45.3 | 10.4 |
| CPG | propylamine | $Ni^{2+}$ | 35.0 | 8.3 |
| CPG | propylamine | $Mg^{2+}$ | 33.3 | 7.1 |
| CPG | propylamine | $Cu^{2+}$ | 47.0 | 6.1 |
| CPG | propylamine | — | 33.6 | 5.1 |
| CPS | propylamine | $Fe^{3+}$ | 2.8 | 5.5 |
| CPS | propylamine | $Zn^{2+}$ | 0.9 | 3.4 |
| CPS | propylamine | $Ni^{2+}$ | 0.0 | 3.4 |
| CPS | propylamine | $Mg^{2+}$ | 4.2 | 4.0 |
| CPS | propylamine | $Cu^{2+}$ | 0.0 | 3.3 |
| CPS | propylamine | — | 5.9 | 2.8 |
| CPG | propylNH—N-aminoethyl | $Fe^{3+}$ | 46.0 | 7.8 |
| CPG | propylNH—N-aminoethyl | $Zn^{2+}$ | 43.9 | 5.8 |
| CPG | propylNH—N-aminoethyl | $Ni^{2+}$ | 33.6 | 5.3 |
| CPG | propylNH—N-aminoethyl | $Mg^{2+}$ | 39.6 | 4.7 |
| CPG | propylNH—N-aminoethyl | $Cu^{2+}$ | 45.8 | 5.2 |
| CPG | propylNH—N-aminoethyl | — | 37.3 | 5.2 |
| CPS | propylNH—N-aminoethyl | $Fe^{3+}$ | 2.3 | 2.9 |
| CPS | propylNH—N-aminoethyl | $Zn^{2+}$ | 2.8 | 2.6 |
| CPS | propylNH—N-aminoethyl | $Ni^{2+}$ | 0.0 | 3.2 |
| CPS | propylNH—N-aminoethyl | $Mg^{2+}$ | 0.5 | 2.8 |
| CPS | propylNH—N-aminoethyl | $Cu^{2+}$ | 0.0 | 3.0 |
| CPS | propylNH—N-aminoethyl | — | 0.0 | 2.6 |
| CPG | phenethyl-methyl-NH—N-aminoethyl | $Fe^{3+}$ | 63.3 | 27.2 |
| CPG | phenethyl-methyl-NH—N-aminoethyl | $Zn^{2+}$ | 54.8 | 22.5 |
| CPG | phenethyl-methyl-NH—N-aminoethyl | $Ni^{2+}$ | 61.3 | 24.6 |

TABLE 5-continued

Performance of immobilised Lipase from *Candida* sp. on amino-functionalised supports chelated with various metals. Immobilised yield is based on the activity of supernatants after immobilization for the hydrolysis of 4-nitrophenyl acetate and conversion is based on the activity of the immobilised catalyst for the transesterification of (±)-1-phenylethanol with vinyl acetate. The CPS used in Table 6 is CPS Q30.

| Core | Functionalisation | Metal | Immobilised yield [%] | Conversion [%] |
|---|---|---|---|---|
| CPG | phenethyl-methyl-NH—N-aminoethyl | $Mg^{2+}$ | 45.7 | 23.0 |
| CPG | phenethyl-methyl-NH—N-aminoethyl | $Cu^{2+}$ | 59.0 | 24.3 |
| CPG | phenethyl-methyl-NH—N-aminoethyl | — | 46.5 | 21.9 |
| CPS | phenethyl-methyl-NH—N-aminoethyl | $Fe^{3+}$ | 65.7 | 41.6 |
| CPS | phenethyl-methyl-NH—N-aminoethyl | $Zn^{2+}$ | 32.3 | 32.3 |
| CPS | phenethyl-methyl-NH—N-aminoethyl | $Ni^{2+}$ | 43.8 | 36.3 |
| CPS | phenethyl-methyl-NH—N-aminoethyl | $Mg^{2+}$ | 42.6 | 34.9 |
| CPS | phenethyl-methyl-NH—N-aminoethyl | $Cu^{2+}$ | 50.9 | 36.8 |
| CPS | phenethyl-methyl-NH—N-aminoethyl | — | 26.3 | 32.5 |
| CPG | propyl-NH—N-aminohexyl | $Fe^{3+}$ | 43.1 | 6.2 |
| CPG | propyl-NH—N-aminohexyl | $Zn^{2+}$ | 47.1 | 3.8 |
| CPG | propyl-NH—N-aminohexyl | $Ni^{2+}$ | 27.8 | 5.8 |
| CPG | propyl-NH—N-aminohexyl | $Mg^{2+}$ | 30.8 | 5.0 |
| CPG | propyl-NH—N-aminohexyl | $Cu^{2+}$ | 43.6 | 5.5 |
| CPG | propyl-NH—N-aminohexyl | — | 29.9 | 4.1 |
| CPS | propyl-NH—N-aminohexyl | $Fe^{3+}$ | 1.5 | 3.0 |
| CPS | propyl-NH—N-aminohexyl | $Zn^{2+}$ | 0.0 | 3.1 |
| CPS | propyl-NH—N-aminohexyl | $Ni^{2+}$ | 0.0 | 3.5 |
| CPS | propyl-NH—N-aminohexyl | $Mg^{2+}$ | 4.1 | 3.0 |
| CPS | propyl-NH—N-aminohexyl | $Cu^{2+}$ | 0.0 | 3.9 |
| CPS | propyl-NH—N-aminohexyl | — | 0.0 | 3.0 |
| CPG | — | $Fe^{3+}$ | 44.7 | 17.1 |
| CPG | — | $Zn^{2+}$ | 41.2 | 10.5 |
| CPG | — | $Ni^{2+}$ | 43.3 | 8.5 |
| CPG | — | $Mg^{2+}$ | 37.4 | 11.3 |
| CPG | — | $Cu^{2+}$ | 43.3 | 19.7 |
| CPG | — | — | 48.5 | 10.9 |
| CPS | — | $Fe^{3+}$ | 42.3 | 27.8 |
| CPS | — | $Zn^{2+}$ | 37.0 | 24.0 |
| CPS | — | $Ni^{2+}$ | 31.0 | 22.6 |
| CPS | — | $Mg^{2+}$ | 25.6 | 21.2 |
| CPS | — | $Cu^{2+}$ | 47.6 | 27.2 |
| CPS | — | — | 57.8 | 25.3 |
| CPG | LCAA | — | 21.0 | 6.2 |
| CPG | HybCPG VBC | — | 62.8 | 23.5 |
| CPG | HybCPG copo | — | 56.2 | 26.4 |

2.5 Immobilisation of Non His-Tagged Enzymes—Lipase from *Aspergillus oryzae*

2.5.1 Immobilisation

Commercial Lipase solution from *Aspergillus oryzae* was diluted two times in deionised water and the enzyme solution (500 μL) was transferred to a 96-well deep well plate containing the supports with freshly deposited metals and incubated for 2 h (1200 rpm, 25° C.). The supernatants were removed, and the immobilised supports were washed with 50 mM HEPES, 50 mM ammonium acetate, 10 mM $CaCl_2$, pH 7 solution (2×1 mL), followed by wash with 50 mM HEPES, 50 mM ammonium acetate, 10 mM $CaCl_2$, 130 mM sucrose, pH 7 solution (1×1 mL). The catalysts were dried under vacuum in a desiccator overnight.

2.5.2 Determination of Immobilised Yield

The enzyme solution and supernatant from the immobilisations were diluted 10 times with deionised water. The absorbance ($A_{280}$) of an aliquot of the diluted enzyme solution and supernatant (200 μL) was measured at 280 nm using a plate reader. The immobilised yield was calculated by determining the absorbance (correlated to the amount of protein present in solution) in the supernatant after immobilisation compared to the absorbance in the initial enzyme solution (Table 6).

2.5.3 Activity of Immobilised Catalyst in Organic Solvent

The activity of the heterogeneous catalysts was determined by their ability to convert (±)-1-phenylethanol and vinyl acetate to (R)-phenylethyl acetate (Scheme 6). A reaction mixture (1 mL) containing 2 M (±)-1-phenylethanol. 1.2 M vinyl acetate and 1% (v/v) dodecane (internal standard) in MTBE was added to the immobilised catalyst and the mixture was incubated for 2 h (1200 rpm, 25° C.). After stopping the mixing and allowing the catalyst to settle, an aliquot of the supernatant (10 μL) was added to EtOAc (990 μL) and analysed by GC-FID to determine the conversion of (±)-1-phenylethanol (Table 6). All the measurements were performed in duplicate and the result is presented as the average of the individual samples. For comparison purposes, supports without amino-functionalisation were also included in reaction screening for this enzyme.

Scheme 6.

Transesterification of (±)-1-phenylethanol (2M) with vinyl acetate (1.2M) catalysed by immobilised lipase from *Aspergillus oryzae*.

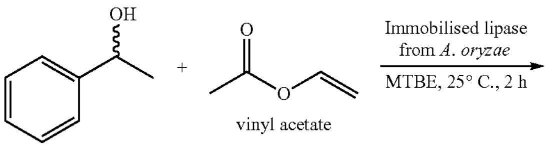

vinyl acetate (±)-1-phenylethanol

-continued

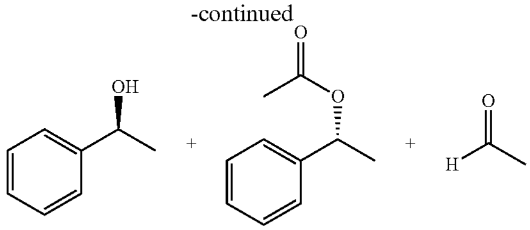

(S)-1-phenylethanol (R)-1-phenylethyl acetate

TABLE 6

Performance of immobilised Lipase from *Aspergillus oryzae* on amino-functionalised supports chelated with various metals. Immobilised yield is based on the absorbance ($A_{280}$) of supernatants after immobilization and conversion is based on the activity of the immobilised catalyst for the transesterification of (±)-1-phenylethanol with vinyl acetate. The CPS used in Table 7 is CPS Q30.

| Core | Functionalisation | Metal | Immobilised yield [%] | Conversion [%] |
|---|---|---|---|---|
| CPG | propylamine | $Fe^{3+}$ | 28.7 | 29.0 |
| CPG | propylamine | $Zn^{2+}$ | 21.4 | 30.0 |
| CPG | propylamine | $Ni^{2+}$ | 25.2 | 28.3 |
| CPG | propylamine | $Mg^{2+}$ | 22.2 | 29.6 |
| CPG | propylamine | $Cu^{2+}$ | 22.8 | 28.2 |
| CPG | propylamine | — | 23.5 | 30.1 |
| CPS | propylamine | $Fe^{3+}$ | 30.6 | 28.5 |
| CPS | propylamine | $Zn^{2+}$ | 31.2 | 29.1 |
| CPS | propylamine | $Ni^{2+}$ | 28.1 | 28.1 |
| CPS | propylamine | $Mg^{2+}$ | 26.4 | 28.2 |
| CPS | propylamine | $Cu^{2+}$ | 27.0 | 27.5 |
| CPS | propylamine | — | 33.1 | 27.9 |
| CPG | propylNH—N-aminoethyl | $Fe^{3+}$ | 28.2 | 31.5 |
| CPG | propylNH—N-aminoethyl | $Zn^{2+}$ | 20.2 | 32.6 |
| CPG | propylNH—N-aminoethyl | $Ni^{2+}$ | 23.7 | 31.3 |
| CPG | propylNH—N-aminoethyl | $Mg^{2+}$ | 19.5 | 31.7 |
| CPG | propylNH—N-aminoethyl | $Cu^{2+}$ | 20.6 | 31.5 |
| CPG | propylNH—N-aminoethyl | — | 20.3 | 31.9 |
| CPS | propylNH—N-aminoethyl | $Fe^{3+}$ | 28.1 | 30.4 |
| CPS | propylNH—N-aminoethyl | $Zn^{2+}$ | 21.8 | 31.6 |
| CPS | propylNH—N-aminoethyl | $Ni^{2+}$ | 22.6 | 30.7 |
| CPS | propylNH—N-aminoethyl | $Mg^{2+}$ | 25.5 | 30.9 |
| CPS | propylNH—N-aminoethyl | $Cu^{2+}$ | 27.4 | 30.3 |
| CPS | propylNH—N-aminoethyl | — | 25.1 | 30.7 |
| CPG | phenetyl-methyl-NH—N-aminoethyl | $Fe^{3+}$ | 23.5 | 26.6 |
| CPG | phenethyl-methyl-NH—N-aminoethyl | $Zn^{2+}$ | 17.9 | 26.6 |
| CPG | phenethyl-methyl-NH—N-aminoethyl | $Ni^{2+}$ | 25.2 | 25.4 |
| CPG | phenethyl-methyl-NH—N-aminoethyl | $Mg^{2+}$ | 20.0 | 26.3 |
| CPG | phenethyl-methyl-NH—N-aminoethyl | $Cu^{2+}$ | 18.6 | 25.6 |
| CPG | phenethyl-methyl-NH—N-aminoethyl | — | 18.9 | 26.1 |
| CPS | phenethyl-methyl-NH—N-aminoethyl | $Fe^{3+}$ | 29.7 | 28.2 |
| CPS | phenethyl-methyl-NH—N-aminoethyl | $Zn^{2+}$ | 18.5 | 24.9 |
| CPS | phenethyl-methyl-NH—N-aminoethyl | $Ni^{2+}$ | 23.1 | 25.3 |
| CPS | phenethyl-methyl-NH—N-aminoethyl | $Mg^{2+}$ | 22.8 | 25.2 |
| CPS | phenethyl-methyl-NH—N-aminoethyl | $Cu^{2+}$ | 26.6 | 26.0 |
| CPS | phenethyl-methyl-NH—N-aminoethyl | — | 27.2 | 25.9 |
| CPG | propyl-NH—N-aminohexyl | $Fe^{3+}$ | 28.1 | 31.4 |
| CPG | propyl-NH—N-aminohexyl | $Zn^{2+}$ | 23.1 | 31.6 |
| CPG | propyl-NH—N-aminohexyl | $Ni^{2+}$ | 26.8 | 31.5 |
| CPG | propyl-NH—N-aminohexyl | $Mg^{2+}$ | 23.8 | 31.5 |
| CPG | propyl-NH—N-aminohexyl | $Cu^{2+}$ | 24.2 | 31.7 |
| CPG | propyl-NH—N-aminohexyl | — | 25.1 | 31.4 |
| CPS | propyl-NH—N-aminohexyl | $Fe^{3+}$ | 42.4 | 28.1 |
| CPS | propyl-NH—N-aminohexyl | $Zn^{2+}$ | 40.2 | 27.5 |
| CPS | propyl-NH—N-aminohexyl | $Ni^{2+}$ | 37.5 | 26.9 |
| CPS | propyl-NH—N-aminohexyl | $Mg^{2+}$ | 34.4 | 26.6 |
| CPS | propyl-NH—N-aminohexyl | $Cu^{2+}$ | 36.6 | 26.9 |
| CPS | propyl-NH—N-aminohexyl | — | 37.0 | 26.3 |
| CPG | — | $Fe^{3+}$ | 15.3 | 6.1 |
| CPG | — | $Zn^{2+}$ | 13.1 | 7.1 |
| CPG | — | $Ni^{2+}$ | 9.0 | 4.4 |
| CPG | — | $Mg^{2+}$ | 10.1 | 5.9 |
| CPG | — | $Cu^{2+}$ | 20.8 | 3.7 |
| CPG | — | — | 10.8 | 5.4 |

TABLE 6-continued

Performance of immobilised Lipase from *Aspergillus oryzae* on amino-functionalised supports chelated with various metals. Immobilised yield is based on the absorbance ($A_{280}$) of supernatants after immobilization and conversion is based on the activity of the immobilised catalyst for the transesterification of (±)-1-phenylethanol with vinyl acetate. The CPS used in Table 7 is CPS Q30.

| Core | Functionalisation | Metal | Immobilised yield [%] | Conversion [%] |
|---|---|---|---|---|
| CPS | — | $Fe^{3+}$ | 25.0 | 21.5 |
| CPS | — | $Zn^{2+}$ | 16.7 | 22.6 |
| CPS | — | $Ni^{2+}$ | 15.3 | 20.0 |
| CPS | — | $Mg^{2+}$ | 16.1 | 20.5 |
| CPS | — | $Cu^{2+}$ | 21.5 | 19.4 |
| CPS | — | — | 15.7 | 18.9 |
| CPG | LCAA | — | 27.9 | 32.5 |
| CPG | HybCPG VBC | — | 36.1 | 27.5 |
| CPG | HybCPG copo | — | 30.8 | 27.1 |

2.6 Immobilisation of Non His-Tagged Enzymes—Lipozyme® TL 100L 2.6.1 Immobilisation of TLL on CPS Propylamine The solution of Lipozyme® TL 100L, containing *Thermomyces lanuginosus* lipase (TLL) was prepared for immobilisation by dilution of the commercial enzyme (60% v/v) in deionised water (pH 6.7 of final solution). Diluted enzyme (250 mL) was transferred to a 500 mL Duran bottle containing 50 g of support (CPS Q30 or Q50 functionalised with propylamine). Samples were incubated on a tilt/roller mixer for 1.5 h (70 rpm, 21° C.). After immobilisation the supernatants were removed and the immobilised supports were washed with 50 mM HEPES, 50 mM ammonium acetate, 10 mM $CaCl_2$, pH 7 solution (1×250 mL), followed by wash with 50 mM HEPES, 50 mM ammonium acetate, 10 mM $CaCl_2$, 130 mM sucrose, pH 7 solution (1×250 mL). For each washing step, the immobilised catalyst was mixed with the washing solution on a tilt/roller mixer for 3 min (70 rpm, 21° C.). The catalyst was filtered under vacuum to remove most of the washing solution (6 min), transferred to a 3 L glass flask and dried on a rotary evaporator for 115-120 min (40 mbar, 40° C.).

2.6.2 Immobilisation of TLL on CPS Phenethyl-Methyl-NH—N-Aminoethyl

The solution of Lipozyme® TL 100L, containing *Thermomyces lanuginosus* lipase (TLL) was prepared for immobilisation by dilution of the commercial enzyme (60% v/v) in deionised water (pH 6.7 of final solution). Diluted enzyme (100 mL) was transferred to a 250 mL Duran bottle containing 20 g of support (CPS Q50 functionalised with phenethyl-methyl-NH—N-aminoethyl). Samples were incubated on a tilt/roller mixer for 1.5 h (70 rpm, 21° C.). After immobilisation the supernatants were removed and the immobilised supports were washed with multiples solutions to find the most active immobilised preparation 50 mM HEPES, 50 mM ammonium acetate, 9 mM $CaCl_2$, pH 7 solution (3×100 mL). For each washing step, the immobilised catalyst was mixed with the washing solution on a tilt/roller mixer for 3 min (70 rpm, 21° C.). The catalyst was filtered under vacuum to remove most of the washing solution (45 min), transferred to a crystallising dish and dried under vacuum in a desiccator for 26 h.

2.6.3 Determination of Immobilised Yield

The enzyme solution and supernatant from the immobilisations were diluted 50 and 10 times, respectively, with deionised water. The absorbance ($A_{280}$) of an aliquot of the diluted enzyme solution and supernatant (200 μL) was measured at 280 nm using a plate reader. The immobilised yield was calculated by determining the absorbance (correlated to the amount of protein present in solution) in the supernatant after immobilisation compared to the absorbance in the initial enzyme solution (Table 7).

2.6.4 Activity of Immobilised Catalyst in Organic Solvent

The activity of the heterogeneous catalysts was determined by their ability to convert (±)-1-phenylethanol and vinyl acetate to (R)-phenylethyl acetate. A reaction mixture (1 mL) containing 2 M (±)-1-phenylethanol, 1.2 M vinyl acetate and 1% (v/v) dodecane (internal standard) in MTBE was added to a 1.5 mL Eppendorf tube containing the immobilised catalyst (10 mg) and the mixture was incubated for 30 min (1500 rpm, 35° C.). After stopping the mixing and allowing the catalyst to settle, an aliquot of the supernatant (10 μL) was added to MTBE (990 μL) and analysed by GC-FID to determine the conversion of (±)-1-phenylethanol (Table 7). All the measurements were performed in duplicate and the result is presented as the average of the individual samples. Activity of immobilised catalyst was compared to the commercial immobilised catalyst Lipozyme® TL IM from Novozymes (Table 7).

TABLE 7

Performance of immobilised Lipozyme ® TL 100L on amino-functionalised supports. Immobilised yield is based on the absorbance ($A_{280}$) of supernatants after immobilization and conversion is based on the activity of the immobilised catalyst for the transesterification of (±)-1-phenylethanol with vinyl acetate.

| TLL catalyst | Enzyme loading [$g_{immobilised\ enzyme}/g_{support}$] | Activity [$\mu mol\ h^{-1}\ mg^{-1}$] |
|---|---|---|
| CPS-Q50 phenethyl-methyl-NH—N-aminoethyl | 0.05 | 43.8 |
| CPS-Q30 propylamine | 0.06 | 56.0 |
| CPS-Q50 propylamine | 0.06 | 53.9 |
| Lipozyme ® TL IM | — | 14.3 |

2.6.5 Activity of Immobilised Catalyst for the Interesterification of Blended Soybean Oils The activity of the immobilised catalyst was also evaluated for the interesterification of a soybean oil blend composed of 60% refined and bleached soybean oil and 40% fully hydrogenated soybean oil supplied by Bunge (BG F41120-000 SOY SHTG) to yield a product with a lower end melting temperature. The melted soybean oil blend (500 μL) was added to a 2 mL Eppendorf tubes containing the immobilised TLL (15 mg) and incubated for 30 min (1500 rpm, 70° C.). After stopping the mixing and allowing the catalyst to settle, an aliquot of the oil (350 μL) was transferred to a 2 mL Eppendorf tube and placed on ice-cold water to allow fat solidification and subsequently stored in a freezer (−20° C.) for at least 1 h before being analysed. The analysis of the end of melting range for the sampled reactions were performed on a Melting Point System MP55 (Mettler Toledo) with capillary tubes (Hirschmann, L 75 mm, I.D 0.95 mm, O.D. 1.35 mm) using a heating rate of 2° C./min between 34° C.-67° C. recording the end of melt temperatures as the temperature where the intensity signal (transmittance) plateaus and no further increase in intensity was detected (Table 8). The end of melting range of initial soybean oil blend is 64.7° C., and lower end of melting range represents higher degree of the occurred interesterification reaction and thereby indicates a higher enzymatic activity.

TABLE 8

Performance of immobilised Lipozyme ® TL 100L on amino-functionalised supports and Lipozyme ® TL IM. Efficiency of catalyst in the interesterification of blended soybean oils is based on the end of melting range of the soybean oil blend after reaction.

| TLL catalyst | Enzyme loading [$g_{immobilised\ enzyme}/g_{support}$] | End of melting range [° C.] |
|---|---|---|
| CPS-Q50 phenethyl-methyl-NH—N-aminoethyl | 0.05 | 56.4 |
| CPS-Q30 propylamine | 0.06 | 55.1 |
| CPS-Q50 propylamine | 0.06 | 56.9 |
| Lipozyme ® TL IM | — | 62.4 |

Example 3 Screening of Different Silanes for Controlled Pore Silica Functionalisation 3.1 Synthesis of Various Amino-Functionalised Supports Using Controlled Pore Silica Syntheses of different amino-functionalised supports using controlled pore silica were carried out as previously described. A panel of structurally diverse amino-silanes was used as illustrated in Table 9.

TABLE 9

Silanes for amino-functionalisation of controlled pore silica.

| Silane | Amino-functionalisation | CAS number |
|---|---|---|
| N,N'-bis(2-hydroxyethyl)-N,N'-bis (trimethoxysilylpropyl)ethylenediamine | bis-propyl-N,N'-bis-(2-hydroxyethyl) ethylenediamine | 214362-07-9 |
| N-(2-aminoethyl)-3-aminopropyltrimethoxy-silanepropyltrimethoxysilane | co-polymer propyl + propylNH—N-aminoethyl | —* |
| Ureidopropyltriethoxysilane | propylNH—N-methanamide | 23779-32-0 |
| N-(3-triethoxysilylpropyl)-4,5-dihydroimidazole | propyl-3N-(4,5-dihydroimidazole) | 58068-97-6 |

*Oligomeric co-hydrolisate of N-(2-aminoethyl)-3-aminopropyltrimethoxysilane (CAS 1760-24-3) and n-propyltrimethoxy-silane (CAS 1067-25-0) purchased from Gelest (product code SIA0591.3).

3.2 Metal Deposition and Immobilisation

Procedures for metal deposition for the screening of different supports were performed as described previously. This set of experiments evaluated the presence and absence of $Zn^{2+}$ as metal. For CalB-N-His immobilisations, metal stock solution of 1.55 mM (300 IL) was added to the support to reach a final concentration of 0.93 mM in the well (Table 2). For Lipase from *Candida* sp. and TbSADH immobilisations, metal stock solutions of 0.26 mM (300 μL) were added to the support to reach a final concentration of 0.16 mM in the well (Table 2). Immobilisations of CalB-N-His, Lipase from *Candida* sp. and TbSADH were carried out as described in the previous sections (Results are presented in Tables 10-13). For comparison purposes, CPS without amino-functionalisation was also included in reaction screening for this set of experiment.

TABLE 10

Performance of immobilised CalB-N-His on amino-functionalised controlled porous silica. Immobilised yield is based on the activity of supernatants after immobilization for the hydrolysis of 4-nitrophenyl acetate and conversion is based on the activity of the immobilised catalyst for the transesterification of (±)-1-phenylethanol with vinyl acetate. The CPS used in Table 11 is CPS Q30.

| Core | Functionalisation | Metal | Immobilised yield [%] | Conversion [%] |
|---|---|---|---|---|
| CPS | bis-propyl-N,N'-bis-(2-hydroxyethyl) ethylenediamine | — | 0.0 | 3.6 |
| CPS | bis-propyl-N,N'-bis-(2-hydroxyethyl) ethylenediamine | $Zn^{2+}$ | 4.0 | 5.8 |
| CPS | co-polymer propyl + propylNH—N-aminoethyl | — | 7.3 | 6.0 |

TABLE 10-continued

Performance of immobilised CalB-N-His on amino-functionalised controlled porous silica. Immobilised yield is based on the activity of supernatants after immobilization for the hydrolysis of 4-nitrophenyl acetate and conversion is based on the activity of the immobilised catalyst for the transesterification of (±)-1-phenylethanol with vinyl acetate. The CPS used in Table 11 is CPS Q30.

| Core | Functionalisation | Metal | Immobilised yield [%] | Conversion [%] |
|---|---|---|---|---|
| CPS | co-polymer propyl + propylNH—N-aminoethyl | $Zn^{2+}$ | 36.2 | 11.5 |
| CPS | propylNH—N-methanamide | — | 2.1 | 4.9 |
| CPS | propylNH—N-methanamide | $Zn^{2+}$ | 0.0 | 5.6 |
| CPS | propyl-3N-(4,5-dihydroimidazole) | — | 4.0 | 4.5 |
| CPS | propyl-3N-(4,5-dihydroimidazole) | $Zn^{2+}$ | 59.4 | 16.0 |
| CPS | — | — | 27.6 | 10.4 |
| CPS | — | $Zn^{2+}$ | 47.0 | 13.1 |

TABLE 11

Performance of immobilised Lipase from *Candida* sp. on amino-functionalised controlled porous silica. Immobilised yield is based on the activity of supernatants after immobilization for the hydrolysis of 4-nitrophenyl acetate and conversion is based on the activity of the immobilised catalyst for the transesterification of (±)-1-phenylethanol with vinyl acetate. The CPS used in Table 12 is CPS Q30.

| Core | Functionalisation | Metal | Immobilised yield [%] | Conversion [%] |
|---|---|---|---|---|
| CPS | bis-propyl-N,N'-bis-(2-hydroxyethyl) ethylenediamine | — | 16.1 | 5.4 |
| CPS | bis-propyl-N,N'-bis-(2-hydroxyethyl) ethylenediamine | $Zn^{2+}$ | 9.1 | 5.6 |
| CPS | co-polymer propyl + propylNH—N-aminoethyl | — | 30.3 | 26.9 |
| CPS | co-polymer propyl + propylNH—N-aminoethyl | $Zn^{2+}$ | 33.7 | 24.2 |
| CPS | propylNH—N-methanamide | — | 25.2 | 10.2 |
| CPS | propylNH—N-methanamide | $Zn^{2+}$ | 29.9 | 11.0 |
| CPS | propyl-3N-(4,5-dihydroimidazole) | — | 9.3 | 3.1 |
| CPS | propyl-3N-(4,5-dihydroimidazole) | $Zn^{2+}$ | 9.8 | 3.0 |
| CPS | — | — | 58.2 | 22.4 |
| CPS | — | $Zn^{2+}$ | 48.9 | 18.2 |

TABLE 12

Performance of immobilised TbSADH-N-His on amino-functionalised controlled porous silica. Immobilised yield is based on the activity of supernatants after immobilization for the oxidation of 2-propanol and conversion is based on the activity of the immobilised catalyst for the reduction of phenoxy-2-propanone. The CPS used in Table 13 is CPS Q30.

| Core | Functionalisation | Metal | Immobilised yield [%] | Conversion [%] |
|---|---|---|---|---|
| CPS | bis-propyl-N,N'-bis-(2-hydroxyethyl) ethylenediamine | — | 37.7 | 19.7 |
| CPS | bis-propyl-N,N'-bis-(2-hydroxyethyl) ethylenediamine | $Zn^{2+}$ | 56.6 | 24.1 |
| CPS | co-polymer propyl + propylNH—N-aminoethyl | — | 44.6 | 27.5 |

TABLE 12-continued

Performance of immobilised TbSADH-N-His on amino-functionalised controlled porous silica. Immobilised yield is based on the activity of supernatants after immobilization for the oxidation of 2-propanol and conversion is based on the activity of the immobilised catalyst for the reduction of phenoxy-2-propanone. The CPS used in Table 13 is CPS Q30.

| Core | Functionalisation | Metal | Immobilised yield [%] | Conversion [%] |
|---|---|---|---|---|
| CPS | co-polymer propyl + propylNH—N-aminoethyl | $Zn^{2+}$ | 26.8 | 39.3 |
| CPS | propylNH—N-methanamide | — | 17.0 | 7.6 |
| CPS | propylNH—N-methanamide | $Zn^{2+}$ | 0.0 | 12.9 |
| CPS | propyl-3N-(4,5-dihydroimidazole) | — | 54.7 | 34.9 |
| CPS | propyl-3N-(4,5-dihydroimidazole) | $Zn^{2+}$ | 66.2 | 46.0 |
| CPS | — | — | 56.5 | 33.0 |
| CPS | — | $Zn^{2+}$ | 42.8 | 46.6 |

Example 4 Cross-Linking of Enzymes to the Amino-Functionalised CPS Supports

4.1 Cross-Linking of SucP2 Immobilised on Amino Functionalised Controlled Pore Silica

4.1.1 Immobilisation

A freeze-dried powder of SucP2 (760 mg) was rehydrated in 150 mM MOPS buffer, pH 7 (19 mL) to obtain a cell-free extract concentration of 40 mg/mL (freeze-dried powder/buffer solution). The prepared cell-free extract was resuspended on a tilt/roller mixer for 10 min (60 rpm, 21° C.) and then centrifuged for 10 min (8000 rpm, 21° C.). After centrifugation, the cell-free extract (1 mL) was transferred to 1.5 mL Eppendorf tubes containing 20 mg of support (CPS Q30 functionalised with propylamine and $Zn^{2+}$ deposition from a solution with final concentration 0.15 mM). Samples were incubated for 1 h (15 rpm, 21° C.) and after immobilisation the supernatants were removed. The immobilised supports were washed with 150 mM MOPS buffer, pH 7 (2×1 mL).

4.1.2 Cross-Linking Treatment

The cross-linking reagents used were glutaraldehyde (GA) and the bis-epoxides neopentylglycol diglycidyl ether (NPE), glycerol diglycidyl ether (GDE) and polyethylene glycol diglycidyl ether (PDE). Solutions of each cross-linking reagent 2% (v/v) and ethanol 20% (v/v) were prepared in 150 mM MOPS buffer, pH 7 and added (1 mL) to the immobilised catalyst. Control catalysts (non cross-linked) were prepared with the addition of 150 mM MOPS buffer, pH 7 (1 mL) to the immobilised SucP2. Both control and cross-linked catalyst were incubated overnight on a tube rotator (15 rpm, 2° C.). The buffer/cross-linking solution were removed and the catalyst was washed with 150 mM MOPS buffer, pH 7 (3×1 mL). Cross-linking treatment under different conditions was performed in duplicate.

4.1.3 Activity of Immobilised Catalyst in Aqueous Medium

The activity of the heterogenous catalysts after cross-linking (with and without leaching treatment) was determined by their ability to convert sucrose and glucose to kojibiose (Scheme 7). A reaction mixture (1 mL) containing 1 M sucrose and 1 M glucose in deionised water was added to the immobilised catalyst. The mixture was incubated (1200 rpm, 55° C.) and samples of the supernatant (10 μL) were taken after 1 h, 2 h, 3 h and 4 h to determine catalyst productivity. The sample was diluted in deionised water (190 μL) and 100 mM of glycerol (internal standard) in acetonitrile:deionised water (85:15) (200 μL) was added. The mixture was quenched by placing the Eppendorf tubes on ice (2 min) and then centrifuged 2 min (15 000 rpm, 21° C.) for debris separation. The supernatant was transferred to a plastic inlet vial and analysed by HPLC-CAD to determine the conversion of sucrose and glucose to kojibiose (Table 13).

Scheme 7.
Transglycosylation of sucrose (1M) and glucose (1M) catalysed by immobilised SucP2 to produce kojibiose.

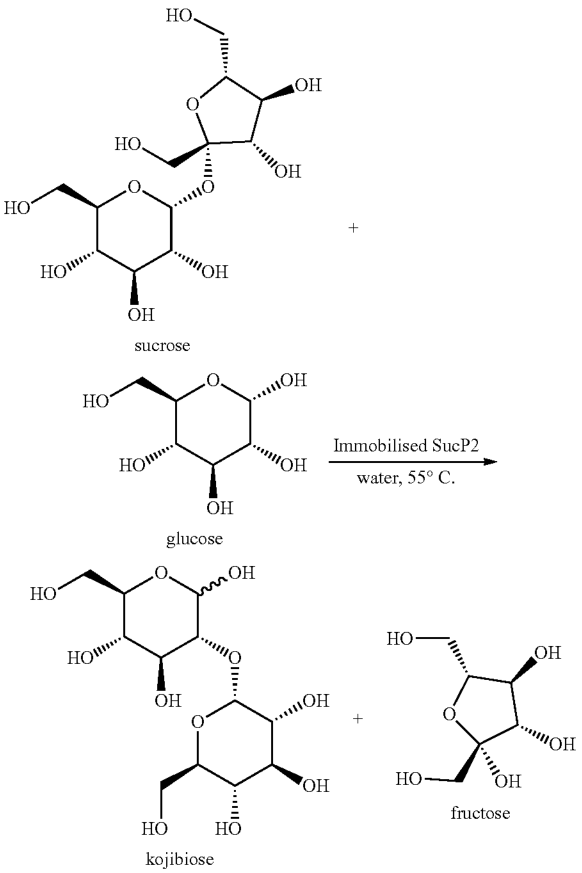

TABLE 13

Performance of immobilised SucP2 on propylamine-functionalised controlled porous silica (Q30) followed by cross-linking treatment. Productivity is based on the activity of the immobilised catalyst for the transglycosylation of sucrose and glucose to produce kojibiose as a function of time and amount of support. Productivity retention is based on the retention of productivity of the catalyst after cross-linking compared to the control catalyst without cross-linking.

| Cross-linking reagent | Productivity [$g_{kojibiose}$/h/$g_{support}$] | Productivity retention [%] |
|---|---|---|
| — (control) | 0.24 | — |
| GA | 0.04 | 17 |
| NPE | 0.22 | 92 |
| GDE | 0.24 | 100 |
| PDE | 0.24 | 100 |

4.2 Influence of pH on the Cross-Linking of Immobilised SucP2

4.2.1 Immobilisation

A freeze-dried powder of SucP2 (840 mg) was rehydrated in 150 mM MOPS buffer, pH 7 (10 mL) to obtain a cell-free extract concentration of 40 mg/mL (freeze-dried powder/buffer solution). The prepared cell-free extract was resuspended on a tilt/roller mixer for 10 min (60 rpm, 21° C.) and then centrifuged for 10 min (8000 rpm, 21° C.). After centrifugation, the cell-free extract (1 mL) was transferred to 1.5 mL Eppendorf tubes containing 20 mg of support (CPS Q30 functionalised with propylamine and $Zn^{2+}$ deposition from a solution with final concentration 0.15 mM). Samples were incubated for 1 h (15 rpm, 21° C.) and after immobilisation the supernatants were removed. The immobilised supports were washed with 150 mM MOPS buffer, pH 7 (2×1 mL).

4.2.2 Cross-Linking Treatment

The bis-epoxides used as cross-linking reagent were glycerol diglycidyl ether (GDE) and polyethylene glycol diglycidyl ether (PDE). Solutions of each bis-epoxide 2% (v/v) and ethanol 20% (v/v) were prepared in 150 mM MOPS buffer, pH 7 and pH 8, and 150 mM Tris/HCl buffer pH 9 and added (1 m) to the immobilised catalyst. Control catalysts (non cross-linked) were prepared with the addition of 150 mM MOPS buffer, pH 7 and pH 8, and 150 mM Tris/HCl buffer pH 9 (1 mL) to the immobilised SucP2. Both control and cross-linked catalyst were incubated overnight on a tube rotator (15 rpm, 25° C.). The buffer/cross-linking solution were removed and the catalyst was washed with 150 mM MOPS buffer, pH 7 (2×1 mL). Cross-linking treatment under different conditions was performed in duplicate.

4.2.3 Leaching Treatment

A leaching test was performed on the catalyst as a protocol to determine the efficiency of cross-linking. One sample from each different cross-linking condition (different cross-linking reagent and pH) was submitted to a leaching treatment whilst a sample from the same condition was kept separate and used as a control to enable the determination of the productivity of the immobilised catalyst with and without the leaching protocol. The leaching was performed with the addition of 0.5 M of sodium phosphate buffer, pH 7 (1 mL) to the immobilised catalyst and incubation on a tube rotator for 2 h (15 rpm, 21° C.). After the leaching protocol, the catalyst was washed with 150 mM MOPS buffer, pH 7 (2×1 mL). According to control studies, treatment of immobilised catalyst with 0.5 M of sodium phosphate is an effective method for leaching enzyme that have not been subject to cross-linking from the immobilised catalyst.

4.2.4 Activity of Immobilised Catalyst in Aqueous Medium

The activity of the heterogenous catalysts after cross-linking (with and without leaching treatment) was determined by their ability to convert sucrose and glucose to kojibiose (Scheme 9). A reaction mixture (1 mL) containing 1 M sucrose and 1 M glucose in deionised water was added to the immobilised catalyst. The mixture was incubated (1200 rpm, 55° C.) and samples of the supernatant (10 μL) were taken after 1 h, 2 h, 3 h and 4 h to determine catalyst productivity. The sample was diluted in deionised water (190 μL) and 100 mM of glycerol (internal standard) in acetonitrile:deionised water (85:15) (200 μL) was added. The mixture was quenched by placing the Eppendorf tubes on ice (2 min) and then centrifuged 2 min (15 000 rpm, 21° C.) for debris separation. The supernatant was transferred to a plastic inlet vial and analysed by HPLC-CAD to determine the conversion of sucrose and glucose to kojibiose (Table 14).

TABLE 14

Performance of immobilised SucP2 on propylamine-functionalised controlled porous silica (Q30) followed by cross-linking treatment at different pHs. Productivity is based on the activity of the immobilised catalyst for the transglycosylation of sucrose and glucose to produce kojibiose as a function of time and amount of support. Productivity retention is based on the retention of productivity of the catalyst after leaching treatment compared to the sample without leaching treatment.

| Cross-linking reagent | pH | Productivity [$g_{kojibiose}$/h/$g_{support}$] | Productivity retention [%] |
| --- | --- | --- | --- |
| — (control) | 7 | 0.28 | 17.6 |
| GDE | 7 | 0.35 | 48.7 |
| PDE | 7 | 0.39 | 25.6 |
| — (control) | 8 | 0.30 | 13.0 |
| GDE | 8 | 0.33 | 53.8 |
| PDE | 8 | 0.33 | 39.8 |
| — (control) | 9 | 0.25 | 11.0 |
| GDE | 9 | 0.36 | 63.9 |
| PDE | 9 | 0.33 | 25.1 |

4.3 Cross-Linking Treatment of Immobilised SucP2 with and without Amino-Functionalisation of CPS Support 4.3.1 Immobilisation A freeze-dried powder of SucP2 was rehydrated in 150 mM MOPS buffer, pH 7 (10 mL) to obtain a cell-free extract concentration of 120 mg/mL (freeze-dried powder/buffer solution). The prepared cell-free extract was resuspended on a tilt/roller mixer for 10 min (70 rpm, 21° C.) and then centrifuged for 10 min (8000 rpm, 21° C.). After centrifugation and separation of cell debris, the cell-free extract (1 mL) was added to 50 mg of support (CPS Q30 functionalised with propylamine and $Zn^{2+}$ deposition from a solution with final concentration 0.15 mM or non-functionalised CPS Q30 and $Zn^{2+}$ deposition from a solution with final concentration 0.15 mM). The enzyme was left for immobilisation on support for 1 h on a tilt/roller mixer (70 rpm, 21° C.) and after immobilisation the supernatants were removed. The immobilised support was washed with 150 mM MOPS buffer, pH 7 (2×1 mL) and used as wet catalyst for cross-linking.

4.3.2 Cross-Linking Treatment

The cross-linking linking solution was prepared with glycerol diglycidyl ether (GDE) 2% (v/v) and ethanol 20% (v/v) in 150 mM Tris/HCl buffer, pH 9. Cross-linking solution (1 mL) was added to the immobilised catalyst and incubated overnight on a tilt/roller mixer (70 rpm, 21° C.). The cross-linking solution was removed and the catalyst was washed with 150 mM MOPS buffer, pH 7 (2×1 mL).

4.3.3 Activity of Immobilised Catalyst in Aqueous Medium

The activity of the heterogenous catalysts (cross-linked or non cross-linked) was determined by their ability to convert sucrose and glucose to kojibiose (Scheme 9). A reaction mixture (1 mL) containing 1 M sucrose and 1 M glucose in deionised water was added to the immobilised catalyst. The mixture was incubated (1200 rpm, 55° C.) and aliquots of the reaction mixture (5 µL) were taken after 30 min, 50 min, 70 min and 90 min to determine catalyst productivity. The aliquot taken was diluted in deionised water (95 µL) containing 13.5 mM of ribose (internal standard) and then acetonitrile (200 µL) was added. The mixture was quenched by placing the Eppendorf tubes on ice (2 min) and then centrifuged 2 min (15 000 rpm, 21° C.) for solid separation. The supernatant was transferred to a plastic inlet vial and analysed by HPLC-CAD to determine the conversion of sucrose and glucose to kojibiose (Table 15).

TABLE 15

Performance of immobilised SucP2 either on propylamine-functionalised or non-functionalised controlled porous silica (Q30). Productivity is based on the activity of the immobilised catalyst for the transglycosylation of sucrose and glucose to produce kojibiose as a function of time and amount of support. Productivity retention is based on the retention of productivity of the catalyst after cross-linking treatment compared to the sample without cross-linking treatment.

| Support | Productivity [$g_{kojibiose}$/h/$g_{support}$] | Productivity retention [%] |
| --- | --- | --- |
| CPS non-functionalised | 0.6 | — |
| CPS non-functionalised, cross-linked | 0.1 | 23 |
| CPS-propylamine | 1.9 | — |
| CPS-propylamine, cross-linked | 1.5 | 79 |

4.4 Modification of CPS-Q30 Propylamine with Bis-Epoxide

Besides the stabilisation of the enzyme immobilised on CPS-Q30 through the cross-linking treatment with bis-epoxides, the modification of the amino-functionalised CPS with bis-epoxides prior to enzyme immobilisation was also demonstrated. The support modification with bis-epoxide was performed using glycerol diglycidyl ether (GDE). CPS-Q30 propylamine and $Zn^{2+}$ deposition from a solution with final concentration 0.15 mM (10 mg) in 2 mL Eppendorf tube was wetted with deionised water (1 mL) before the addition of bis-epoxide solution. GDE 15% (v/v) and ethanol 20% (v/v) in 150 mM Tris/HCl buffer, pH 9 (500 µL) was added to the support and incubated overnight (1200 rpm, 30° C.). The bis-epoxide solution was removed and the catalyst was washed with deionised water (2×1 mL), followed by wash with 25 mM sodium phosphate buffer, 150 mM NaCl, pH 8 (1×1 mL).

4.4.1 Immobilisation

A freeze-dried powder of glycosyl transferase was prepared in 25 mM sodium phosphate buffer, 150 mM NaCl, pH 8 to obtain a cell-free extract concentration of 14 mg/mL (freeze-dried powder/buffer solution). The prepared cell-free extract (1 mL) was transferred to 2 mL Eppendorf tubes containing 10 mg of support (CPS-Q30 propylamine and $Zn^{2+}$ deposition from a solution with final concentration 0.15 mM and CPS-Q30 propylamine and $Zn^{2+}$ deposition from a solution with final concentration 0.15 mM GDE-modified as previously described). Samples were incubated for 2 h on a tube rotator (20 rpm, 21° C.) and after immobilisation the supernatants were removed. The immobilised supports were washed with 50 mM MOPS buffer, pH 7.2 (3×1 mL).

4.4.2 Determination of Immobilisation Yield

An aliquot of initial enzyme solution or supernatant from immobilisations (250 µL) was mixed with a reaction mixture containing 0.67 M sucrose, 0.13 M hydroquinone, 0.013 M ascorbic acid in 50 mM MOPS buffer, pH 7.2 (750 µL) and incubated for 1 h (600 rpm, 30° C.). An aliquot of the mixture (25 µL) was diluted in deionised water (55 µL) and then acetonitrile (100 µL) was added. The formation of α-arbutin was measured by HPLC UV-Vis (Scheme 8). The immobilised yield was calculated by determining the percentage of enzymatic activity left in the supernatant after immobilisation compared to the enzymatic activity in the cell-free extract (Table 16).

4.4.3 Cross-Linking and Double Cross-Linking Treatment

Solutions of GDE 6% (v/v) and ethanol 20% (v/v) were prepared in 25 mM sodium phosphate buffer, pH 7 and added (1 mL) to the catalyst immobilised on both CPS-Q30 propylamine+$Zn^{2+}$ (cross-linking) and CPS-Q30 propylamine+$Zn^{2+}$ GDE-modified (double cross-linking). Control catalysts (non cross-linked) were prepared with the addition of 25 mM sodium phosphate buffer, pH 7 (1 mL) to the immobilised glycosyl transferase. Both control and cross-linked catalyst were incubated overnight on a tube rotator (15 rpm, 25° C.). The buffer/cross-linking solution were removed and the catalyst was washed with 50 mM MOPS buffer, pH 7.2 (3×1 mL). Cross-linking treatment under different conditions was performed in duplicate and one of the replicates, including non cross-linked catalyst, was submitted to a leaching treatment.

4.4.4 Leaching Treatment

One sample from each different condition (with and without cross-linking treatment on CPS CPS-Q30 propylamine+$Zn^{2+}$ or CPS-Q30 propylamine+$Zn^{2+}$ GDE-modified) was submitted to the leaching protocol whilst a sample from the same condition was kept separate and used as a control to enable the determination of the productivity of the immobilised catalyst with and without the leaching protocol. The leaching protocol was performed with the addition of 0.5 M of sodium phosphate buffer, pH 7 (1 mL) to the immobilised catalyst and incubation on a tube rotator for 2 h (20 rpm, 21° C.). After leaching, the supernatant was removed and kept for evaluation of leached enzyme from the catalyst. The leached support was washed with 50 mM MOPS buffer, pH 7.2 (3×1 mL).

4.4.5 Determination of Leached Protein

The supernatants from leaching solution were tested for protein leached from support using the bathocuproine disulfonate (BCS) assay method. Bovine serum albumin (BSA) protein standard and reagents for protein determination were purchased as a commercial kit from ThermoFisher. The BSA solutions for standard protein curve and samples from incubation with leaching solution were prepared following the instructions provided by the BCS kit. Protein concentration was measured by the absorbance ($A_{562}$) at 562 nm using a plate reader. The amount of leached protein expressed in mg/mL was extrapolated from the BSA calibration curve constructed by linear interpolation of the linear region of the $A_{562}$ vs $BSA_{[mg/ml]}$ plot (y=1.6285x+0.1335, $R^2$=99.8%).

4.4.6 Activity of Immobilised Catalyst

The activity of the heterogenous catalysts was determined by their ability to convert sucrose and hydroquinone to α-arbutin and fructose in the presence of ascorbic acid as an anti-oxidant (Scheme 8). A reaction mixture (1 mL) containing 0.5 M sucrose, 0.1 M hydroquinone, 0.01 M ascorbic acid in 50 mM MOPS pH 7.2 was added to the immobilised catalyst and the mixture was incubated for 1 h (1300 rpm, 30° C.). After stopping the mixing and allowing the catalyst to settle, an aliquot of the supernatant (25 μL) was diluted in deionised water (55 μL) and then acetonitrile (100 μL) was added. The mixture was transferred to a plastic inlet vial and analysed by HPLC UV-Vis to determine the conversion of sucrose and hydroquinone to α-arbutin.

Scheme 8.

Transglycosylation reaction catalysed by glycosyl transferase for the evaluation of both the immobilisation yield on the tested supports and the performance of the different resulting immobilised catalysts.

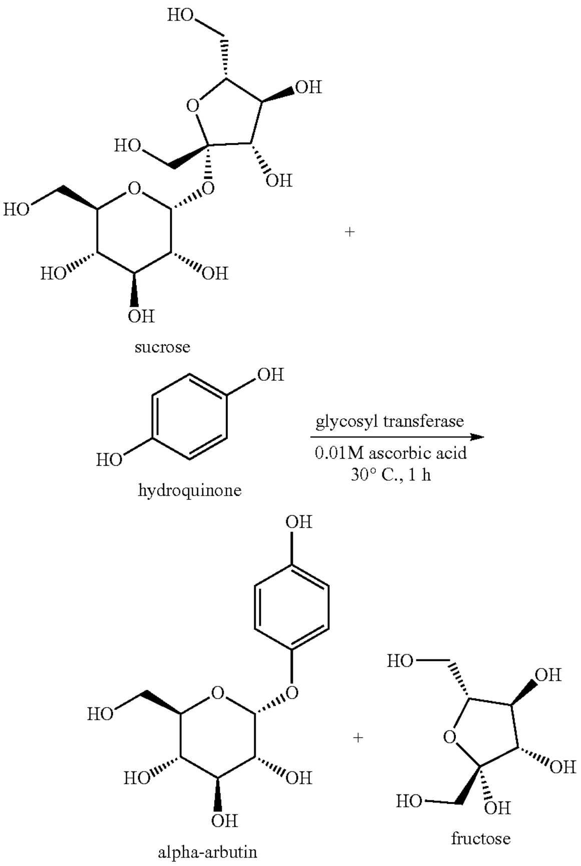

TABLE 16

Performance of immobilised glycosyl transferase on propylamine-functionalised controlled porous silica (Q30) (with and without bis-epoxide modification) followed by cross-linking treatment. Productivity is based on the activity of the immobilised catalyst to produce α-arbutin. Productivity retention is based on the relative productivity of the catalyst with treatments (support modification/x-linking) compared to the catalyst without any treatment (control).

| Support modification | Cross-linking treatment | Immobilised yield [%] | Leached protein [mg/ml] | Productivity [$g_{product}$/h/$g_{immob.CFE}$] | Relative Productivity [%] |
|---|---|---|---|---|---|
| GDE | none | 33 | — | 3.67 | 121% |
| (15 vol %) | | | 0.03 | 3.99 | 131% |
| | GDE | 33 | — | 3.19 | 105% |
| | (6 vol %) | | 0.00 | 2.86 | 94% |
| none | none | 42 | — | 3.05 | 100% (control) |
| | | | 0.50 | 1.23 | 40% |

TABLE 16-continued

Performance of immobilised glycosyl transferase on propylamine-functionalised controlled porous silica (Q30) (with and without bis-epoxide modification) followed by cross-linking treatment. Productivity is based on the activity of the immobilised catalyst to produce α-arbutin. Productivity retention is based on the relative productivity of the catalyst with treatments (support modification/x-linking) compared to the catalyst without any treatment (control).

| Support modification | Cross-linking treatment | Immobilised yield [%] | Leached protein [mg/ml] | Productivity [$g_{product}$/h/$g_{immob.CFE}$] | Relative Productivity [%] |
|---|---|---|---|---|---|
| | GDE | 42 | — | 3.61 | 119% |
| | (6 vol %) | | 0.05 | 3.43 | 113% |

Example 5 Catalyst Stability Under Continuous Flow Conditions 5.1 Stability of Ca/B Immobilised on Amino-Functionalised Controlled Pore Silica in Organic Solvent Under Continuous Flow 5.1.1 Immobilisation Cell-free extract containing CalB-N-His in 20 mM MOPS, pH 7.5 (2×40 mL) was clarified by centrifugation for 60 min (11000 rpm, 4° C.) followed by filtration using a 0.45 μm PVDF filter. The pH of the clarified cell-free extract was adjusted to 7.5 using 0.1 M NaOH. After preparation, cell-free extract (70 mL) was transferred 50 mL Falcon tube containing 700 mg of support (CPS-Q30 functionalised with propylamine and $Zn^{2+}$ deposition from a solution with final concentration 140 mM). Enzyme was left for immobilisation on support for 3 h on a tilt/roller mixer (70 rpm, 25° C.). The supernatant was removed and the immobilised support transferred to a glass filter and washed with 250 mM MOPS, pH 7.5 (3×20 mL). The catalyst was transferred to 15 mL Falcon tubes and dried under vacuum in a desiccator overnight.

5.1.2 Continuous Flow Run and Sample Analysis

The dried catalyst (300 mg) was packed into a Uniqsis column reactor (1 cm OD). The reaction mixture for the feed flow was prepared with 2 M (±)-1-phenylethanol, 1.2 M vinyl acetate and 1% (v/v) dodecane in MTBE (1 L). The packed reactor was assembled in a Uniqsis FlowSyn system. Reaction mixture was fed constantly to the reactor (0.61 mL/min, 30° C.) and samples were collected regularly. The samples from the outlet (10 μL) were diluted in EtOAc (990 μL) in a glass vial and analysed by GC-FID to determine the conversion of (±)-1-phenylethanol Results are illustrated in Table 17, which demonstrate stable operation for over 73 hours of continuous flow.

TABLE 17

Stability in flow of CalB immobilised in CPS-Q30 propylamine with 140 mM of $Zn^{2+}$. Conversion is based on the activity of the immobilised catalyst for the transesterification of (±)-1-phenylethanol with vinyl acetate.

| Time on stream [h] | Conversion [%] |
|---|---|
| 0 | — |
| 16.9 | 12.0 |
| 20.4 | 12.2 |
| 20.6 | 12.3 |
| 25.1 | 12.4 |
| 40.4 | 12.8 |
| 44.7 | 12.6 |
| 45.0 | 12.9 |
| 50 | 12.5 |
| 65.0 | 12.2 |
| 71.1 | 12.1 |

TABLE 17-continued

Stability in flow of CalB immobilised in CPS-Q30 propylamine with 140 mM of $Zn^{2+}$. Conversion is based on the activity of the immobilised catalyst for the transesterification of (±)-1-phenylethanol with vinyl acetate.

| Time on stream [h] | Conversion [%] |
|---|---|
| 71.2 | 12.3 |
| 73.4 | 12.1 |

5.2 Stability of SucP1 in Continuous Flow with and without Cross-Linking Treatment 5.2.1 Immobilisation Purified SucP1 was diluted in 50 mM MOPS buffer, pH 8 to obtain an enzyme solution concentration of 0.6 mg/mL (enzyme/buffer solution). The prepared enzyme solution (10 mL) was transferred to 15 mL Falcon tubes containing 300 mg of support (CPS-Q30 functionalised with propylamine and $Zn^{2+}$ deposition from a solution with final concentration 0.15 mM). Samples were left on tilt/roller mixer for 1 h (60 rpm, 21° C.) and after immobilisation the supernatants were removed. The immobilised supports were washed with 50 mM MOPS buffer, pH 8 (2×10 mL). The procedure was repeated twice and one of the immobilised catalysts was submitted to cross-linking treatment.

5.2.2 Cross-Linking Treatment

The cross-linking linking solution was prepared with neopentyl glycol diglycidyl ether (NPE) 2% (v/v) and ethanol 20% (v/v) in 50 mM MOPS buffer, pH 8. Cross-linking solution (30 mL) was added to the immobilised catalyst and incubated overnight on tilt/roller mixer (60 rpm, 21° C.). The solution was removed and the catalyst was washed with 50 mM MOPS buffer, pH 8 (2×10 mL).

5.2.3 Continuous Flow Run and Sample Analysis

The wet catalyst (300 mg) was packed into an Uniqsis column reactor (1 cm OD) straight after immobilization or cross-linking treatment. The reaction mixture for the feed flow was prepared with 2 M sucrose in 100 mM sodium phosphate buffer, pH 7.8 (1 L). Multiple batches of reaction mixture were prepared according to reactor feeding needs. The packed reactor was assembled in a Uniqsis FlowSyn system. Reaction mixture was fed constantly to the reactor (0.2 mL/min, 25° C.) and samples were collected regularly. The samples from the outlet (50 μL) were quenched with 1 M HCl (50 μL), diluted in deionised water (100 μL) and centrifuged 2 min (15 000 rpm, 21° C.) for debris separation. The supernatant was transferred to a plastic inlet vial and analysed by HPLC-RID to determine the conversion of phosphate to glucose 1-phosphate (G1P) (Scheme 9) (Table 18).

Scheme 9.
Sucrose (1M) conversion to G1P and fructose catalysed by immobilised SucP1.

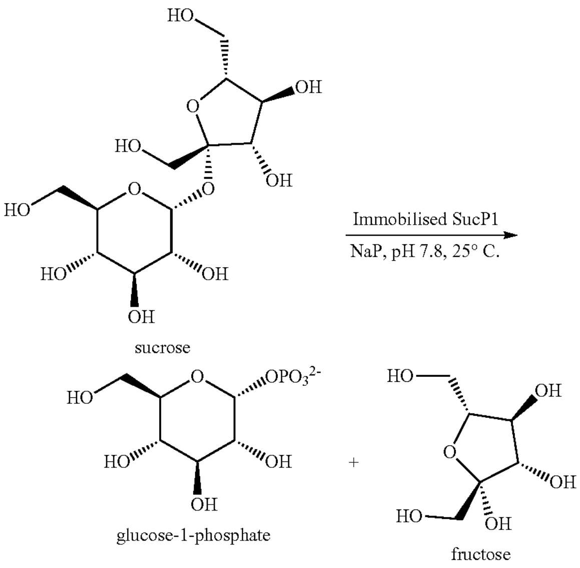

sucrose glucose-1-phosphate + fructose

TABLE 18

Comparison between the stability in flow of immobilised SucP1 with and without cross-linking treatment. Conversion is based on the activity of the immobilised catalyst for production of G1P on stream.

| Non cross-linked catalyst | | Cross-linked catalyst | |
|---|---|---|---|
| Time on stream [h] | Conversion [%] | Time on stream [h] | Conversion [%] |
| 2.0 | 3.5 | 2.5 | 41 |
| 17.3 | 2.4 | 19.3 | 33 |
| 24.0 | 1.7 | 28.0 | 34 |
| 26.0 | 2.1 | 52.3 | 36 |
| 91.5 | 1.3 | 115.6 | 34 |
| —* | — | 149.0 | 33 |
| — | — | 170.0 | 33 |
| — | — | 200.2 | 34 |

*For the non-cross-linked catalyst, after 91.5 hours the conversion diminished to levels below reliable detection limit of the HPLC method.

5.3 Stability of SucP2 in Continuous Flow with and without Cross-Linking Treatment 5.3.1 Preparation of Non Cross-Linked Catalyst and Continuous Flow Run 5.3.1.1 Immobilisation A freeze-dried powder of SucP2 was rehydrated in 150 mM MOPS buffer, pH 7 (50 mL) to obtain a cell-free extract concentration of 40 mg/mL (freeze-dried powder/buffer solution). The prepared cell-free extract was resuspended on a tilt/roller mixer for 10 min (70 rpm, 21° C.) and then centrifuged for 10 min (8000 rpm, 21° C.). After centrifugation and separation of cell debris, the cell-free extract was transferred 50 mL Falcon tube containing 3 g of support (CPS-Q30 functionalised with propylamine with 0.15 mM $Zn^{2+}$ deposition). Enzyme was left for immobilisation on support for 1 h on a tilt/roller mixer (70 rpm, 21° C.) and after immobilisation the supernatants were removed. The immobilised support was washed with 150 mM MOPS buffer, pH 7 (3×45 mL) and used as wet catalyst for flow run.

5.3.1.2 Continuous Flow Run and Sample Analysis

The wet catalyst (4.5 g) was packed into an Uniqsis column reactor (1 cm OD). The reaction mixture for the feed flow was prepared with 1 M sucrose, 1 M glucose in deionised water (1 L). Multiple batches of reaction mixture were prepared according to reactor feeding needs. The packed reactor was assembled in a Uniqsis FlowSyn system. Reaction mixture was fed initially (0.125 mL/min, 25° C.) until product could be detected from the reactor outlet. After that, the temperature was adjusted to 55° C. and flow was kept at 0.125 mL/min. Samples were collected regularly and productivity was calculated in kg of kojibiose/kg of support*hour. The samples from the outlet (5 µL) were diluted in deionised water (95 µL) and 100 mM of glycerol (internal standard) in acetonitrile:deionised water (85:15) (100 µL) was added. The mixture was quenched by placing the Eppendorf tubes on ice (2 min) and then centrifuged 2 min (15 000 rpm, 21° C.) for debris separation. The supernatant was transferred to a plastic inlet vial and analysed by HPLC-CAD to determine the conversion of sucrose and glucose to kojibiose (Table 19).

5.3.2 Preparation of Cross-Linked Catalyst and Continuous Flow Run 5.3.2.1 Immobilisation A freeze-dried powder of SucP2 was rehydrated in 150 mM MOPS buffer, pH 7 (2×50 mL) to obtain a cell-free extract concentration of 40 mg/mL (freeze-dried powder/buffer solution). The prepared cell-free extract was resuspended on a tilt/roller mixer for 10 min (70 rpm, 21° C.) and then centrifuged for 10 min (8000 rpm, 21° C.). After centrifugation and separation of cell debris, the two tubes containing cell-free extract were combined to a 100 mL Duran bottle containing 10.5 g of support (CPS functionalised with propylamine with 0.15 mM $Zn^{2+}$ deposition). Enzyme was left for immobilisation on support for 1 h on a tilt/roller mixer (70 rpm, 21° C.) and after immobilisation the supernatants were removed. The immobilised support was washed with 150 mM MOPS buffer, pH 7 (3×90 mL).

5.3.2.2 Cross-Linking Treatment

The cross-linking linking solution was prepared with glycerol diglycidyl ether (GDE) 2% (v/v) and ethanol 20% (v/v) in 150 mM Tris/HCl buffer, pH 9. Cross-linking solution (100 mL) was added to the immobilised catalyst and incubated overnight on a tilt/roller mixer (70 rpm, 21° C.). The solution was removed and the catalyst was washed with 150 mM MOPS buffer, pH 7 (1×90 mL) and with 150 mM MOPS buffer pH 7, 250 mM sucrose (1×90 mL). The catalyst was filtered under vacuum to remove the excess of buffer and then dried under vacuum in a desiccator overnight.

5.3.3 Continuous Flow Run and Sample Analysis

The dried catalyst (2.6 g) was packed into two Uniqsis column reactor (1 cm 00) connected in series. The reaction mixture for the feed flow was prepared with 1 M sucrose, 1 M glucose in deionised water (1 L). Multiple batches were prepared according to reactor feeding needs. The packed reactor was assembled in a Uniqsis FlowSyn system. Reaction mixture was fed initially (0.125 mL/min, 25° C.) until product could be detected from the reactor outlet. After that, the temperature was adjusted to 55° C. and flow was kept at 0.125 mL/min. Samples were collected regularly and productivity was calculated in kg of kojibiose/kg of support*hour. The samples from the outlet (5 µL) were diluted in deionised water (95 µL) and 100 mM of glycerol (internal standard) in acetonitrile:deionised water (85:15) (100 µL) was added. The mixture was quenched by placing the Eppendorf tubes on ice (2 min) and then centrifuged 2 min (15 000 rpm, 21° C.) for debris separation. The supernatant was transferred to a plastic inlet vial and analysed by HPLC-CAD to determine the conversion of sucrose and glucose to kojibiose (Table 19).

TABLE 19

Comparison between the stability in flow of immobilised SucP2 with and without cross-linking treatment. As the catalyst was packed as a wet formulation the productivity in flow is expressed by the production of kojibiose as a function of the amount of support per hour by immobilised SucP2 on stream [$kg_{kojibiose}/kg_{support}$*hour].

| Non cross-linked catalyst | | Cross-linked catalyst | |
|---|---|---|---|
| Time on stream [h] | [$kg_{kojibiose}/kg_{support}$*h] | Time on stream [h] | [$kg_{kojibiose}/kg_{support}$*h] |
| 2.1 | 0.41 | 2.2 | 0.57 |
| 16.4 | 0.37 | 14.3 | 0.54 |
| 25.7 | 0.36 | 24.7 | 0.50 |
| 45.8 | 0.34 | 47.2 | 0.48 |
| 57.9 | 0.34 | 58.8 | 0.45 |
| 70.0 | 0.31 | 72.0 | 0.46 |
| 80.1 | 0.31 | 83.1 | 0.45 |
| 90.2 | 0.31 | 91.2 | 0.45 |
| 98.7 | 0.30 | 99.6 | 0.44 |
| 105.5 | 0.30 | 107.3 | 0.43 |
| 114.3 | 0.29 | 114.9 | 0.42 |
| 123.6 | 0.27 | 123.8 | 0.43 |
| 137.3 | 0.27 | 139.7 | 0.42 |
| 146.3 | 0.26 | 146.5 | 0.40 |
| 154.0 | 0.25 | 155.4 | 0.42 |
| 163.7 | 0.25 | 163.3 | 0.41 |
| 177.1 | 0.24 | 170.4 | 0.40 |

5.4 Extended Continuous Flow Run with a Cross-Linked SucP2 Catalyst 5.4.1 Zn Deposition CPS Q30 functionalised with propylamine (5 g) was weighed into a 50 mL Falcon tube and deionised water (46.45 mL) was added. 36.7 mM of $ZnCl_2$ stock solution (1.05 mL) was added and the tube was left on a tilt/roller mixer for 1 h (70 rpm, 21° C.). The support was washed with deionised water (3×50 mL) and 150 mM MOPS buffer, pH 7 (1×50 mL). The support was used for immobilisation directly after $Zn^{2+}$ deposition procedure.

5.4.2 Immobilisation

A freeze-dried powder of SucP2 (6 g) was rehydrated in 150 mM MOPS buffer, pH 7 (50 mL) to obtain a cell-free extract concentration of 120 mg/mL (freeze-dried powder/buffer solution). The prepared cell-free extract was resuspended on a tilt/roller mixer for 10 min (70 rpm, 21° C.) and then centrifuged for 15 min (8000 rpm, 21° C.). After centrifugation and separation of cell debris, all the cell-free extract preparation was added to the 50 mL Falcon tube containing support with fresh $Zn^{2+}$ deposition. Enzyme was left for immobilisation on support for 90 min on a tube rotator (20 rpm, 21° C.) and after immobilisation the supernatants were removed. The immobilised support was washed with 150 mM MOPS buffer, pH 7 (2×50 mL).

5.4.3 Cross-Linking Treatment

The cross-linking linking solution was prepared with glycerol diglycidyl ether (GDE) 4% (v/v) and ethanol 20% (v/v) in 150 mM Tris/HCl buffer, pH 9. Cross-linking solution (100 mL) was added to the immobilised catalyst and incubated overnight on a tube rotator (20 rpm, 21° C.). The solution was removed and the catalyst was washed with 150 mM MOPS buffer, pH 7 (1×10 mL) and with 400 mM sucrose, 50 mg/mL maltodextrin in 150 mM MOPS buffer, pH 7 (1×90 mL). The catalyst was filtered under vacuum to remove the excess of buffer and then dried under vacuum in a desiccator for 6 h.

5.4.4 Continuous Flow Run and Sample Analysis

The dried catalyst (2 g) was packed into two Uniqsis column reactors (1 cm OD). The reaction mixture for the feed flow was prepared with 1 M sucrose, 1 M glucose in deionised water (1 L). Multiple batches were prepared according to reactor feeding needs. The packed reactor was assembled in a Uniqsis FlowSyn system. Reaction mixture was fed initially (0.25 mL/min, 45° C.) and then flow was decreased and kept at 0.1 mL/min. Samples were collected regularly and productivity calculated in kg of kojibiose/kg of support*hour. The samples from the outlet (5 μL) were diluted in deionised water containing 13.5 mM ribose (internal standard) (95 μL) and acetonitrile (100 μL) was added. The mixture was quenched by placing the Eppendorf tubes on ice (2 min) and then centrifuged 2 min (15 000 rpm, 21° C.) for debris separation. The supernatant was transferred to a plastic inlet vial and analysed by HPLC-CAD to determine the conversion of sucrose and glucose to kojibiose (Table 20).

TABLE 20

Time on stream of immobilised SucP2 with cross-linking treatment. Productivity is based on the production of kojibiose as a function of the amount of support per hour for the immobilised SucP2 catalyst.

| Time on stream [h] | Productivity [$kg_{kojibiose}/kg_{support}$/h] |
|---|---|
| 8.8 | 0.68 |
| 17.2 | 0.62 |
| 23.0 | 0.59 |
| 57.8 | 0.53 |
| 92.6 | 0.60 |
| 96.1 | 0.54 |
| 117.2 | 0.52 |
| 138.3 | 0.51 |
| 144.0 | 0.50 |
| 152.0 | 0.49 |
| 159.9 | 0.49 |
| 162.8 | 0.49 |
| 168.0 | 0.49 |
| 176.0 | 0.49 |
| 184.0 | 0.48 |
| 189.7 | 0.47 |
| 235.8 | 0.47 |
| 281.8 | 0.46 |
| 288.0 | 0.46 |
| 296.6 | 0.45 |
| 305.1 | 0.45 |
| 331.1 | 0.45 |
| 336.1 | 0.45 |
| 344.0 | 0.45 |
| 351.8 | 0.45 |
| 359.6 | 0.48 |
| 428.9 | 0.48 |
| 439.6 | 0.49 |
| 448.5 | 0.48 |
| 455.8 | 0.49 |
| 465.1 | 0.48 |
| 474.4 | 0.48 |
| 480.2 | 0.48 |
| 488.3 | 0.48 |
| 496.5 | 0.48 |
| 504.5 | 0.48 |
| 512.2 | 0.48 |
| 520.0 | 0.48 |

Example 6 Comparison of CPS Supports to Other Supports

Figure 2:
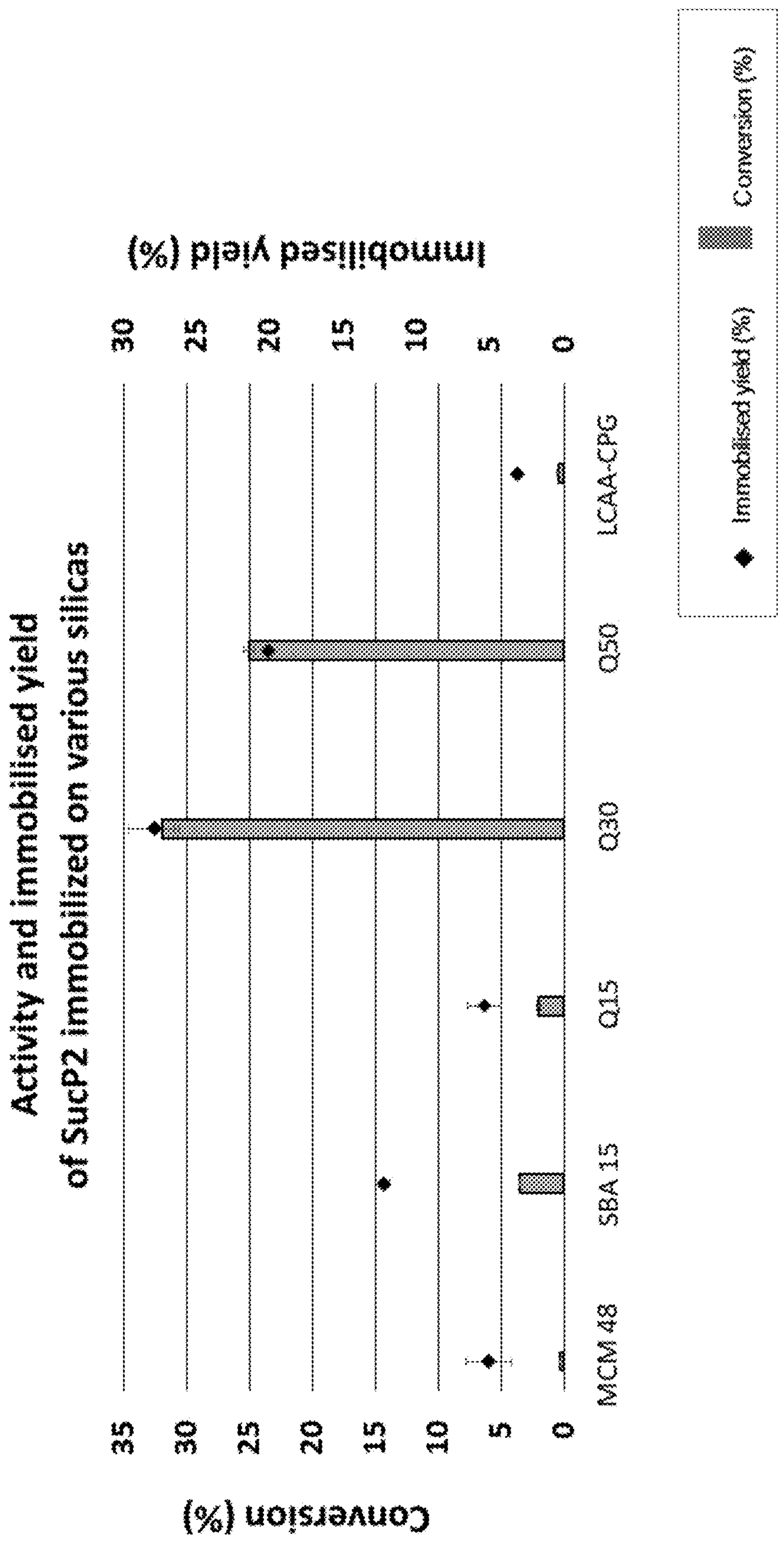
FIG. 2: Activity and immobilized yield of SucP2 immobilized on various types of carriers. It is noted that the Cariact Q15 having pore size below 20 nm performs poorly compared to Q30 and Q50. The support materials according to the invention perform much better than the prior art support materials LCAA-CPG, SBA15 and MCM48.

The reaction to convert sucrose and glucose to kojibiose illustrated in Scheme 7 was used to evaluate the activity of SucP2 enzyme immobilised on the controlled pore silica supports of the invention (Q30 and Q50, supplied by Fuji), in comparison with the activity of SucP2 enzyme immobilised on other commercially available porous silica supports and a controlled pore glass support. The following commercially available silica supports were used: 1) MCM-48 (supplied by Sigma Aldrich), a mesoporous silica with an ordered cage structure similar in nature to the mesoporous cellular foams (MCF) structures previously described in this disclosure, SBA-15 (supplied by Sigma Aldrich), a mesoporous silica containing ordered hexagonal pores, and Q15, a controlled pore silica containing pores with a diameter of 15 nm (supplied by Fuji, pore volume 1.00 ml/g, surface area 200 $m^2/g$). Additionally, an example of an aminofunctionalised-controlled pore glass material carrier (LCAA CPG ($Zn^{2+}$) was included in the comparative study. Each silica support was first treated with (3-aminopropyl) trimethoxysilane in the manner described in Section 1.2 to produce aminofunctionalised silica supports, and subsequently—further treated with $Zn^{2+}$ in the manner described in Section 1.5 to produce porous silicas functionalised with propylamine containing $Zn^{2+}$. Immobilisation of SucP2 onto the porous silicas and LCAA CPG ($Zn^{2+}$) was conducted in the manner described in Section 4.1.1, without cross-linking. Immobilisation yields were determined as described in Section 2.5.2 and the activity of the immobilised SucP2 catalysts was measured for the target reaction as described in Section 3.1.3. All experiments were conducted in duplicate. FIG. 2 illustrates the results of the comparative study and clearly demonstrates the superior performance of the controlled pore silicas of the invention.

Example 7 Cross-Linking of SucP2 Immobilised on Amino-Functionalised Controlled Pore Silica 7.1. Immobilisation A freeze-dried powder of SucP2 (500 mg) was rehydrated in 150 mM MOPS buffer, pH 7 (50 mL) to obtain a cell-free extract concentration of 10 mg/mL (freeze-dried powder/buffer solution). The prepared cell-free extract was resuspended on a tilt/roller mixer for 10 min (60 rpm, 21° C.) and then centrifuged for 10 min (8000 rpm, 21° C.). After centrifugation, the cell-free extract (1 mL) was transferred to 1.5 mL Eppendorf tubes containing 10 mg of support (CPS Q30 functionalised with propylamine, co-polymer propyl+propylNH—N-aminoethyl, propyl-3N-(4,5-dihydroimidazole), phenethyl-methyl-NH—N-aminoethyl and $Zn^{2+}$ deposition from a solution with final concentration 0.105 g/L). Samples were incubated for 2 h (20 rpm, 21° C.) and after immobilisation the supernatants were removed. The immobilised supports were washed with 150 mM MOPS buffer, pH 7 (2×1 mL).

7.2 Determination of Immobilisation Yield

An aliquot of initial enzyme solution or supernatant Irom immobilisations (100 μL) was mixed with a reaction mixture containing 1 M sucrose, 1 M glucose in deionised water (400 μL) and incubated for 2 h (600 rpm, 55° C.). An aliquot of the mixture ((10 μL) were taken and diluted in deionised water (190 l) and 100 mM of glycerol (internal standard) in acetonitrile:deionised water (85:15) (200 μL) was added. The mixture was quenched by placing the Eppendorf tubes on ice (2 min) and then centrifuged 2 min (15 000 rpm, 21° C.) for debris separation. The supernatant was transferred to a plastic inlet vial and analysed by HPLC-CAD to determine the conversion of sucrose and glucose to kojibiose. The immobilised yield was calculated by determining the percentage of enzymatic activity left in the supernatant after immobilisation compared to the enzymatic activity in the cell-free extract (21)

7.3 Cross-Linking Treatment

The cross-linking reagents used were glutaraldehyde (GA), dimethyl suberimidate (DMS), bis(sulfosuccinimidyl) suberate (BS3) and glycerol diglycidyl ether (GDE) (See Table 23). Solutions of each crosslinking reagent were prepared according to Table 21 in 150 mM MOPS buffer and 0.5 mL was subsequently added to the immobilised catalyst. Control catalysts (non cross-linked) were prepared with the addition of 150 mM MOPS buffer, pH 7 (0.5 mL) to the immobilised SucP2. Both control and cross-linked catalysts were incubated overnight on a tube rotator (20 rpm, 21° C.). The buffer/cross-linking solution was removed and the catalysts treated with DMS and B53 were washed once with 1 ml 20 mM TRIS, pH 7 before all before all catalysts were washed with 150 mM MOPS buffer, pH 7 (2×1 mL). Cross-linking treatment under different conditions was performed in duplicate.

TABLE 21

Solutions used for cross-linking treatment on immobilised SucP2

| Cross-linker reagent | Cross-linker amount [v/v %/wt/v %] | Co-solvent | pH buffer |
|---|---|---|---|
| GDE | 2 | Ethanol (20 v/v %) | 7 |
| DMS | 2 | — | 8 |
| BS3 | 0.5 | — | 7 |
| GA | 1.9 | — | 7 |

7.4 Leaching Treatment

A leaching test was performed on the catalyst as a protocol to determine the efficiency of cross-linking. One sample from each different cross-linking condition (different cross-linking reagent) was submitted to a leaching treatment whilst a sample from the same condition was kept separate and used as a control to enable the determination of the productivity of the immobilised catalyst with and without the leaching protocol. The leaching was performed with the addition of 0.5 M of sodium phosphate buffer, pH 7 (1 mL) to the immobilised catalyst and incubation on a tube rotator for 2 h (20 rpm, 21° C.). After the leaching protocol, the catalyst was washed with 150 mM MOPS buffer, pH 7 (2×1 mL). According to control studies, treatment of immobilised catalyst with 0.5 M of sodium phosphate is an effective method for leaching enzyme that have not been subject to cross-linking from the immobilised catalyst.

7.5 Activity of Immobilised Catalyst in Aqueous Medium

The activity of the heterogenous catalysts after cross-linking (with and without leaching treatment) was determined by their ability to convert sucrose and glucose to kojibiose (Scheme 7). A reaction mixture (1 mL) containing 1 M sucrose and 1 M glucose in deionised water was added to the immobilised catalyst. The mixture was incubated (1200 rpm, 55° C.) and samples of the supernatant (10 μL) were taken after 3 h to determine catalyst productivity. The sample was diluted in deionised water (190 μL) and 100 mM of glycerol (internal standard) in acetonitrile:deionised water (85:15) (200 μL) was added. The mixture was quenched by placing the Eppendorf tubes on ice (2 min) and then centrifuged 2 min (15 000 rpm, 21° C.) for debris separation. The supernatant was transferred to a plastic inlet vial and analysed by HPLC-CAD to determine the conversion of sucrose and glucose to kojibiose (Table 22).

Scheme 10.
Transglycosylation of sucrose (1M) and glucose (1M) catalysed by immobilised SucP2 to produce kojibiose.

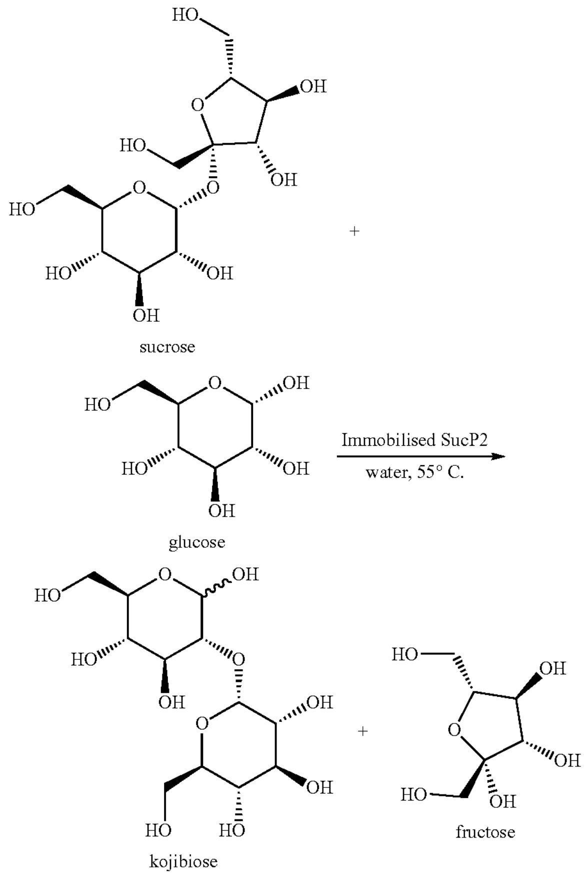

sucrose + glucose → kojibiose + fructose

TABLE 22

Performance of immobilised SucP2 on propylamine, co-polymer propyl + propylNH—N-aminoethyl, propyl-3N-(4,5-dihydroimidazole), phenethyl-methyl-NH—N-aminoethyl-functionalised controlled porous silica (Q30), followed by cross-linking treatment with and without GDE, DMS, BS3, GA and with and without being subjected to the leaching protocol. Productivity is based on the activity of the immobilised catalyst for the transglycosylation of sucrose and glucose to produce kojibiose as a function of time and amount of support.

| Q30 CPS functionalised with: | Cross-linking reagent | Leaching Protocol | Immobilisation yield [%] | Productivity [$g_{kojibiose}$/($g_{support}$)*hr] |
|---|---|---|---|---|
| propylamine | None | No | 33 | 2.2 |
| propylamine | None | Yes | 33 | 0.6 |
| propylamine | GDE | No | 33 | 1.8 |
| propylamine | GDE | Yes | 33 | 1.7 |
| propylamine | DMS | No | 33 | 2.0 |
| propylamine | DMS | Yes | 33 | 2.1 |
| propylamine | BS3 | No | 33 | 2.7 |
| propylamine | BS3 | Yes | 33 | 3.1 |
| propylamine | GA | No | 33 | 0.3 |
| propylamine | GA | Yes | 33 | 0.3 |
| co-polymer propyl + propylNH—N-aminoethyl | None | No | 8 | 0.4 |
| co-polymer propyl + propylNH—N-aminoethyl | None | Yes | 8 | 0.3 |

TABLE 22-continued

Performance of immobilised SucP2 on propylamine, co-polymer propyl + propylNH—N-aminoethyl, propyl-3N-(4,5-dihydroimidazole), phenethyl-methyl-NH—N-aminoethyl-functionalised controlled porous silica (Q30), followed by cross-linking treatment with and without GDE, DMS, BS3, GA and with and without being subjected to the leaching protocol. Productivity is based on the activity of the immobilised catalyst for the transglycosylation of sucrose and glucose to produce kojibiose as a function of time and amount of support.

| Q30 CPS functionalised with: | Cross-linking reagent | Leaching Protocol | Immobilisation yield [%] | Productivity [$g_{kojibiose}$/($g_{support}$)*hr] |
|---|---|---|---|---|
| co-polymer propyl + propylNH—N-aminoethyl | GDE | No | 8 | 0.5 |
| co-polymer propyl + propylNH—N-aminoethyl | GDE | Yes | 8 | 0.5 |
| co-polymer propyl + propylNH—N-aminoethyl | DMS | No | 8 | 0.5 |
| co-polymer propyl + propylNH—N-aminoethyl | DMS | Yes | 8 | 0.4 |
| co-polymer propyl + propylNH—N-aminoethyl | BS3 | No | 8 | 0.4 |
| co-polymer propyl + propylNH—N-aminoethyl | BS3 | Yes | 8 | 0.6 |
| co-polymer propyl + propylNH—N-aminoethyl | GA | No | 8 | 0.1 |
| co-polymer propyl + propylNH—N-aminoethyl | GA | Yes | 8 | 0.1 |
| propyl-3N-(4,5-dihydroimidazole) | None | No | 24 | 1.0 |
| propyl-3N-(4,5-dihydroimidazole) | None | Yes | 24 | 0.2 |
| propyl-3N-(4,5-dihydroimidazole) | GDE | No | 24 | 1.0 |
| propyl-3N-(4,5-dihydroimidazole) | GDE | Yes | 24 | 0.8 |
| propyl-3N-(4,5-dihydroimidazole) | DMS | No | 24 | 0.9 |
| propyl-3N-(4,5-dihydroimidazole) | DMS | Yes | 24 | 1.1 |
| propyl-3N-(4,5-dihydroimidazole) | BS3 | No | 24 | 1.4 |
| propyl-3N-(4,5-dihydroimidazole) | BS3 | Yes | 24 | 1.4 |
| propyl-3N-(4,5-dihydroimidazole) | GA | No | 24 | 0.2 |
| propyl-3N-(4,5-dihydroimidazole) | GA | Yes | 24 | 0.1 |
| phenethyl-methyl-NH—N-aminoethyl | None | No | 20 | 0.8 |
| phenethyl-methyl-NH—N-aminoethyl | None | Yes | 20 | 0.3 |
| phenethyl-methyl-NH—N-aminoethyl | GDE | No | 20 | 0.6 |
| phenethyl-methyl-NH—N-aminoethyl | GDE | Yes | 20 | 0.6 |
| phenethyl-methyl-NH—N-aminoethyl | DMS | No | 20 | 0.8 |
| phenethyl-methyl-NH—N-aminoethyl | DMS | Yes | 20 | 0.7 |
| phenethyl-methyl-NH—N-aminoethyl | BS3 | No | 20 | 0.7 |
| phenethyl-methyl-NH—N-aminoethyl | BS3 | Yes | 20 | 0.9 |
| phenethyl-methyl-NH—N-aminoethyl | GA | No | 20 | 0.1 |
| phenethyl-methyl-NH—N-aminoethyl | GA | Yes | 20 | 0.1 |

TABLE 23

| Cross-linking reagents and possible covalent bond types formed from the cross-linking step | | | |
|---|---|---|---|
| Name | Cas number | Chemical structure | Covalent bond type |
| glycerol diglycidyl ether (GDE) | 27043-36-3 | 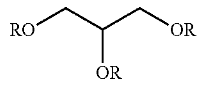 R = (1:2) H or 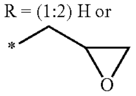 | amine, ester, ether, thiol |
| bis (sulfosuccinimidyl)-suberate (BS3) | 82436-77-9 | 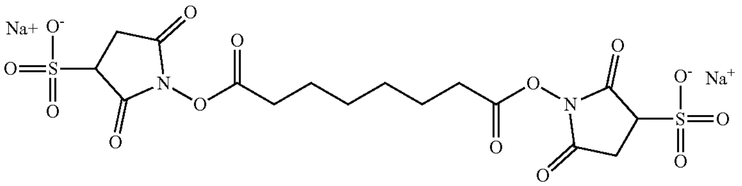 [SMILES: O=C(CCCCCCC(=O)ON1C(=O)CC(S(=O)(=O)[O-])C1=O)ON1C(=O)CC(S(=O)(=O)[O-])C1=O ; [Na+] ; [Na+]] | amide, thioester |
| dimethyl suberimidate (DMS) | 29878-26-0 | 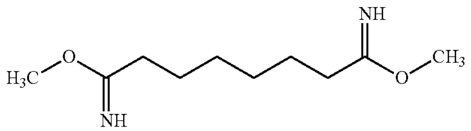 | Imidoamide, imidothioamide |

Example 8 Screening of Controlled Pore Silica with 2 Coatings

8.1. Synthesis of Controlled Pore Silica with 2 Different Silane Coatings

Syntheses of controlled pore silica support Cariact Q30 or Ecovyst E30 with 2 different coatings were carried out as previously described (examples section 1.2). The total volume of silane in the reaction mixture was fixed at 13% (15 mL silane:100 mL toluene). The panel of the silanes used for coating the silica supports with 2 coatings and the silane ratios are described in Table 24.

TABLE 24

| Silane 1 | Silane 2 | Ratio | CAS number |
|---|---|---|---|
| Triethoxy(octyl)silane | N-(6-aminohexyl)aminopropyltrimethoxysilane | 1:4 | 2943-75-1 SIA0594.0 |
| (aminoethylaminomethyl) phenethyltrimethoxysilane | 3-aminopropyl-trimethoxysilane | 1:1 | SIA0588.0 13822-56-5 |
| Triethoxy(propyl)silane | 3-aminopropyl-trimethoxysilane | 1:4 | SIP6918.0 13822-56-5 |
| Triethoxy(propyl)silane | N-(2-aminoethyl)-3-aminopropyltrimethoxysilane | 1:1 | SIA0591.3 |

8.2 Metal Deposition and Immobilisation

For the metal deposition step for the immobilisation of CalB-N-His, a metal stock solution of 0.93 mM was added to the support (see Table 2). For SucP2 and transaminase reactions, a zinc stock solution of 0.77 mM was added to each support well. Immobilisations of CalB-N-His, TbSADH, SucP2 (section 4.1.1) were carried out as described in the previous sections, without cross-linking (Results are presented in Tables 10-13).

8.3 Immobilisation of Amyloglucosidase on Controlled Pore Silica Containing 2 Coatings Prior to immobilisation, supports were pretreated (1 h, 20 rpm, 25° C.) with 200 mM NaP pH 6 (1 mL/10 mg support) to pH stabilise the material. Buffer was removed and the material was washed with deionized water (2×1 mL, 5 min, 20 rpm, 25° C.). An enzyme solution containing 16.7% enzyme was prepared by diluting the commercially available enzyme stock (supplied by Novozymes) with deionized water. 1 mL of the prepared enzyme solution was added to each support (10 mg) and incubated for 17 h (20 rpm, 25° C.). Supernatants were saved for immobilised yield analysis and the immobilised catalysts were washed with deionized water (2×1 mL, 20 rpm, 5 min, 25° C.).

8.4 Determination of Immobilised Yield

Maltose solution (985 μL, 250 mM) was added to Eppendorfs containing either the supernatants from the immobilisation reactions (15 μL) or the stock enzyme solution (15 μL). These mixtures were incubated for 30 min (1000 rpm, 30° C.). The reaction was then thermally quenched at 95° C. for 5 min. The samples were then diluted 8×(75 μL reaction+225 μL 40 mM ribose+300 μL ACN) and analysed by HPLC. Immobilised yield was determined from the conversion of maltose to glucose.

8.5 Activity of the Immobilised Catalyst in Aqueous Medium

Maltose solution (1 mL, 250 mM) was added each Eppendorf containing the washed immobilised catalysts. The mixtures were then incubated for 30 min (30° C., 1200 rpm). The reaction was then thermally quenched at 95° C. for 5 min. The samples were then diluted 8×(75 μL reaction+225 μL 40 mM ribose+300 μL ACN) and analysed by HPLC.

Scheme 10
Hydrolysis of maltose (250 mM) catalysed by immobilised amyloglucosidase.

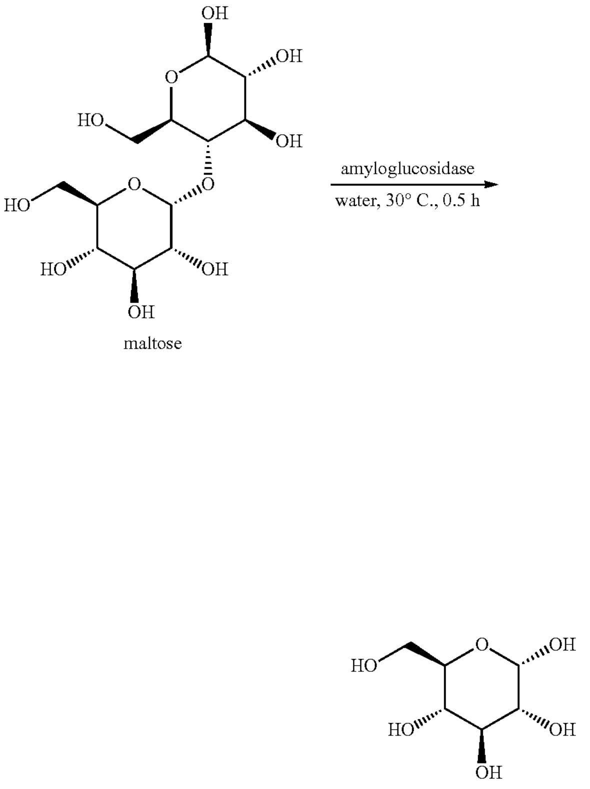

maltose glucose 8.6 Immobilisation of Transaminase (ATA) on Controlled Pore Silica Containing 2 Coatings A freeze-dried powder of amine transaminase TA633 (EC 2.6.1.62 supplied by Prozomix) (200 mg) was rehydrated in 20 mM NaP, pH 8 containing 0.3 mM pyridoxal 5'-phosphate to obtain a cell-free extract (CFE) containing 20 mg/mL (freeze-dried powder/total volume solution). The cell-free extract (500 μL) was transferred to Eppendorfs containing 10 mg of the controlled pore silicas containing 2 coatings that had been freshly deposited with zinc (1000 ppm) and incubated for 2 h (20 rpm, 25° C.). The supernatant was subsequently removed, and the immobilised catalysts were washed with 20 mM NaP buffer, pH 8 (2×1 mL) and used directly after removal of remaining buffer from the Eppendorfs.

8.7 Determination of Immobilised Yield

The cell-free extract and supernatant from the immobilisations (250 μL) were added to 250 μL of reaction mixture (20 mM NaP pH 8, 10% DMSO (5% final concentration), 100 mM phenoxy-2-propanone (50 mM final concentration), and 500 mM isopropylamine (250 mM final concentration) and incubated for 2 h (600 rpm, 35° C.). After 2 h, 5 M NaOH (150 μL) and EtOAc (500 μL) were added and incubated for an additional 5 min at room temperature (20 rpm), followed by 5 min of phase separation on the bench. Organic phase (200 μL) was then transferred to a new Eppendorf containing sodium sulfate. 40 μL of the extracted reaction were then transferred to a new Eppendorf containing acetic acid anhydride (130 μL). 1-methylimidazole (40 μL) was then added and the mixture was incubated for 30 min at room temperature. Deionized water (230 μL) was added and mixed, followed by the addition of EtOAc containing 40 mM dodecane (460 μL). This mixture was incubated for 5 min (25° C., 1200 rpm). Following phase separation (5 min), 200 μL of the organic phase was transferred to a plate containing sodium sulfate. The extracted sample was then analysed by gas chromatography. The immobilised yield was calculated based on the remaining enzymatic activity following immobilisation compared to that of the cell-free extract. All measurements were performed in duplicate and presented as an average of the individual samples.

8.8 Activity of the Immobilised Catalyst in Aqueous Medium

The activity of the immobilised catalysts was determined by their ability to convert phenoxy-2-propanone to the corresponding amine (Scheme 11). Reaction mixture (20 mM NaP pH 8, DMSO (5% v/v), phenoxy-2-propanone (50 mM), isopropylamine (250 mM)) was prepared and added (1 mL) to the immobilised and washed catalysts (10 mg). The reaction was incubated overnight (25° C., 1200 rpm). Following, 500 μL of supernatant was transferred to a new Eppendorf and 5M NaOH (150 μL) and EtOAc (500 μL) was added and incubated for 5 min (25° C., 1200 rpm). 40 μL of organic phase was then transferred to a new Eppendorf containing acetic anhydride (130 μL) and 1-methylimidazole (40 μL). The mixture was incubated for 30 min at room temperature. Deionized water (230 μL) was added and mixed, followed by the addition of EtOAc containing 40 mM dodecane (460 μL). This mixture was incubated for 5 min (25° C., 1200 rpm). Following phase separation (5 min), 200 IL of the organic phase was transferred to a plate containing sodium sulfate. The extracted sample was then analysed by gas chromatography. All measurements were performed in duplicate and presented as an average of the individual samples.

Scheme 11
Transamination between 1-phenoxypropan-2-one (50 mM) and isopropylamine (250 mM) catalysed by immobilised ATA.

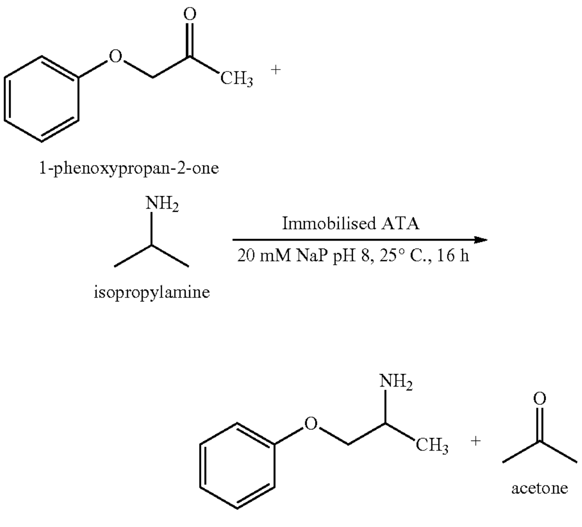

1-phenoxypropan-2-one isopropylamine 1-phenoxypropan-2-amine acetone

TABLE 25

| Amyloglucosidase activity on CPS containing 2 coatings | | | | |
|---|---|---|---|---|
| CPS | Silane 1 | Silane 2 | Immobilised yield [%] | Conversion [%] |
| Q30 | Triethoxy(octyl)silane | N-(6-aminohexyl) aminpropyltrimethoxysilane | 17.7 | 84.8 |
| Q30 | (aminoethylaminomethyl) phenethyltrimethoxysilane | 3-aminopropyl-trimethoxysilane | 23.7 | 83.7 |
| Q30 | Triethoxy(propyl)silane | 3-aminopropyl-trimethoxysilane | 27.7 | 86.6 |
| Q30 | Triethoxy(propyl)silane | N-(2-aminoethyl)-3-aminopropyltrimethoxysilane | 26.2 | 56.4 |
| Q30 | 3-aminopropyl-trimethoxysilane | none | 17.0 | 65.2 |

TABLE 26

| SucP2 activity on CPS containing 2 coatings | | | | |
|---|---|---|---|---|
| CPS | Silane 1 | Silane 2 | Immobilised yield [%] | Conversion [%] |
| Q30 | Triethoxy(octyl)silane | N-(6-aminohexyl) aminpropyltrimethoxysilane | 16.9 | 2.3 |
| Q30 | (aminoethylaminomethyl) phenethyltrimethoxysilane | 3-aminopropyl-trimethoxysilane | 23.0 | 8.0 |
| Q30 | Triethoxy(propyl)silane | 3-aminopropyl-trimethoxysilane | 25.0 | 9.0 |
| Q30 | Triethoxy(propyl)silane | N-(2-aminoethyl)-3-aminopropyltrimethoxysilane | 16.4 | 1.4 |
| Q30 | 3-aminopropyl-trimethoxysilane | none | 32.1 | 14.8 |
| E30 | 3-aminopropyl-trimethoxysilane | none | 23.9 | 7.4 |

TABLE 27

| CalB activity on CPS containing 2 coatings | | | | |
|---|---|---|---|---|
| CPS | Silane 1 | Silane 2 | Immobilised yield [%] | Conversion [%] |
| Q30 | Triethoxy(octyl)silane | N-(6-aminohexyl) aminpropyltrimethoxysilane | 16.8 | 4.9 |
| Q30 | (aminoethylaminomethyl) phenethyltrimethoxysilane | 3-aminopropyl-trimethoxysilane | 20.3 | 5.1 |
| Q30 | Triethoxy(propyl)silane | 3-aminopropyl-trimethoxysilane | 7.0 | 4.0 |
| Q30 | Triethoxy(propyl)silane | N-(2-aminoethyl)-3-aminopropyltrimethoxysilane | 39.3 | 8.1 |
| Q30 | 3-aminopropyl-trimethoxysilane | none | 19.4 | 6.5 |
| E30 | 3-aminopropyl-trimethoxysilane | none | 26.8 | 8.4 |

TABLE 28

| TbSADH activity on CPS containing 2 coatings | | | | |
|---|---|---|---|---|
| CPS | Silane 1 | Silane 2 | Immobilised yield [%] | Conversion [%] |
| Q30 | Triethoxy(octyl)silane | N-(6-aminohexyl) aminpropyltrimethoxysilane | ** | 17.5 |
| Q30 | (aminoethylaminomethyl) phenethyltrimethoxysilane | 3-aminopropyl-trimethoxysilane | ** | 29.4 |

TABLE 28-continued

| TbSADH activity on CPS containing 2 coatings | | | | |
|---|---|---|---|---|
| CPS | Silane 1 | Silane 2 | Immobilised yield [%] | Conversion [%] |
| Q30 | Triethoxy(propyl)silane | 3-aminopropyl-trimethoxysilane | 15.2 | 45.3 |
| Q30 | Triethoxy(propyl)silane | N-(2-aminoethyl)-3-aminopropyltrimethoxysilane | 14.8 | 44.3 |
| Q30 | 3-aminopropyl-trimethoxysilane | none | 42.4 | 61.0 |
| E30 | 3-aminopropyl-trimethoxysilane | none | 40.5 | 58.1 |

** Signal interference prevented measurement

TABLE 29

| ATA activity on CPS containing 2 coatings | | | | |
|---|---|---|---|---|
| CPS | Silane 1 | Silane 2 | Immobilised yield [%] | Conversion [%] |
| Q30 | Triethoxy(octyl)silane | N-(6-aminohexyl) aminpropyltrimethoxysilane | 24.4 | 0.0 |
| Q30 | (aminoethylaminomethyl) phenethyltrimethoxysilane | 3-aminopropyl-trimethoxysilane | 23.3 | 5.5 |
| Q30 | Triethoxy(propyl)silane | 3-aminopropyl-trimethoxysilane | 30.5 | 5.9 |
| Q30 | Triethoxy(propyl)silane | N-(2-aminoethyl)-3-aminopropyltrimethoxysilane | 63.3 | 6.4 |
| Q30 | 3-aminopropyl-trimethoxysilane | none | 53.2 | 13.2 |
| E30 | 3-aminopropyl-trimethoxysilane | none | 44.1 | 5.6 |

Example 9 Formulation of Heterogeneous Biocatalysts Using Controlled Pore Silicas with Larger Particle Sizes 9.1 Isolation of Controlled Pore Silicas with Particle Size Range 280-500 μm Isolating CPS Q30 particles of 280-500 μm was achieved by sieving 75-500 μm CPS Q30 (200 g supplied by Fuji) through a 280 μm mesh filter using a Haver EML 200 Premium sieve instrument. After several cycles (amplitude 2, 1 min), the isolated material (>280 μm) was removed and saved for further use.

9.2 Synthesis of Amino-Functionalised Controlled Pore Silica with 2 Particle Size Ranges (1: 280-500 μm, and 2: 1.18-2.36 mm)

Synthesis of amino-functionalised CPS particles with diameters from 280-500 μm, and 1.18-2.36 mm were produced according to the previously described protocol (Section 1.2). 9.3 Immobilisation of SucP2 on amino-functionalised 280-500 μm, and 1.18-2.36 mm CPS Q30 particles A freeze-dried powder of SucP2 (500 mg) was rehydrated in 150 mM MOPS buffer, pH 7 (50 mL) to obtain a cell-free extract concentration of 10 mg/mL (freeze-dried powder/buffer solution). The prepared cell-free extract was resuspended on a tilt/roller mixer for 10 min (60 rpm, 21° C.) and then centrifuged for 10 min (8000 rpm, 21° C.). After centrifugation, the cell-free extract (1 mL) was transferred to 1.5 mL Eppendorf tubes containing 10 mg of support (CPS Q30 functionalised with propylamine. The propylamine functionialised Q30 was subjected to a $Zn^{2+}$ deposition from a solution with final concentration 0.105 g/L). Samples were incubated for 2 h (20 rpm, 21° C.) and after immobilisation the supernatants were removed. The immobilised supports were washed with 150 mM MOPS buffer, pH 7 (2×1 ml).

9.4 Determination of Immobilisation Yield

An aliquot of initial enzyme solution or supernatant from immobilisations (100 μL) was mixed with a reaction mixture containing 1 M sucrose, 1 M glucose in deionised water (400 μL) and incubated for 1 h (600 rpm, 50° C.). The reaction was then thermally quenched at 95° C. for 5 min. 50 μL of sample was then added to 450 μl of 30 mM ribose (internal standard) followed by 500 μL ACN. The samples were then analysed by HPLC to determine the conversion of sucrose and glucose to kojibiose. The immobilised yield was calculated by determining the percentage of enzymatic activity left in the supernatant after immobilisation compared to the enzymatic activity in the cell-free extract.

9.5 Cross-Linking Treatment

A cross-linking solution of glycerol diglycidyl ether (GDE) was prepared in a mixture of ethanol and 150 mM Tris, pH 9 (4% GDE, 20% EtOH). The cross-linking solution was then added to the immobilised catalysts (1 mL/100 mg sample) and incubated for 24 h (20 rpm, 25° C.). The cross-linked catalysts were then washed with 150 mM Tris, pH 9 (2×1 mL, 1 min, 20 rpm, 25° C.). Samples were all performed in duplicate.

9.6 Leaching Treatment

A leaching test was performed on the catalyst as a protocol to determine the efficiency of cross-linking. Samples were subjected to a leaching treatment whilst a sample from the same condition was kept separate and used as a control to enable the determination of the productivity of the immobilised catalyst with and without the leaching protocol. The leaching was performed with the addition of 0.5 M of sodium phosphate buffer, pH 7 (1 mL) to the immobilised catalyst and incubation on a tube rotator for 2 h (800 rpm, 50° C.). After the leaching protocol, the catalyst was washed with deionized water (3×1 mL). According to control studies, treatment of immobilised catalyst with 0.5 M of sodium phosphate is an effective method for leaching enzyme that have not been subject to cross-linking from the immobilised catalyst.

9.7 Activity of Immobilised Catalyst in Aqueous Medium

The activity of the heterogenous catalysts after cross-linking (with and without leaching treatment) was determined by their ability to convert sucrose and glucose to kojibiose (Scheme 7). A reaction mixture (1 mL) containing 1 M sucrose and 1 M glucose in deionised water was added to the immobilised catalyst. The mixture was incubated for 0.5 h (1200 rpm, 55° C.). The reaction was then thermally quenched at 95° C. for 5 min. 50 μL of sample was then added to 450 μl of 30 mM ribose (internal standard) followed by 500 μL ACN. The samples were then analysed by HPLC to determine the conversion of sucrose and glucose to kojibiose.

TABLE 30

Summary of immobilisation yield and productivity of propylamine-functionalised controlled pore silicas with different particle sizes, including both non cross-linked and cross-linked samples with and without treatment with leaching conditions.

| CPS Q30 particle size | Cross-linking applied | Leaching Protocol | Productivity [kg/(kg CPS · h) | Conversion % |
|---|---|---|---|---|
| 280-500 μm | No | No | 1.21 | 29.8 |
| | | | 0.97 | 28.6 |
| 1.18-2.36 mm | No | No | 0.90 | 19.6 |
| | | | 0.89 | 19.2 |
| 280-500 μm | No | leached | 0.33 | 8.6 |
| | | | 0.30 | 8.0 |
| 1.18-2.36 mm | No | leached | 0.43 | 10.3 |
| | | | 0.49 | 11.4 |
| 280-500 μm | Yes | No | 1.18 | 27.3 |
| | | | 0.90 | 25.0 |
| 1.18-2.36 mm | Yes | No | 0.79 | 18.1 |
| | | | 0.73 | 17.3 |
| 280-500 μm | Yes | Yes | 0.67 | 18.2 |
| | | | 0.69 | 17.7 |
| 1.18-2.36 mm | Yes | Yes | 0.51 | 14.4 |
| | | | 0.55 | 14.4 |

9.8 Synthesis of Amino-Functionalised Controlled Pore Silica Q30 and Q50 with Different Particle Size Ranges.

Propylamine-functionalised CPS Q50 and CPS Q30 with 3 different particle size ranges were prepared according to the previously described protocol.

9.9 Metal Deposition and Enzyme Immobilisation

Procedures for metal deposition were performed as described previously. A freeze-dried powder of SucP2 (2.4 g) was rehydrated in 150 mM MOPS, pH 7 to obtain a cell-free extract (CFE) containing 120 mg/mL (freeze-dried powder/total volume solution). The cell-free extract (1000 μL) was transferred to Eppendorfs containing 100 mg of the amino-functionalised CPS Q30 and Q50 carriers that had been freshly deposited with zinc (1000 ppm) and incubated for 24 h (20 rpm, 25° C.). The supernatant was subsequently removed, and the immobilised catalysts were washed with 150 mM MOPS, pH 7 (2×1 mL) and used directly after removal of remaining buffer in the Eppendorfs.

9.10 Determination of Immobilisation Yield

An aliquot of initial enzyme solution or supernatant from immobilisations (100 μL) was mixed with a reaction mixture containing 1 M sucrose, 1 M glucose in deionised water (400 μL) and incubated for 1 h (600 rpm, 50° C.). The reaction was then thermally quenched at 95° C. for 5 min. 50 μL of sample was then added to 450 μL of 30 mM ribose (internal standard) followed by 500 μL ACN.

The samples were then analysed by HPLC to determine the conversion of sucrose and glucose to kojibiose. The immobilised yield was calculated by determining the percentage of enzymatic activity left in the supernatant after immobilisation compared to the enzymatic activity in the cell-free extract.

9.11 Activity of Immobilised Catalyst in Aqueous Medium

The activities of the heterogenous catalysts were determined by their ability to convert sucrose and glucose to kojibiose (Scheme 7). A reaction mixture (1 mL) containing 1 M sucrose and 1 M glucose in deionised water was added to the immobilised catalyst. The mixture was incubated for 0.5 h (1200 rpm, 55° C.). The reaction was then thermally quenched at 95° C. for 5 min. 50 μL of sample was then added to 450 μl of 30 mM ribose (internal standard) followed by 500 μL ACN. The samples were then analysed by HPLC to determine the conversion of sucrose and glucose to kojibiose.

TABLE 31

Summary of immobilisation yield and productivity of propylamine-functionalised controlled pore silicas with different particle sizes and different pore diameters.

| CPS | Particle diameter range | immobilised yield % | Kojibiose formation mM | Productivity [kg/(kg CPS · h) |
|---|---|---|---|---|
| Q30 | 75-150 μm | 38.4 | 490.8 | 1.68 |
| | 280-500 μm | 32.2 | 434.6 | 1.49 |
| | 1.18-2.36 mm | 18.9 | 168.8 | 0.58 |
| Q50 | 75-150 μm | 23.3 | 398.5 | 1.36 |
| | 280-500 μm | 30.5 | 378.0 | 1.29 |
| | 1.18-2.36 mm | 23.7 | 182.1 | 0.62 |

Example 10 Amino-Functionalised Controlled Pore Silicas Prepared Using Different Methods Two different controlled pore silicas Q30 (supplied by Fuji) and Ecovyst E30 CPS (supplied by Ecovyst) were functionalised with propylamine using 3 different application methods: namely slurry coating, spray coating and incipient wetness coating. Slurry coating is a method wherein the aminofunctionalisation of the CPS carrier is conducted by suspending the CPS carrier in a solution containing the appropriate silane. Incipient coating is a method wherein the aminofunctionalisation of the CPS carrier is conducted by applying a controlled volume of a solution containing the appropriate silane wherein the controlled volume closely matches the pore volume of the CPS carrier. Spray coating is a process in which a solution of the appropriate silane is converted via nozzles into liquid droplets and then sprayed onto a CPS carrier to enable a uniform distribution of the coating.

Any of the methods described here is capable of producing immobilisation carrier with similar performance.

10.1 Immobilisation of TLL on CPS Propylamine

A solution of Lipozyme® TL 100L, containing *Thermomyces lanuginosus* lipase (TLL) was prepared for immobilisation by dilution of the commercial enzyme (60% v/v) in deionised water (pH 6.7 of final solution). Diluted enzyme (50 mL) was transferred to a 100 mL Duran bottle containing 10 g of support (propylamine functionalised CPS Q30 supplied by Fuji and a 2nd CPS sample supplied by Ecovyst). Samples were incubated on a tilt/roller mixer for 1.5 h (70 rpm, 21° C.). After immobilisation the supernatants were removed and the immobilised supports were washed with 50 mM HEPES, 50 mM ammonium acetate, 10 mM $CaCl_2$, pH 7 solution (1×50 mL), followed by wash with 50 mM HEPES, 50 mM ammonium acetate, 10 mM $CaCl_2$, 60 mM sucrose, pH 7 solution (1×50 mL). For each washing step, the immobilised catalyst was mixed with the washing solution on a tilt/roller mixer for 3 min (70 rpm, 21° C.). The catalyst was filtered under vacuum to remove most of the washing solution (6 min), transferred to a 2 L glass flask and dried on a rotary evaporator for 55-70 min (40 mbar, 40° C.).

10.2 Activity of Immobilised TLL Catalyst for the Interesterification of Blended Soybean Oils The activities of the immobilised catalysts were evaluated for the interesterification of a soybean oil blend composed of 60% refined and bleached soybean oil and 40% fully hydrogenated soybean oil supplied by Bunge (BG F41120-000 SOY SHTG) to yield a product with a lower end melting temperature. The melted soybean oil blend (500 µL) was added to a 2 mL Eppendorf tubes containing the immobilised TLL (10 mg) and incubated for 30 min (1500 rpm, 70° C.). After stopping the mixing and allowing the catalyst to settle, an aliquot of the oil (350 pt) was transferred to a 2 mL Eppendorf tube and placed on ice-cold water to allow fat solidification and subsequently stored in a freezer (−20° C.) for at least 1 h before being analysed. The analysis of the end of melting range for the sampled reactions were performed on a Melting Point System MP55 (Mettler Toledo) with capillary tubes (Hirschmann, L 75 mm, I.D 0.95 mm, O.D. 1.35 mm) using a heating rate of 2° C./min between 34° C.-67° C. recording the end of melt temperatures as the temperature where the intensity signal (transmittance) plateaus and no further increase in intensity was detected (Table 32). The end of melting range of initial soybean oil blend is 64.7° C., and lower end of melting range represents higher degree of the occurred interesterification reaction and thereby indicates a higher enzymatic activity.

TABLE 32

Performance of immobilised Lipozyme ® TL 100L on amino-functionalised controlled pore silica supports prepared using different methods. Efficiency of catalyst in the interesterification of blended soybean oils is based on the end of melting range of the soybean oil blend after reaction.

| TLL catalyst | End of melting range [° C.] |
|---|---|
| Slurry coated CPS propylamine from Ecovyst | 55.9 |
| Incipient wetness CPS propylamine from Ecovyst | 56.1 |
| Spray coated CPS Q30 propylamine from Fuji | 56.2 |

The invention claimed is:

1. A biocatalyst for organic synthesis, comprising:

(a) a controlled porosity silica (CPS) as support material;

wherein the support material comprises an amino-functionalized surface comprising the following structure

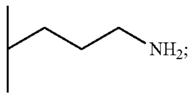

and (b) a *Thermomyces lanuginosus* lipase immobilized to the surface via non-covalent interactions;

wherein the support material has a pore diameter from about 20 nm to about 60 nm, a surface area from about 50 $m^2/g$ to about 200 $m^2/g$, and a pore volume from about 0.5 mL/g to about 2.0 mL/g.

2. A method of manufacturing a biocatalyst according to claim 1, comprising:

(a) providing one or more catalytically active enzyme(s) comprising a *Thermomyces lanuginosus* lipase;

(b) providing a controlled porosity silica (CPS) as support material, said support material comprising an amino-functionalized surface comprising the following structure

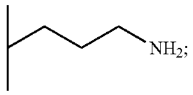

and (c) non-covalently immobilizing the one or more enzyme(s) on the support material;

wherein the support material has a pore diameter from about 20 nm to about 60 nm, a surface area from about 50 $m^2/g$ to about 200 $m^2/g$, and a pore volume from about 0.5 mL/g to about 2.0 mL/g.

3. The biocatalyst for organic synthesis according to claim 1, wherein the support material is not a caged structure.

* * * * *